US012747294B2

(12) United States Patent
Biilmann Rønn et al.

(10) Patent No.: US 12,747,294 B2

(45) Date of Patent: Sep. 29, 2026

(54) ANTI-SORTILIN ANTIBODIES AND USE THEREOF

(71) Applicant: H. Lundbeck A/S, Valby (DK)

(72) Inventors: Lars Christian Biilmann Rønn, Valby (DK); Ibrahim John Malik, Valby (DK); Jeffrey B. Stavenhagen, Valby (DK); Søren Christensen, Valby (DK); Jan Egebjerg, Valby (DK); Tina Stummann, Valby (DK); Arnout Gerritsen, Utrecht (NL); Edward van den Brink, Utrecht (NL); Paul Parren, Utrecht (NL); Esben Trabjerg, Valby (DK); Kasper Dyrberg Rand, Valby (DK)

(73) Assignee: H. Lundbeck A/S, Valby (DK)

( * ) Notice: Subject to any disclaimer, the term of this patent is extended or adjusted under 35 U.S.C. 154(b) by 1542 days.

(21) Appl. No.: 17/118,934

(22) Filed: Dec. 11, 2020

(65) Prior Publication Data

US 2021/0292414 A1 Sep. 23, 2021

Related U.S. Application Data

(62) Division of application No. 16/037,790, filed on Jul. 17, 2018, now Pat. No. 10,894,833.

(30) Foreign Application Priority Data

Jul. 20, 2017 (DK) ............................ PA201700419

(51) Int. Cl.

*C07K 16/28* (2006.01)
*A61K 39/00* (2006.01)

(52) U.S. Cl.

CPC ...... *C07K 16/286* (2013.01); *A61K 2039/505* (2013.01); *C07K 2317/21* (2013.01); *C07K 2317/34* (2013.01); *C07K 2317/76* (2013.01); *C07K 2317/92* (2013.01)

(58) Field of Classification Search

CPC .. C07K 16/28; C07K 16/286; C07K 16/2863; C07K 2317/21; C07K 2317/34; C07K 2317/76; C07K 2317/92; A61K 2039/505

See application file for complete search history.

(56) References Cited

U.S. PATENT DOCUMENTS

| | | | |
|---|---|---|---|
| 4,179,337 | A | 12/1979 | Davis et al. |
| 4,495,285 | A | 1/1985 | Shimizu et al. |
| 4,609,546 | A | 9/1986 | Hiratani |
| 4,681,581 | A | 7/1987 | Coates |
| 4,735,210 | A | 4/1988 | Goldenberg |
| 4,766,106 | A | 8/1988 | Katre et al. |
| 4,946,778 | A | 8/1990 | Ladner et al. |
| 5,101,827 | A | 4/1992 | Goldenberg |
| 5,102,990 | A | 4/1992 | Rhodes |
| 5,225,539 | A | 7/1993 | Winter |
| 5,530,101 | A | 6/1996 | Queen et al. |
| 5,545,806 | A | 8/1996 | Lonberg et al. |
| 5,545,807 | A | 8/1996 | Surani et al. |
| 5,569,825 | A | 10/1996 | Lonberg et al. |
| 5,585,089 | A | 12/1996 | Queen et al. |
| 5,589,466 | A | 12/1996 | Felgner et al. |
| 5,625,126 | A | 4/1997 | Lonberg et al. |
| RE35,500 | E | 5/1997 | Rhodes |
| 5,633,425 | A | 5/1997 | Lonberg et al. |
| 5,648,471 | A | 7/1997 | Buttram et al. |
| 5,661,016 | A | 8/1997 | Lonberg et al. |
| 5,697,902 | A | 12/1997 | Goldenberg |
| 5,741,957 | A | 4/1998 | Doboer et al. |
| 5,750,172 | A | 5/1998 | Meade et al. |
| 5,756,687 | A | 5/1998 | Denman et al. |
| 5,770,429 | A | 6/1998 | Lonberg et al. |
| 5,789,650 | A | 8/1998 | Lonberg et al. |
| 5,814,318 | A | 9/1998 | Lonberg et al. |
| 5,827,690 | A | 10/1998 | Meade et al. |
| 5,859,205 | A | 1/1999 | Adair et al. |
| 5,874,299 | A | 2/1999 | Lonberg et al. |
| 5,877,397 | A | 3/1999 | Lonberg et al. |
| 5,973,972 | A | 10/1999 | Kwon et al. |
| 6,077,835 | A | 6/2000 | Hanson et al. |
| 6,407,213 | B1 | 6/2002 | Carter et al. |
| 6,881,557 | B2 | 4/2005 | Foote |
| 10,428,147 | B2 | 10/2019 | Biilmann RøNn et al. |
| 10,479,835 | B2 | 11/2019 | Biilmann RøNn et al. |

(Continued)

FOREIGN PATENT DOCUMENTS

| | | |
|---|---|---|
| CN | 102006882 A | 4/2011 |
| CN | 106459210 A | 2/2017 |

(Continued)

OTHER PUBLICATIONS

Carlo A-S. Sortilin, a novel APOE receptor implicated in Alzheimer disease. Prion, 7(5):378-382. (Year: 2013).*

[No Author Listed], Genbank Submission; NIH/NCBI, Accession No. ADW08198.1, immunoglobulin heavy chain variable region, partial [*Homo sapiens*]. Jul. 25, 2016. www.ncbi.nlm.nih.gov/protein/ADW08198.1?report=genpept&log$=seqview 2 pages.

Arnett et al., Pro-NGF, sortilin, and p75NTR: potential mediators of injury-induced apoptosis in the mouse dorsal root ganglion. Brain Res. Dec. 5, 2007;1183:32-42. Epub Oct. 26, 2007.

International Search Report and Written Opinion mailed Oct. 26, 2016 for Application No. PCT/EP2016/066516. 24 pages.

Invitation to Pay Additional Fees mailed Oct. 30, 2018 for Application No. PCT/EP2018/069460. 17 pages.

(Continued)

*Primary Examiner* — Kimberly Ballard

(74) *Attorney, Agent, or Firm* — Wolf, Greenfield & Sacks, P.C.

(57) ABSTRACT

The present invention relates to monoclonal anti-Sortilin antibodies which have been found useful in correcting a deficient level of progranulin (PGRN). In particular, these antibodies can be used in the treatment of frontotemporal dementia (FTD) and amyotrophic lateral sclerosis (ALS) and other neurodegenerative disorders such as Alzheimers disease (AD).

12 Claims, 19 Drawing Sheets

Specification includes a Sequence Listing.

(56) References Cited

U.S. PATENT DOCUMENTS

| | | | |
|---|---|---|---|
| 10,889,650 B2 | 1/2021 | Biilmann RøNn et al. |
| 10,894,833 B2 | 1/2021 | Biilmann RøNn et al. |
| 2010/0028333 A1 | 2/2010 | Getty et al. |
| 2011/0144312 A1 | 6/2011 | Kato et al. |
| 2012/0039865 A1 | 2/2012 | Strittmatter et al. |
| 2017/0172987 A1 | 6/2017 | Herz et al. |
| 2017/0267761 A1 | 9/2017 | Biilmann Rønn et al. |
| 2018/0305455 A1 | 10/2018 | Biilmann Rønn et al. |
| 2019/0023788 A1 | 1/2019 | Rønn et al. |
| 2020/0024348 A1 | 1/2020 | Schwabe et al. |
| 2020/0190188 A1 | 6/2020 | Biilmann Rønn et al. |
| 2021/0269524 A1 | 9/2021 | Biilmann Rønn et al. |

FOREIGN PATENT DOCUMENTS

| | | |
|---|---|---|
| WO | WO 92/03918 A1 | 3/1992 |
| WO | WO 92/22645 A1 | 12/1992 |
| WO | WO 93/01227 A1 | 1/1993 |
| WO | WO 94/25585 A1 | 11/1994 |
| WO | WO 98/24884 A1 | 6/1998 |
| WO | WO 00/46147 A2 | 8/2000 |
| WO | WO 00/70087 A1 | 11/2000 |
| WO | WO 01/09187 A2 | 2/2001 |
| WO | WO 01/14424 A2 | 3/2001 |
| WO | WO 02/43478 A2 | 6/2002 |
| WO | WO 2004/056385 A2 | 7/2004 |
| WO | WO 2007/059782 A1 | 5/2007 |
| WO | WO 2008/074329 A2 | 6/2008 |
| WO | WO 2009/097006 A2 | 8/2009 |
| WO | WO 2009/132656 A2 | 11/2009 |
| WO | WO 2010/022175 A1 | 2/2010 |
| WO | WO 2010/069331 A2 | 6/2010 |
| WO | WO 2014/071131 A1 | 5/2014 |
| WO | WO 2016/164637 A1 | 10/2016 |
| WO | WO 2017/009327 A1 | 1/2017 |

OTHER PUBLICATIONS

International Search Report and Written Opinion mailed May 21, 2019 for Application No. PCT/EP2018/069460. 20 pages.

[No Author Listed] Purified Mouse Anti-Neurotensin Receptor 3. BD Transduction Laboratories. 2 pages. Retrieved from the internet www.bdbiosciences.com/ds/pm/tds/612100.pdf Last accessed Jul. 23, 2020.

Altschul, 1991 Amino Acid Substitution Matrices From an Information Theoretic Perspective, J. Mol. Biol. 219, 555-565.

Aslanidis et al., Ligation-independent cloning of PCR products (LIC-PCR). Nucleic Acids Res 1990;18(20): 6069-74.

Baker et al, Mutations in progranulin cause tau-negative frontotemporal dementia linked to chromosome 17. Nature. Aug. 24, 2006;442(7105):916-9.

Barderas et al., Affinity maturation of antibodies assisted by in silico modeling. 2008. Proc. Natl. Acad. Sci. 2008;105(26):9029-9034.

Benvenisty et al., Direct introduction of genes into rats and expression of the genes. PNAS USA. 1986;83:9551-55.

Bird et al., Single-chain antigen-binding proteins. Science. 1988;242:423-426.

Böer et al., Yeast expression platforms. Appl. Microbiol. Biotechnol. 2007;77(3):513-523.

Bostrom et al., Chapter 19: Improving Antibody Binding Affinity and Specificity for Therapeutic Development. Methods Mol. Biol. 2009;525:353-376.

Boxer et al, Frontotemporal degeneration, the next therapeutic frontier: Molecules and animal models for frontotemporal degeneration drug development. Alzheimers Dement. Mar. 2013;9(2):176-88.

Brouwers et al., Genetic variability in progranulin contributes to risk for clinically diagnosed Alzheimer disease. Neurology. Aug. 26, 2008;71(9):656-64.

Carlo et al, Sorting receptor sortilin-a culprit in cardiovascular and neurological diseases. J Mol Med (Berl). Sep. 2014;92(9):905-11.

Carrasquillo et al., Genome-wide screen identifies rs646776 near sortilin as a regulator of progranulin levels in human plasma. Am J Hum Genet. Dec. 10, 2010;87(6):890-7.

Carter et al., Humanization of an Anti-p185her2 Antibody for Human Cancer Therapy, Proc. Natl. Acad. Sci. (U.S.A.) 1992;89:4285-4289.

Celik, et al., Production of recombinant proteins by yeast cells. Biotechnol. Adv. 2012;30(5), 1108-1118.

Chen et al., B cell development in mice that lack one or both immunoglobulin kappa light chain genes. EMBO J. Mar. 1993;12(3):821-30.

Chen et al., Immunoglobulin gene rearrangement in B cell deficient mice generated by targeted deletion of the JH locus. Int Immunology. 1993;5(6):647-656.

Chen et al., Progranulin does not bind tumor necrosis factor (TNF) receptors and is not a direct regulator of TNF-dependent signaling or bioactivity in immune or neuronal cells. J Neurosci. 2013;33(21):9202-9213.

Chothia et al., Canonical structures for the Hypervariable domains of Immunoglobulins. J. Mol. Biol. 1987;196:901-917.

Clackson et al., Making antibody fragments using phage display libraries. Nature. Aug. 15, 1991;352(6336):624-8.

Co et al., Chimeric and Humanized Antibodies With Specificity for the CD33 Antigen. J. Immunol. 1992;148:1149-1154.

Co et al., Humanized Antibodies for Antiviral Therapy. Proc. Natl. Acad. Sci. (U.S.A.). 1991; 88:2869-2873.

Corsaro et al., Enhancing the efficiency of DNA-mediated gene transfer in mammalian cells. Somatic Cell Genet. Sep. 1981;7(5):603-16.

Cruts et al, Loss of progranulin function in frontotemporal lobar degeneration. Trends in Genetics. 2008;24:186-194.

Cruts et al, Null mutations in progranulin cause ubiquitin-positive frontotemporal dementia linked to chromosome 17q21. Nature. 2006;442: 920-924.

De Muynck et al, The neurotrophic properties of progranulin depend on the granulin E domain but do not require sortilin binding. Neurobiology of Aging. 2013;34(11):2541-2547.

Dumont et al, Human cell lines for biopharmaceutical manufacturing: history, status and future perspectives, Crit Rev Biotechnol. 2016;36(6):1110-1122.

Eddy, Where Did the BLOSUM62 Alignment Score Matrix Come From? Nature Biotech. 2004;22(8):1035-1036.

Edwards et al., The remarkable flexibility of the human antibody repertoire; isolation of over one thousand different antibodies to a single protein, BLyS. J Mol Biol. Nov. 14, 2003;334(1):103-18. doi: 10.1016/j.jmb.2003.09.054.

Evans et al., Rapid expression of an anti-human C5 chimeric Fab utilizing a vector that replicates in COS and 293 cells. J. Immunol. Meth. 1995;184:123-38.

Finlay et al., Affinity Maturation of a Humanized Rat Antibody for Anti-RAGE Therapy: Comprehensive Mutagenesis Reveals a High Level of Mutational Plasticity Both Inside and Outside the Complementarity-Determining Regions. J. Mol. Biol. 2009;388(3):541-558.

Fishwild et al., High-avidity human IgGk monoclonal antibodies from a novel strain of minilocus transgenic mice. Nature Biotechnology. 1996;14:845-851.

Ghaemimanesh et al., Production and Characterization of a Novel Monoclonal Antibody Against Human Sortilin. Monoclon Antib Immunodiagn Immunother. Dec. 2015;34(6):390-5. doi: 10.1089/mab.2015.0042.

Glaser et al., Antibody engineering by codon-based mutagenesis in a filamentous phage vector system. J Immunol. Dec. 15, 1992;149(12):3903-13.

Gonzales et al., SDR Grafting of a Murine Antibody Using Multiple Human Germline Templates to Minimize Its Immunogenicity. Mol. Immunol. 2004;41:863-872.

Gorman et al., Reshaping a Therapeutic CD4 Antibody, Proc. Natl. Acad. Sci. (U.S.A.). 1991;88:4181-4185.

Grant et al., Expression and Secretion Vectors for Yeast. Methods in Enzymol. 1987;153:516-544.

(56) References Cited

OTHER PUBLICATIONS

Gunasekaran et al., Enhancing antibody Fc Heterodimer formation through electrostatic steering effects: Applications to bispecific molecules and monovalent IgG. J Biolog Chem. 2010;285(5):19637-46.
Gustchina et al., Affinity maturation by targeted diversification of the cdr-h2 loop of a monoclonal fab derived from a synthetic naïve human antibody library and directed against the internal trimeric coiled-coil of gp41 yields a set of Fabs with improved HIV-1 neutralization potency and breadth. Virology. 2009;393(1):112-119.
Hackel et al., Stability and CDR Composition Biases Enrich Binder Functionality Landscapes. J. Mol. Biol. 2010;401(1):84-96.
Harding et al., Class switching in human immunoglobulin transgenic mice. N Ann NY Acad Sci. 1995;764:536-546.
He et al., Progranulin (granulin-epithelin precursor, PC-cell-derived growth factor, acrogranin) mediates tissue repair and tumorigenesis. J. Mol. Med. 2003;57:600-612.
Henikoff et al., Amino acid substitution matrices from protein blocks, Proc. Natl. Acad. Sci. (USA). 1992;89:10915-10919.
Holliger et al., "Diabodies": small bivalent and bispecific antibody fragments. Proc Natl Acad Sci U S A. Jul. 15, 1993;90(14):6444-8.
Holliger, Chapter 31: Expression of Antibody Fragments. Methods Mol. Biol. 2002;178:349-357.
Holt et al., Doman antibodies: proteins for therapy. Trends Biotechnol. Nov. 2003;2i(ll) :484-90.
Hu et al., Sortilin-mediated endocytosis determines levels of the frontotemporal dementia protein, progranulin. Neuron. Nov. 18, 2010;68(4):654-67.
Huston et al., Protein engineering of antibody binding sites: recovery of specific activity in an anti-digoxin single-chain Fv analogue produced in *Escherichia coli*. Proc. Natl. Acad. Sci. (U.S.A.) 1988;85:5879-5883.
Ito et al., Conjoint pathologic cascades mediated by ALS/FTLD-U linked RNA-binding proteins TDP-43 and FUS. Neurology. Oct. 25, 2011;77(17):1636-43.
Karlin et al., Methods for Assessing the Statistical Significance of Molecular Sequence Features by Using General Scoring Schemes. Proc. Natl. Acad. Sci. (USA). 1990;87:2264-2268.
Kettleborough et al., Humanization of a Mouse Monoclonal Antibody by CDR-Grafting: The Importance of Framework Residues on Loop Conformation. Protein Engineering. 1991;4:773-83.
Köhler et al., Continuous cultures of fused cells secreting antibody of predefined specificity. Nature. Aug. 7, 1975;256(5517):495-7.
Krause et al., An Insertion Mutation That Distorts Antibody Binding Site Architecture Enhances Function of a Human Antibody. MBio. 2011:2(1) pii: e00345-10. doi: 10.1128/mBio.00345-10.
Kuan et al., Affinity-matured anti-glycoprotein NMB recombinant immunotoxins targeting; malignant gliomas and melanomas. Int J Cancer. Jul. 1, 2011;129(1):111-21. doi:; 10.1002/ijc.25645. Epub Nov. 3, 2010.
Kurth et al., Site-Specific Conjugation of a Radioiodinated Phenethylamine Derivative to a Monoclonal Antibody Results in Increased Radioactivity Localization in Tumor. J. Med. Chem. 1993;36(9):1255-1261.
Labrijn et al., Efficient generation of stable bispecific IgG1 by controlled Fab-arm exchange. PNAS. Mar. 26, 2013;110(13):5145-50.
Le Ber et al, Demographic, neurological and behavioural characteristics and brain perfusion SPECT in frontal variant of frontotemporal dementia. Brain. 2006;129:3051-65.
Lee et al., Targeted manipulation of the sortilin-progranulin axis rescues progranulin haploinsufficiency. Hum Mol Genet. Mar. 15, 2015;23(6):1467-78. doi: 10.1093/hmg/ddt534. Epub Oct. 26, 2013.
Li et al., Expression of recombinant proteins in *Picha pastoris*. Appl Biochem Biotechnol. 2007;142(2):105-124. DOI: 10.1007/s12010-007-0003-x.
Liau et al., Identification of a human glioma-associated growth factor gene, granulin, using differential immuno-absorption. Cancer Res. 2000. 60:1353-1360.
Lindegren et al., Chloramine-T in High-Specific-Activity Radioiodination of Antibodies Using N-Succinimidyl-3-(Trimethylstannyl)Benzoate as an Intermediate. Nucl. Med. Biol. 1998;25(7):659-665.
Lloyd et al., Modelling the human immune response: performance of a 1011 human antibody repertoire against a broad panel of therapeutically relevant antigens. Protein Eng Des Sel. Mar. 2009;22(3):159-68. doi: 10.1093/protein/gzn058. Epub Oct. 29, 2008.
Lobuglio et al., Mouse/Human Chimeric Monoclonal Antibody in Man: Kinetics and Immune Response. Proc. Natl. Acad. Sci. (U.S. A.). 1989;86:4220-4224.
Lonberg et al., Antigen-sepcific human antibodies from mice comprising four distinct genetic modifications. Nature. 1994;368:856-9.
Lonberg et al., Human antibodies from transgenic mice. Intern. Rev. Immunol. 1995;13:65-93.
Lu et al., Mediation of estrogen mitogenic effect in human breast cancer MCF-7 cells by PC-cell-derived growth factor (PCDGF/granulin precursor). Proc. Natl Acad Sci U.SA. 2001;98:142-147.
Mabry et al., Engineering of stable bispecific antibodies targeting IL-17A and IL-23. PEDS. 2010;23(3):115-127.
Maeda et al., Construction of Reshaped Human Antibodies With HIV-Neutralizing Activity. Human Antibodies Hybridoma. 1991;2:124-134.
Mariuzza et al., The structural basis of antigen-antibody recognition. Annu Rev Biophys Chem. 1987;16:139-59.
Marks et al., By-passing immunization. Human antibodies from V-gene libraries displayed on phage. J Mol Biol. Dec. 5, 1991;222(3):581-97.
Mattanovich et al., Chapter 17: Recombinant Protein Production in Yeasts. Methods Mol. Biol. 2012; 824:329-358.
Mccafferty et al., Phage antibodies: filamentous phage displaying antibody variable domains. Nature. 1990;348:552-554.
Metz et al., Bispecific antibody derivatives with restricted binding functionalities that are activated by proteolytic processing. Protein Engineering. 2012; 25(10):571-580.
Minami et al., Progranulin protects against amyloid β deposition and toxicity in Alzheimer's disease mouse models. Nat Med. Oct. 2014;20(10):1157-64.
Monami et al., Proepithelin Promotes Migration and Invasion of 5637 Bladder Cancer Cells through the Activation of ERK1/2 and the Formation of a Paxillin/FAK/ERK Complex. Cancer Res. 2006;66(14):7103-10.
Montgomery et al., Affinity maturation and characterization of a human monoclonal antibody against HIV-1 gp41. MAbs. Sep.-Oct. 2009;1(5):462-74. Epub Sep. 8, 2009.
Moore et al., A novel bispecific antibody format enables simultaneous bivalent and monovalent co-engagement of distinct target antigens. MAbs. Nov.-Dec 2011;3(6):546-57. doi: 10.4161/mabs.3.6.18123. Epub Nov. 1, 2011.
Nguyen et al., Progranulin: at the interface of neurodegenerative and metabolic diseases. Trends Endocrinol Metab. Dec. 2013;24(12):597-606.
Nykjær et al, Sortilin: a receptor to regulate neuronal viability and function. Trends Neurosci. Apr. 2012;35(4):261-70. doi: 10.1016/j.tins.2012.01.003. Epub Feb. 16, 2012. Review.
Nykjaer et al., Sortilin is essential for proNGF-induced neuronal cell death. Nature. Feb. 26, 2004;427(6977):843-8.
Quistgaard et al, Ligands bind to Sortilin in the tunnel of a ten-bladed beta-propeller domain. Nat Struct Mol Biol. Jan. 2009;16(1):96-8. doi: 10.1038/nsmb.1543. Epub Jan. 4, 2009.
Quistgaard et al, Revisiting the structure of the Vps10 domain of human sortilin and its interaction with neurotensin. Protein Sci. Sep. 2014;23(9):1291-300. doi: 10.1002/pro.2512. Epub Jul. 22, 2014.
Rademakers et al, Advances in understanding the molecular basis of frontotemporal dementia. Nat Rev Neurol. Aug. 2012;8(8) 423-34.
Rasmussen et al., Transient p53 suppression increases reprogramming of human fibroblasts without affecting apoptosis and DNA damage. Stem Cell Reports. Sep. 9, 2014;3(3):404-13. doi: 10.1016/j.stemcr.2014.07.006. Epub Aug. 21, 2014.
Rea et al., Site-specifically radioiodinated antibody for targeting tumors. Cancer Res. 1990;50(3 Suppl):857s-861s.
Revets et al., Nanobodies as novel agents for cancer therapy. Expert Opin Biol Ther. Jan. 2005;5(1):111-24.

(56) References Cited

OTHER PUBLICATIONS

Ridgway et al., 'Knobs-into-holes' engineering of antibody CH3 domains for heavy chain heterodimerization. Protein Eng. Jul. 1996;9(7):617-21.
Riechmann et al., Reshaping human antibodies for therapy. Nature. Mar. 24, 1988;332(6162):323-7.
Sato et al., Reshaping a human antibody to inhibit the interleukin 6-dependent tumor cell ; growth. Cancer Res. Feb. 15, 1993;53(4):851-6.
Schakowski et al., A Novel Minimal-Size Vector (MIDGE) Improves Transgene Expression in Colon Carcinoma Cells and Avoids Transfection of Undesired DNA. Mol Ther. 2001:3(5):793-800.
Schrøder et al., The identification of AF38469: An orally bioavailable inhibitor of the VPS10P family sorting receptor Sortilin. Bioorg Med Chem Lett. Jan. 1, 2014;24(1):177-80.
Serrero, Autocrine growth factor revisited: PC-cell-derived growth factor (progranulin), a critical player in breast cancer tumorigenesis. Biochem Biophys. Res. Commun. 2003;308:409-413.
Sheng et al., Progranulin polymorphism rs5848 is associated with increased risk of Alzheimer's disease. Gene. Jun. 1, 2014;542(2):141-5.
Spreter Von Kreudenstein et al., Improving biophysical properties of a bispecific antibody scaffold to aid developability: quality by molecular design. MAbs. 2013; 5(2);646-54.
Steidl et al., In Vitro Affinity Maturation of Human GM-CSF Antibodies by Targeted CDR-Diversification. Mol. Immunol. 2008;46(1):135-144.
Strop et al., Generating Bispecific Human IgG1 and IgG2 Antibodies from Any Antibody Pair. JMB. 2012;420:204-19.
Sykes et al., Linear expression elements: a repid, in vivo, method to screen for gene functions. Nat Biotech. Apr. 1997;17:355-9.
Takamura et al., Sortilin is required for toxic action of Aβ oligomers (AβOs): extracellular AβOs trigger apoptosis, and intraneuronal AβOs impair degradation pathways. Life Sci. Dec. 10, 2012;91(23-24):1177-86. doi: 10.1016/j.lfs.2012.04.038. Epub May 3, 2012.
Tang et al., The growth factor progranulin binds to TNF receptors and is therapeutic against inflammatory arthritis in mice. Science. Apr. 22, 2011;332(6028):478-84. doi: 10.1126/science.1199214. Epub Mar. 10, 2011.
Tangkeangsirisin et al., PC cell-derived growth factor (PCDGF/GP88, progranulin) stimulates migration, invasiveness and VEGF expression in breast cancer cells. Carcinogenesis. Sep. 2004;25(9):1587-92. Epub Apr. 29, 2004.
Taylor et al., A transgenic mouse that expresses a diversity of human sequence heavy and light chain immunoglobulins. Nucleic Acids Res. Dec. 11, 1992;20(23):6287-95.
Taylor et al., Human immunoglobulin transgenes undergo rearrangement, somatic mutation and class switching in mice that lack endogenous IgM. Int Immunol. Apr. 1994;6(4):579-91.
Tempest et al., Reshaping a human monoclonal antibody to inhibit human respiratory syncytial virus infection in vivo. Biotechnology (N Y). Mar. 1991;9(3):266-71.
Tuaillon et al., Biased utilization of DHQ52 and JH4 gene segments in a human Ig transgenic minilocus is independent of antigenic selection. J Immunol. Mar. 5, 1994;152(6):2912-20.
Van Der Vaart, Expression of VHH antibody fragments in *Saccharomyces; cerevisiae*. Methods Mol Biol. 2002; 178:359-66. Review.
Van Heeke et al., Expression of human asparagine synthetase in *Escherichia coli*. J Biol Chem. Apr. 5, 1989;264(10):5503-9.
Verhoeyen et al., Reshaping Human Antibodies: Grafting an Antilysozyme Activity. Science. Mar. 25, 1988;239:1534-1536.
Vincent et al., Neurotensin and neurotensin receptors. Trends Pharmacol Sci. Jul. 1999;20(7):302-9.
Ward et al., Binding activities of a repertoire of single immunoglobulin variable domains secreted from *Escherichia coli*. Nature. Oct. 12, 1989;341(6242):544-6.
Wigler et al., Biochemical transfer of single-copy eucaryotic genes using total cellular DNA as donor. Cell. Jul. 1978;14(3):725-31.
Wu et al., Stepwise in vitro affinity maturation of Vitaxin, an alphav beta3-specific humanized mAb. Proc Natl Acad Sci U S A. May 26, 1998;95(11):6037-42.
Yelton et al., Affinity maturation of the BR96 anti-carcinoma antibody by codon-based mutagenesis. J Immunol. Aug. 15, 1995;155(4):1994-2004.
Zheng et al., C-terminus of progranulin interacts with the beta-propeller region of sortilin to regulate progranulin trafficking. PLoS One. 2011;6(6):e21023. doi: 10.1371/journal.pone.0021023. Epub Jun. 15, 2011.
Zhu et al., Conversion of proepithelin to epithelins: roles of SLPI and elastase in host defense and wound repair. Cell. Dec. 13, 2002;111(6):867-78.

* cited by examiner

FIG. 2C

| mAbs | Domain | hSort | hB01-05 | hB06-10 | B12390 | B45678 | Tet |
|---|---|---|---|---|---|---|---|
| 6 | A | + | + | - | + | - | - |
| 0 | B | + | + | - | - | + | - |
| 2 | C | + | - | + | - | + | - |
| 17 | D | + | - | + | + | - | - |
| 26 | E | + | - | + | + | + | - |
| 6 | D+ | + | - | - | + | - | - |
| 2 | Tet | + | + | + | + | + | + |
| 3 | Other | + | +/- | +/- | +/- | + | - |

FIG. 3A

| Antibody | Sort WT | hB01-05 | hB06-10 | hB12390 | hB45678 | hBack | hRim | Tetra |
|---|---|---|---|---|---|---|---|---|
| IgG1-6003-030 | 0.89 | NB | 0.74 | 0.82 | 0.85 | 0.85 | 0.86 | NB |
| IgG1-6003-010 | 2.45 | NB | 2.29 | 3.00 | 4.39 | 2.85 | 3.77 | NB |
| IgG1-6003-028 | 1.75 | NB | 1.56 | 1.86 | 1.96 | 1.87 | 2.04 | NB |
| IgG1-6003-056 | 1.26 | NB | 0.97 | 1.42 | 1.10 | 1.14 | 1.24 | NB |
| IgG1-6003-072 | 2.03 | NB | 1.96 | 6.29 | 4.41 | 2.63 | 4.93 | NB |
| IgG1-6003-083 | 0.77 | NB | 0.76 | 0.86 | 0.92 | 1.34 | 0.99 | NB |
| IgG1-6003-1277 | 3.03 | NB | 2.62 | 3.63 | 4.30 | 4.07 | 4.34 | NB |
| IgG1-6003-1286 | 1.02 | NB | 0.87 | 0.86 | 1.02 | 1.02 | 1.05 | NB |
| IgG1-6003-1342 | 1.79 | NB | 1.49 | 2.08 | 2.51 | 1.84 | 2.44 | NB |
| IgG1-6003-381 | 1.82 | NB | 1.34 | 1.93 | 2.00 | 1.60 | 2.28 | NB |
| IgG1-6003-408 | 1.93 | NB | 1.68 | 2.21 | 2.58 | 2.37 | 2.78 | NB |
| IgG1-6003-423 | 3.47 | NB | 2.96 | 3.55 | 4.45 | 4.00 | 4.24 | NB |
| IgG1-6003-471 | 2.63 | NB | 2.06 | 3.16 | 2.93 | 2.54 | 3.65 | NB |
| IgG1-6003-530 | 4.77 | NB | 5.77 | 8.37 | 14.89 | 8.01 | 11.99 | NB |
| IgG1-6003-532 | 1.30 | NB | 1.01 | 1.23 | 1.35 | 1.25 | 1.42 | NB |
| IgG1-6003-784 | 2.14 | NB | 2.33 | 4.27 | 6.50 | 3.25 | 5.86 | NB |

FIG. 3B

| | | | | | | | | |
|---|---|---|---|---|---|---|---|---|
| IgG1-6003-799 | 3.49 | NB | 2.63 | 3.36 | 4.16 | 3.20 | 5.02 | NB |
| IgG1-6003-822 | 1.97 | NB | 1.49 | 1.89 | 2.08 | 2.59 | 2.31 | NB |
| IgG1-6003-826 | 6.54 | NB | 6.95 | 15.40 | 18.06 | 9.36 | 18.27 | NB |
| IgG1-6003-886 | 3.40 | NB | 2.44 | 3.36 | 3.45 | 2.72 | 4.42 | NB |
| IgG1-6003-899 | 3.06 | NB | 2.32 | 17.70 | 5.55 | 4.54 | 5.35 | NB |
| IgG1-6003-900 | 1.06 | NB | 0.91 | 1.06 | 1.19 | 1.16 | 1.26 | NB |
| IgG1-6003-910 | 1.34 | NB | 1.16 | 1.84 | 2.23 | 1.54 | 2.59 | NB |
| IgG1-6003-936 | 2.18 | NB | 1.85 | 11.40 | 2.86 | 2.62 | 3.20 | NB |
| IgG1-6003-995 | 2.03 | NB | 1.42 | 10.21 | 2.99 | 2.03 | 3.31 | NB |
| IgG1-6003-972 | 1.35 | NB | 1.12 | 2.36 | 2.57 | 1.49 | 3.08 | NB |

| **Homogenous binding legend** | |
|---|---|
| + | EC50 0.1-10 ng/ml |
| + | EC50 >10 ng/ml |
| NB | no binding |

FIG. 4A

| | | E | E | E | E | E | E | E | E | E | E | E | E | E |
|---|---|---|---|---|---|---|---|---|---|---|---|---|---|---|
| Domain | Antibody | 530 | 784 | 010 | 471 | 532 | 910 | 072 | 972 | 826.0 | 028 | 030 | 056 | 083 |
| E | 530 | 0.00 | 0.00 | -0.01 | -0.01 | -0.01 | 0.00 | 0.00 | -0.01 | 0.01 | -0.04 | -0.04 | -0.04 | -0.03 |
| E | 784 | -0.01 | -0.01 | 0.00 | -0.01 | 0.00 | 0.00 | -0.01 | 0.00 | 0.00 | -0.01 | -0.01 | -0.03 | -0.01 |
| E | 010 | 0.00 | 0.01 | 0.01 | 0.02 | 0.01 | 0.03 | 0.00 | 0.02 | 0.03 | 0.02 | 0.01 | 0.00 | 0.01 |
| E | 471 | 0.01 | 0.02 | 0.00 | 0.01 | 0.02 | 0.02 | 0.01 | 0.02 | 0.02 | 0.01 | 0.01 | 0.01 | 0.02 |
| E | 532 | 0.01 | 0.01 | 0.00 | 0.02 | 0.01 | 0.03 | 0.01 | 0.01 | 0.03 | 0.00 | 0.01 | 0.01 | 0.01 |
| E | 910 | 0.02 | 0.03 | 0.01 | 0.02 | 0.03 | 0.04 | 0.02 | 0.04 | 0.05 | 0.01 | 0.02 | 0.00 | 0.02 |
| E | 072 | 0.00 | 0.00 | 0.00 | 0.00 | 0.00 | 0.02 | 0.00 | 0.01 | 0.01 | -0.01 | 0.00 | 0.00 | 0.00 |
| E | 972 | x | x | 0.01 | 0.10 | x | x | 0.06 | x | x | 0.00 | 0.00 | 0.06 | 0.06 |
| E | 826 | 0.00 | 0.00 | 0.00 | -0.01 | -0.01 | 0.00 | 0.00 | 0.00 | 0.01 | -0.03 | -0.03 | -0.05 | -0.03 |
| E | 028 | 0.03 | 0.04 | 0.00 | 0.02 | 0.04 | 0.07 | 0.01 | 0.04 | 0.06 | 0.00 | 0.00 | 0.01 | 0.02 |
| E | 030 | 0.03 | 0.03 | 0.00 | 0.02 | 0.04 | 0.06 | 0.01 | 0.05 | 0.06 | 0.00 | 0.01 | 0.01 | 0.02 |
| E | 056 | 0.01 | 0.01 | 0.01 | 0.00 | 0.01 | 0.02 | -0.07 | 0.01 | 0.02 | 0.01 | 0.01 | 0.00 | 0.01 |
| E | 083 | 0.02 | 0.02 | 0.00 | 0.02 | 0.02 | 0.03 | 0.02 | 0.03 | 0.05 | 0.00 | 0.01 | 0.01 | 0.02 |

FIG. 4B

| | | | | | | | | | | | | | | |
|---|---|---|---|---|---|---|---|---|---|---|---|---|---|---|
| E | 381 | 0.01 | 0.02 | 0.00 | 0.01 | 0.01 | 0.02 | 0.02 | 0.03 | 0.03 | 0.00 | 0.01 | 0.00 | 0.01 |
| E | 408 | 0.01 | 0.02 | 0.00 | 0.01 | 0.02 | 0.05 | 0.00 | 0.03 | 0.04 | 0.01 | 0.01 | 0.00 | 0.01 |
| E | 423 | 0.01 | 0.02 | 0.01 | 0.01 | 0.01 | 0.03 | 0.01 | 0.02 | 0.04 | -0.01 | -0.01 | -0.02 | 0.00 |
| E | 799 | 0.02 | 0.01 | 0.01 | 0.01 | 0.01 | 0.05 | 0.00 | 0.02 | 0.03 | 0.00 | 0.05 | 0.00 | 0.01 |
| E | 822 | 0.00 | 0.01 | 0.01 | 0.01 | 0.00 | 0.01 | 0.00 | 0.01 | 0.01 | 0.00 | 0.02 | 0.00 | 0.01 |
| E | 1286 | 0.04 | 0.04 | 0.00 | 0.05 | 0.04 | 0.05 | 0.03 | 0.04 | 0.07 | 0.01 | 0.01 | 0.03 | 0.04 |
| E | 1342 | 0.01 | 0.02 | 0.02 | 0.00 | 0.03 | 0.03 | 0.02 | 0.03 | 0.07 | 0.01 | -0.04 | -0.01 | 0.01 |
| E | 900 | 0.02 | 0.03 | 0.00 | 0.02 | 0.02 | 0.05 | 0.01 | 0.03 | 0.04 | -0.01 | -0.02 | -0.01 | 0.00 |
| E | 1277 | 0.02 | 0.01 | 0.00 | 0.08 | 0.02 | 0.04 | 0.01 | 0.02 | 0.04 | 0.01 | 0.01 | 0.01 | 0.02 |
| E | 899* | b | b | b | b | b | B | x | ND | x | x | x | x | x |
| E | 995 | b | b | 0.21 | b | b | b | x | x | x | -0.03 | -0.03 | x | x |
| E | 936 | b | b | 0.71 | 0.33 | b | b | x | x | x | -0.22 | -0.20 | -0.07 | x |
| E | 886 | 0.34 | 0.39 | 0.37 | 0.57 | 0.58 | 0.37 | 0.02 | 0.02 | 0.02 | 0.00 | 0.00 | 0.01 | 0.01 |

FIG. 4C

| | | E | E | E | E | E | E | E | E | E | E | E | E | E |
|---|---|---|---|---|---|---|---|---|---|---|---|---|---|---|
| Domain | Antibody | 381 | 408 | 423 | 799 | 822 | 1286 | 1342 | 900 | 1277 | 899 | 995 | 936 | 886 |
| E | 530 | -0.01 | -0.02 | -0.01 | 0.00 | 0.00 | -0.03 | -0.01 | -0.03 | -0.01 | b | b | b | b |
| E | 784 | -0.01 | 0.00 | 0.00 | 0.00 | 0.00 | -0.02 | -0.01 | -0.01 | -0.01 | b | b | b | b |
| E | 010 | 0.00 | 0.01 | 0.01 | 0.02 | 0.03 | 0.01 | 0.03 | 0.02 | 0.01 | 0.52 | 0.60 | 0.53 | 0.44 |
| E | 471 | 0.01 | 0.02 | 0.01 | 0.02 | 0.01 | 0.01 | 0.02 | 0.02 | 0.01 | 0.54 | 0.62 | 0.58 | 0.54 |
| E | 532 | 0.01 | 0.01 | 0.01 | 0.02 | 0.03 | 0.02 | 0.03 | 0.01 | 0.01 | 0.64 | 0.71 | 0.64 | 0.51 |
| E | 910 | 0.01 | 0.02 | 0.04 | 0.03 | 0.03 | 0.02 | 0.04 | 0.03 | 0.02 | 0.23 | 0.31 | 0.35 | 0.51 |
| E | 072 | 0.00 | 0.00 | 0.00 | 0.01 | 0.01 | 0.00 | 0.02 | 0.00 | 0.00 | 0.01 | 0.02 | 0.01 | 0.05 |
| E | 972 | x | x | 0.10 | x | x | x | x | x | x | ND | ND | ND | x |
| E | 826 | 0.00 | -0.01 | 0.00 | 0.00 | 0.00 | -0.03 | 0.00 | -0.03 | -0.01 | -0.02 | -0.02 | -0.03 | 0.00 |
| E | 028 | 0.02 | 0.02 | 0.03 | 0.05 | 0.07 | 0.04 | 0.07 | 0.04 | 0.04 | 0.02 | 0.02 | -0.11 | 0.04 |
| E | 030 | 0.02 | 0.03 | 0.03 | 0.04 | 0.05 | 0.03 | 0.05 | 0.04 | 0.03 | 0.01 | 0.01 | -0.10 | 0.03 |
| E | 056 | 0.00 | 0.01 | 0.01 | 0.01 | 0.01 | 0.01 | 0.03 | 0.01 | 0.01 | 0.01 | 0.00 | -0.04 | 0.01 |
| E | 083 | 0.01 | 0.02 | 0.02 | 0.02 | 0.04 | 0.02 | 0.03 | 0.02 | 0.02 | 0.01 | -0.02 | -0.07 | 0.02 |

FIG. 4D

| | | | | | | | | | | | | | | |
|---|---|---|---|---|---|---|---|---|---|---|---|---|---|---|
| E | 381 | 0.01 | 0.01 | 0.02 | 0.02 | 0.02 | 0.01 | 0.03 | 0.02 | 0.01 | 0.01 | 0.01 | -0.07 | 0.01 |
| E | 408 | 0.00 | 0.01 | 0.02 | 0.02 | 0.06 | 0.02 | 0.03 | 0.02 | 0.02 | 0.02 | 0.05 | 0.02 | 0.01 |
| E | 423 | 0.00 | 0.01 | 0.00 | 0.02 | 0.02 | 0.00 | 0.03 | 0.01 | 0.01 | 0.01 | 0.00 | -0.03 | 0.01 |
| E | 799 | 0.01 | 0.01 | 0.01 | 0.01 | 0.03 | 0.02 | 0.03 | 0.01 | 0.02 | 0.01 | 0.02 | -0.09 | 0.02 |
| E | 822 | 0.00 | 0.00 | 0.01 | 0.01 | 0.01 | 0.01 | 0.01 | 0.00 | 0.01 | 0.01 | 0.00 | -0.03 | 0.00 |
| E | 1286 | 0.03 | 0.04 | 0.04 | 0.04 | 0.04 | 0.04 | 0.04 | 0.04 | 0.04 | 0.04 | 0.03 | -0.01 | 0.04 |
| E | 1342 | 0.00 | 0.02 | 0.01 | 0.03 | 0.01 | 0.01 | 0.03 | 0.02 | 0.01 | 0.00 | -0.03 | -0.09 | 0.01 |
| E | 900 | 0.01 | 0.01 | 0.01 | 0.03 | 0.03 | 0.02 | 0.05 | 0.02 | 0.04 | 0.03 | 0.04 | 0.03 | 0.02 |
| E | 1277 | 0.01 | 0.02 | 0.01 | 0.02 | 0.03 | 0.02 | 0.04 | 0.02 | 0.02 | 0.02 | 0.03 | 0.02 | 0.02 |
| E | 899* | x | x | x | x | x | x | x | x | x | ND | ND | ND | x |
| E | 995 | x | x | x | x | x | x | x | x | x | ND | ND | ND | x |
| E | 936 | x | x | x | x | x | x | x | x | x | ND | ND | ND | x |
| E | 886 | 0.01 | 0.01 | 0.01 | 0.02 | 0.02 | 0.01 | 0.01 | 0.01 | 0.02 | 0.01 | 0.02 | 0.01 | 0.01 |

| | | | |
|---|---|---|---|
| 0 | response <0.1 | b = binding - no cross block | ND= not done |
| 0.2 | response >0.1 | x = no binding - cross block | |

617-629 YTIWLAHSTDPED (SEQ ID NO: 157)

ANTI-SORTILIN ANTIBODIES AND USE THEREOF

CROSS-REFERENCE TO RELATED APPLICATION(S)

This application is a Divisional Application of U.S. application Ser. No. 16/037,790, filed Jul. 17, 2018, which claims priority to Danish Application No. PA201700419, filed Jul. 20, 2017, the entire contents of each of which are incorporated herein by reference.

FIELD OF THE INVENTION

The present invention relates to monoclonal anti-Sortilin antibodies useful in correcting a deficient level of progranulin (PGRN). In particular these antibodies can be used in the treatment of frontotemporal dementia (FTD) and amyotrophic lateral sclerosis (ALS). Furthermore, it is anticipated that the monoclonal antibodies may also be useful to treat neurodegenerative disorders such as Alzheimer's Disease (AD).

REFERENCE TO SEQUENCE LISTING

The contents of the electronic sequence listing (H095270075US01-SUBSEQ-CNS.txt; Size: 130,314 bytes; and Date of Creation: Apr. 8, 2026) are herein incorporated by reference in their entirety.

BACKGROUND OF THE INVENTION

Sortilin is a receptor that has been reported to mediate pro-apoptotic effects of pro-neurotrophins and to mediate trafficking and sorting of neurotrophin receptors (Nykjær et al, 2012, Trends Neurosci. 2012; 35(4):261-70; Glerup et al, Handb Exp Pharmacol, 2014; 220:165-89, Carlo et al, J Mol Med (Berl). 2014 September; 92(9):905-11). A number of sortilin ligands have been identified including neurotensin for which a high affinity binding site was localized by x-ray crystallography to be inside a beta propeller tunnel in the sortilin molecule (Quistgaard et al, Nat Struct Mol Biol. 2009 January; 16(1):96-8; Quistgaard et al, Protein Sci. 2014 September; 23(9):1291-300). More recently, sortilin was shown to function as a high affinity receptor for the growth factor progranulin (PGRN, Hu et al. Neuron. 2010 Nov. 18; 68(4):654-67.

PGRN ((proepithelin, granulin-epithelin precursor, PC-cell-derived growth factor, acrogranin)) is a secreted glycosylated protein with anti-inflammatory and neurotrophic-like actions (For a recent review, see Nguyen, Trends Endocrinol Metab. 2013 December; 24(12):597-606). PGRN is proteolytically cleaved to granulins, but much remains to be learned regarding the physiological role of PGRN and granulins and the identity of their receptors. PGRN has been implicated in several cellular functions including cell cycle regulation and cell motility (He, Z. & Bateman, A., J. Mol. Med. 57:600-612 (2003); Monami, G., et al., Cancer Res. (5(5:7103-7110 (2006)), wound repair, inflammation (Zhu, J., et al., Cell 777:867-878 (2002)), induction of growth factors such as vascular endothelial growth factor (VEGF) (Tangkeangsittsin, W. & Serrero, G, Carcinogenesis 25.1587-1592 (2004)), and tumorigenesis (He, Z. & Bateman, A., J. Mol. Med. 81:600-612 (2003), Monami, G., et al., Cancer Res (5 (5:7103-7110 (2006); Serrero, G., Biochem Biophys. Res. Commun. 505-409-413 (2003), Lu, R & Serrero, G., Proc. Natl Acad Sci USA 98 142-147 (2001); Liau, L M., et al., Cancer Res. 60:1353-1360 (2000)). PGRN has been reported to bind the TNF receptor (Tang W et al., Science 2011, 332(6028):478-84). but this observation has been challenged by others (Chen et al., J Neurosci. 2013, 33(21):9202-9213).

The binding of PGRN to sortilin has been mapped to the neurotensin site and reported to be mediated solely through the PGRN C-terminal domain (Zheng et al. PLoS One. 2011; 6(6):e21023; Lee et al. Hum Mol Genet. 2013) in a manner similar to neurotensin and in accordance, neurotensin has been shown to block the interaction of sortilin with PGRN and other ligands. Upon binding, sortilin mediates lysosomal clearance of PGRN and thereby regulates extracellular PGRN levels (Hu et al. 2010). Thus, knockdown or overexpression of sortilin have been shown to regulate extracellular PGRN levels in cell culture (Carrasquillo et al. Am J Hum Genet. 2010 Dec. 10; 87(6):890-7) and in mice, sortilin deficiency was reported to increase PGRN levels and to restore plasma and brain PGRN-levels in PGRN+/− mice (Hu et al. 2010). Interestingly, a single nucleotide polymorphism (SNP) near sortilin was associated with decreased plasma PGRN and increased sortilin mRNA levels (Carrasquillo et al. Am J Hum Genet. 2010 Dec. 10; 87(6):890-7). These observations suggest that sortilin is a key regulator of extracellular PGRN.

PGRN has been linked to frontotemporal dementia (FTD), a progressive dementia characterized by behavioral and semantic changes, as well as frontotemporal lobar degeneration (FTLD) and neuronal inclusions containing TAR DNA Binding Protein-43 (TDP-43) or tau inclusions (Baker et al, 2006, Nature. 2006 Aug. 24; 442 (7105): 916-9; Cruts et al, Nature 442:920-924 (2006); Am J Hum Genet. 2010 Dec. 10; 87(6):890-7, M et al, Trends in Genetics 24:186-194 (2008)). The majority of sporadic and familial FTD cases show TDP-43 pathology (~50%) similar to ALS and FTD-TDP43 and ALS are by some considered to constitute a disease spectrum (Ito D Neurology. 2011 Oct. 25; 77(17):1636-43; Boxer A L et al, Alzheimers Dement. 2013 March; 9(2):176-88; Rademakers et al, Nat Rev Neurol. 2012 August; 8(8):423-434) due to common pathologies and genetic factors and some overlap in symptomatology. No disease-modifying treatment options are available for FTD. A subset of frontotemporal dementia patients with TDP-43 pathology have loss of function mutations in the granulin gene (GRN) resulting in PGRN haplo-insufficiency. More than 75 different mutations in the granulin gene, all resulting in reduced PGRN levels and/or function, have been associated with FTD and it is believed that raising extracellular PGRN in plasma and brain would counteract the disease process.

PGRN mutations have also been linked with Alzheimer's disease (AD) (Sheng et al., 2014, Gene. 2014 Jun. 1; 542(2):141-5; Brouwers et al., 2008, Neurology. 2008 Aug. 26; 71(9):656-64) suggesting that PGRN deficiency may play an important role in AD pathogenesis. Furthermore, neuroprotective effects of PGRN in mouse AD models have been observed (Minami et al, 2014, Nat Med. 2014 October; 20(10):1157-64) providing support for the view that enhanced PGRN may be beneficial in AD and possibly other neurodegenerative conditions.

The present application describes the generation and identification of anti-human Sortilin antibodies which can regulate PGRN in cellular models and in mice. Those antibodies surprisingly bind to a region on Sortilin which is distant to the previously reported progranulin binding site, the so-called neurotensin-site, and yet are capable of increasing extracellular PGRN.

The inventors have defined six Sortilin binding regions and identified efficacious antibodies that bind a region ("region E"). These antibodies do not block PGRN binding to sortilin yet influence/increase PGRN levels suggesting a novel mode of action for these antibodies. As PGRN has neuroprotective and antiinflammatory effects, the inventors' findings indicate that such antibodies targeting Sortilin are likely to have a beneficial effect in the treatment of a range of neurodegenerative disorders including FTD/FTLD. A subgroup of FTD/FTLD patients with TDP-43 pathology carry a mutation in the gene encoding PGRN leading to PGRN haploinsufficiency. Sortilin antibodies are expected to counteract this PGRN deficiency and likely will have similar therapeutic benefits for patients suffering from other TDP-43 proteinopathies in which PGRN levels may influence TDP43-function and pathology, including ALS and in other neurodegenerative diseases in which increased PGRN function may be neuroprotective including AD.

SUMMARY OF INVENTION

The inventors of the present invention have generated monoclonal antibodies which surprisingly bind to a novel Sortilin region denominated the "E-region" as defined in SEQ ID NO:146 and is able to modulate the PGRN levels in the brain of a patient.

The invention also relates to a method of preventing or treating a disease associated with decreased PGRN levels in the brain of a patient, comprising administering an effective dosage of an antibody or an antigen-binding fragment thereof that binds to the E-region of Sortilin. These diseases include i.a. FTD, ALS and proteinopathies such as AD, PD.

BRIEF DESCRIPTION OF THE DRAWINGS

FIGS. 2A-2C show the region assignment of antibodies based on binding to Sortilin shuffle constructs.

FIG. 2A shows a linear illustration of the shuffle constructs used for region assignment of antibodies as described in Example 1. Sortilin shuffle constructs were generated based on the human Sortilin sequence (SEQ ID NO:145) (sections depicted in grey) in which amino acid residues were exchanged to the corresponding amino acid from the tetraodon Sortilin sequence (depicted in black) (SEQ ID NO: 149) (Examples 1-3).

FIG. 2B shows predicted structure of the shuffle constructs illustrated linearly in A. Dark residues indicate residues changed to the corresponding tetraodon sequence in the shuffle constructs.

FIG. 2C illustrates the binding pattern of antibodies assigned to the D-region and the E region classes respectively. A "+" indicates binding to a given shuffle construct and a "−" indicates lack of binding. Based on the binding pattern to the different shuffle constructs, antibodies were assigned to regions. The resultant antibody region classes are indicated by A-E. For the illustrated D and E region antibodies, both bound the human sequences (all grey) as indicated by "+" and neither bound the tetraodon sequence (all black) as indicated by "−", whereas the E region antibody bound the hB45678 shuffle construct while the D Region antibody did not bind resulting in the localisation of binding as illustrated in Panel A. For E Region antibodies, binding to the following shuffle regions was observed: hsort, hB06-10, B12390, hB45678. The antibodies did not bind to hB01-05 and tetraodon constructs. The antibodies did not bind to the fully tetraodon Sortilin protein, except two. The two antibodies capable of binding the tetraodon sequence were denoted "tet". "Other" refers to an antibody which could not be assigned to one region.

FIGS. 3A-3B show binding affinities of human E-domain antibodies. Binding affinities to sortilin constructs by bio-Layer interferometry using Octet384RED as described in example 2 (EC50, ng/ml). NB indicates No Binding. Values between 0.1-10 ng/ml and >10 ng/ml indicate binding. Region assignment was based on binding patterns of the antibodies to different sortilin shuffle constructs (FIGS. 2A-2C). Lack of binding with sortilin construct hB01-05 and Tetra suggest these antibodies bind to E region.

FIGS. 4A-4D show cross-blocking between E-domain antibodies. Each antibody was bound to human wildtype Sortilin to form an antibody-sortilin complex. All other E domain antibodies were tested for binding to the preformed antibody-sortilin complex, example 8. Cross blocking between Sortilin antibodies from the same or different domains was determined by analyzing interference with antibody-Sortilin binding. Binding of antibodies to Sortilin-ECD-His was measured by BioLayer Interferometry using Octet 384RED as described previously. The left column indicates primary (immobilized) antibodies and the top row indicates the secondary antibodies (antibodies being tested against the immobilized antibodies). Binding of both the primary and secondary antibodies to Sortilin-ECD-His would results in a response value higher than 0.1 and indicate that both antibodies were binding to different regions of the protein. Response value less than 0.1 shows lack of binding of the secondary antibody and an effective cross blocking by the immobilized (primary) antibody, which suggests that both antibodies bind to the same region of Sortilin. 'x' indicates no binding and hence the antibodies block each other. 'b' indicates binding of both antibodies to sortilin and hence do not cross block each other. 22 out of 26 antibodies from E domain cross block all antibodies from the group and the remaining 4 antibodies cross block 20 out of 26 antibodies suggesting that most of the antibodies bind to the same region or in adjacent regions on sortilin.

Figure 1:
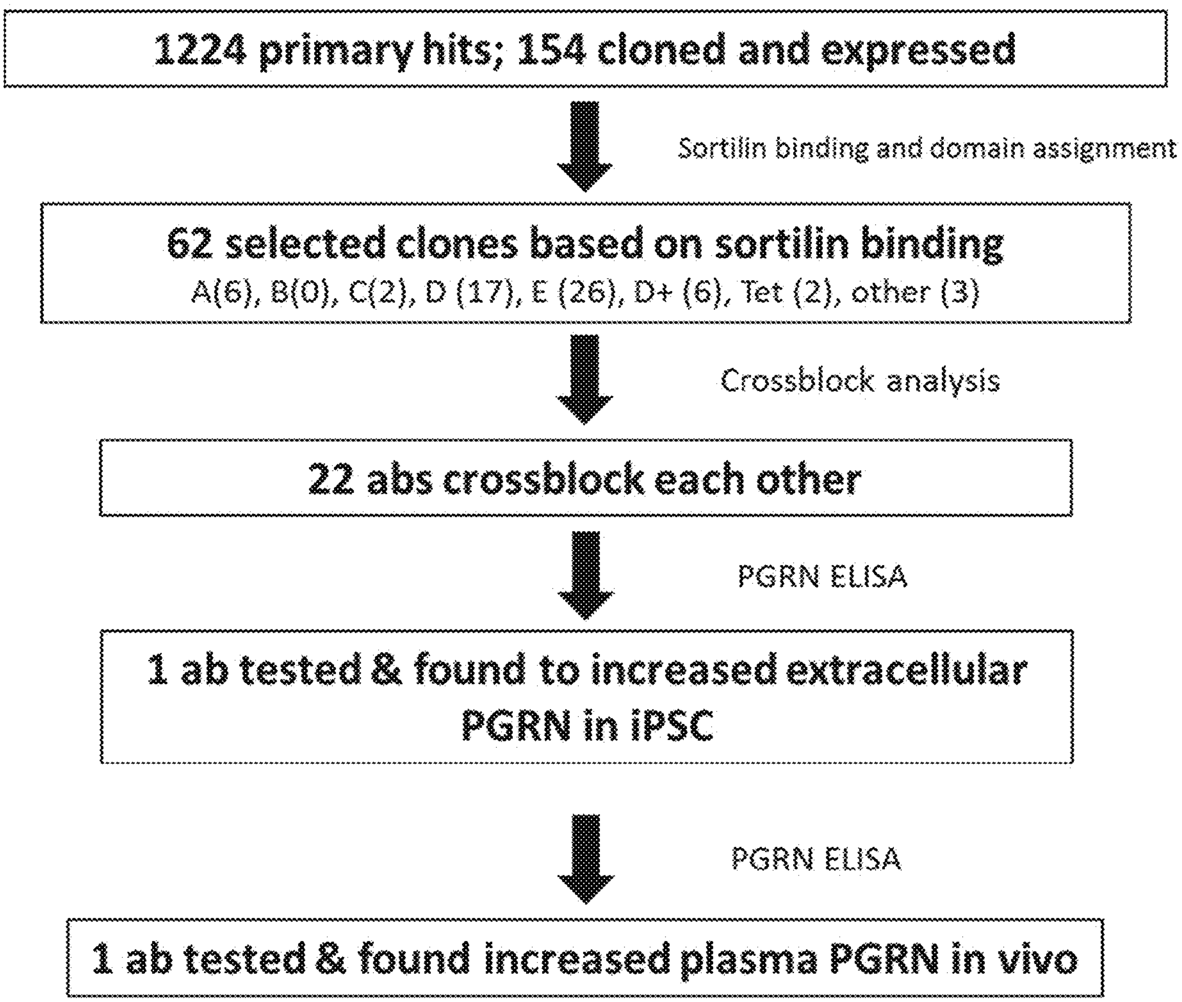
FIG. 1 illustrates steps in the selection of antibodies. A-E refer to the regions to which the respective Sortilin-binding antibodies were assigned based on shuffle constructs as described in Example 1 and SEQ ID Nos 147-155 "Other" refers to an antibody which could not be assigned to one region, and which may bind at the interface between the A- and B-regions. Tet refers to antibodies binding also tetraodonSortilin.

Mice were injected with 10 mg/kg of the test antibodies by subcutaneous administration. They were sacrificed after 48 hrs and blood samples were collected for analysis. Plasma PGRN was measured by ELISA. Data is presented as mean±SD. Data was analysed by t-test. *$p<0.001$ FIGS. 7A-7**B show the effects of Sortilin antibodies on extracellular PGRN in neuronal differentiated induced pluripotent stem cells (iPSCs) generated from an apparently heathy individual as well as from a PGRN R493X patient (Example 11)

FIGS. 8A-8F show representative peptides covering the conformational epitope of antibody 30. All of the shown peptides show a protection from exchange larger than 0.5D (Example 12).

DETAILED DESCRIPTION OF THE INVENTION

As used herein, the term "Sortilin" is synonymous with the Sortilin protein (identified in for example UniProt as Q99523, 1 and 2). The amino acid numbering of Sortilin is given with respect to SEQ ID NO:145 as shown below, Methionine (M) being amino acid 1:

MERPWGAADG LSRWPHGLGL LLLLQLLPPS TLSQDRLDAP PPPAAPLPRW SGPIGVSWGL RAAAAGGAFP RGGRWRRSAP GEDEECGRVR DFVAKLANNT HQHVFDDLRG SVSLSWVGDS TGVILVLTTF HVPLVIMTFG QSKLYRSEDY GKNFKDITDL INNTFIRTEF GMAIGPENSG KVVLTAEVSG GSRGGRIFRS SDFAKNFVQT DLPFHPLTQM MYSPQNSDYL LALSTENGLW VSKNFGGKWE EIHKAVCLAK WGSDNTIFFT TYANGSCKAD LGALELWRTS DLGKSFKTIG VKIYSFGLGG RFLFASVMAD KDTTRRIHVS TDQGDTWSMA QLPSVGQEQF YSILAANDDM VFMHVDEPGD TGFGTIFTSD DRGIVYSKSL DRHLYTTTGG ETDFTNVTSL RGVYITSVLS EDNSIQTMIT FDQGGRWTHL RKPENSECDA TAKNKNECSL HIHASYSISQ KLNVPMAPLS EPNAVGIVIA HGSVGDAISV MVPDVYISDD GGYSWTKMLE GPHYYTILDS GGIIVAIEHS SRP-INVIKFS TDEGQCWQTY TFTRDPIYFT GLASEP-GARS MNISIWGFTE SFLTSQWVSY TIDFKDILER NCEEKDYTIW LAHSTDPEDY EDGCILGYKE QFLRLRKSSV CONGRDYVVT KQPSICLCSL EDFLCDFGYY RPENDSKCVE QPELKGHDLE FCLYGREEHL TTNGYRKIPG DKCQGGVNPV REVKDLKKKC TSNFLSPEKQ NSKSNSVPII LAIVGLMLVT VVAGVLIVKK YVCGGRFLVH RYSVLQQHAE ANGVDGVDAL DTASHTNKSG YHDDSDEDLLE

As used herein, the term "E Region" is intended to refer to the region on Sortilin (corresponding to residues 612-753 of SEQ ID NO:145) consisting of the amino acids in SEQ ID NO:146 as shown below:

CEEKDYTIW LAHSTDPEDY EDGCILGYKEQ-FLRLRKSSVCQNGRDYVVT KQPSICLCSL EDFLCDFGYY RPENDSKCVE QPELKGHDL-EFCLYGREEHL TTNGYRKIPG DKCQGGVNPV REVKDLKKKC TSNFLSPEKQNSKSNS

For E region antibodies, binding to the following shuffle regions was observed: hsort, hB06-10, B12390, hB45678. The antibodies did not bind to hB01-05, and tetra.

PGRN gene (proepithelin, granulin-epithelin precursor, PC-cell-derived growth factor, acrogranin) encodes a 68.5 kDa secreted glycoprotein that has 7.5 repeats of smaller granulin motifs, ranging from 6-25 kDa, which can be proteolytically cleaved from the precursor PGRN (He, Z. & Bateman, A., J. Mol. Med. 81:600-6×2 (2003)). In non-neuronal cells, PGRN has been associated with a variety of events, such as cell cycle regulation and cell motility (He, Z. & Bateman, A., J. Mol. Med. 57:600-612 (2003); Monami, G., et ah, Cancer Res. (5(5:7103-7110 (2006)), wound repair, inflammation (Zhu, J., et ah, Cell 777:867-878 (2002)), induction of growth factors such as vascular endothelial growth factor (VEGF) (Tangkeangsittsin, W. & Serrero, G, Carcinogenesis 25.1587-1592 (2004)), and tumorigenesis (He, Z. & Bateman, A., J. Mol. Med. 81:600-612 (2003), Monami, G., et al., Cancer Res (5 (5:7103-7110 (2006); Serrero, G., Biochem Biophys. Res. Commun. 505-409-413 (2003), Lu, R & Serrero, G., Proc. Natl Acad Sa USA 98 142-147 (2001); Liau, L M., et al., Cancer Res. 60:1353-1360 (2000)).

PGRN mutations result in haploinsufficiency (Baker, M., et ah, Nature 442:916-919 (2006); Cruts, M., et ah, Nature 442:920-924 (2006)) and are known to be present in nearly 50% of familial FTD cases, making PGRN mutation a major genetic contributor to FTD (Cruts, M. & Van Broeckhoven, C, Trends Genet. 24:186-194 (2008); Le Ber, I., et ah, Brain 129:3051-3065 (2006)). The loss-of-function heterozygous character of PGRN mutations implies that in healthy individuals, PGRN expression plays a dose-dependent, critical role in protecting healthy individuals from the development of FTD.

The term "antibody" (Ab) in the context of the present invention refers to an immunoglobulin molecule or according to some embodiments of the invention, a fragment of an immunoglobulin molecule which has the ability to bind to an epitope of a molecule ("antigen"). Naturally occurring antibodies typically comprise a tetramer which is usually composed of at least two heavy (H) chains and at least two light (L) chains. Each heavy chain is comprised of a heavy chain variable domain (abbreviated herein as VH) and a heavy chain constant domain, usually comprised of three domains (CH1, CH2 and CH3). Heavy chains can be of any isotype, including IgG (IgG1, IgG2, IgG3 and IgG4 subtypes). Each light chain is comprised of a light chain variable domain (abbreviated herein as VL) and a light chain constant domain (CL). Light chains include kappa chains and lambda chains. The heavy and light chain variable domain is typically responsible for antigen recognition, while the heavy and light chain constant domain may mediate the binding of the immunoglobulin to host tissues or factors, including various cells of the immune system (e.g., effector cells) and the first component (C1q) of the classical complement system. The VH and VL domains can be further subdivided into regions of hypervariability, termed "complementarity determining regions," that are interspersed with domains of more conserved sequence, termed "framework regions" (FR). Each VH and VL is composed of three CDR Domains and four FR Domains arranged from amino-terminus to carboxy-terminus in the following order: FR1-CDR1-FR2-CDR2-FR3-CDR3-FR4. The variable domains of the heavy and light chains contain a binding domain that interacts with an antigen. Of particular relevance are antibodies and their antigen-binding fragments that have been "isolated" so as to exist in a physical milieu distinct from that in which it may occur in nature or that have been modified so as to differ from a naturally occurring antibody in amino acid sequence.

The term "epitope" means an antigenic determinant capable of specific binding to an antibody. Epitopes usually consist of surface groupings of molecules such as amino acids or sugar side chains and usually have specific three dimensional structural characteristics, as well as specific charge characteristics. Conformational and linear epitopes are distinguished in that the binding to the former, but not the latter, is always lost in the presence of denaturing solvents. The epitope may comprise amino acid residues directly involved in the binding and other amino acid residues, which are not directly involved in the binding, such as amino acid residues which are effectively blocked by the specifically antigen-binding peptide (in other words, the amino acid residue is within the footprint of the specifically antigen-binding peptide).

As used herein, the term "antigen-binding fragment of an antibody" means a fragment, portion, region or domain of an antibody (regardless of how it is produced (e.g., via cleavage, recombinantly, synthetically, etc.)) that is capable of binding to an epitope, and thus the term "antigen-binding" is intended to mean the same as "epitope-binding" so that, for example, an "antigen-binding fragment of an antibody" is intended to be the same as an "epitope-binding fragment of an antibody". An antigen-binding fragment may contain 1, 2, 3, 4, 5 or all 6 of the CDR Domains of such antibody and, although capable of binding to such epitope, may exhibit a specificity, affinity or selectivity toward such epitope that differs from that of such antibody. Preferably, however, an antigen-binding fragment will contain all 6 of the CDR Domains of such antibody. An antigen-binding fragment of an antibody may be part of, or comprise, a single polypeptide chain (e.g., an scFv), or may be part of, or comprise, two or more polypeptide chains, each having an amino-terminus and a carboxyl terminus (e.g., a diabody, a Fab fragment, a $Fab_2$ fragment, etc.). Fragments of antibodies that exhibit antigen-binding ability can be obtained, for example, by protease cleavage of intact antibodies. More preferably, although the two domains of the Fv fragment, VL and VH, are naturally encoded by separate genes, or polynucleotides that encode such gene sequences (e.g., their encoding cDNA) can be joined, using recombinant methods, by a flexible linker that enables them to be made as a single protein chain in which the VL and VH regions associate to form monovalent antigen-binding molecules (known as single-chain Fv (scFv); see e.g., Bird et al., (1988) Science 242:423-426; and Huston et al. (1988) Proc. Natl. Acad. Sci. (U.S.A.) 85:5879-5883). Alternatively, by employing a flexible linker that is too short (e.g., less than about 9 residues) to enable the VL and VH domains of a single polypeptide chain to associate together, one can form a bispecific antibody, diabody, or similar molecule (in which two such polypeptide chains associate together to form a bivalent antigen-binding molecule) (see for instance PNAS USA 90 (14), 6444-8 (1993) for a description of diabodies). Examples of antigen-binding fragments encompassed within the present invention include (i) a Fab' or Fab fragment, a monovalent fragment consisting of the VL, VH, CL and CH1 domains, or a monovalent antibody as described in WO2007059782; (ii) F(ab')2 fragments, bivalent fragments comprising two Fab fragments linked by a disulfide bridge at the hinge domain; (iii) an Fd fragment consisting essentially of the VH and CH1 domains; (iv) a Fv fragment consisting essentially of a VL and VH domains, (v) a dAb fragment (Ward et al., Nature 341, 544-546 (1989)), which consists essentially of a VH domain and also called domain antibodies (Holt et al; Trends Biotechnol. 2003 November; 2i (II): 484-90); (vi) camelid or nanobodies (Revets et al; Expert Opin Biol Ther. 2005 January; 5_(I): III-24) and (vii) an isolated complementarity determining region (CDR). Furthermore, although the two domains of the Fv fragment, VL and VH, are coded for by separate genes, they may be joined, using recombinant methods, by a synthetic linker that enables them to be made as a single protein chain in which the VL and VH domains pair to form monovalent molecules (known as single chain antibodies or single chain Fv (scFv), see for instance Bird et al., Science 242, 423-426 (1988) and Huston et al., PNAS USA 85, 5879-5883 (1988)). These and other useful antibody fragments in the context of the present invention are discussed further herein.

It also should be understood that the term antibody, unless specified otherwise, also includes antibody-like polypeptides, such as chimeric antibodies and humanized antibodies, and antibody fragments retaining the ability to bind to the antigen (antigen-binding fragments) provided by any known technique, such as enzymatic cleavage, peptide synthesis, and recombinant techniques. An antibody as generated can possess any isotype. As used herein, "isotype" refers to the immunoglobulin class (for instance IgG1, IgG2, IgG3 or IgG4) that is encoded by heavy chain constant domain genes. Such antibody fragments are obtained using conventional techniques known to those of skill in the art; suitable fragments capable of binding to a desired epitope may be readily screened for utility in the same manner as an intact antibody.

The term "bispecific antibody" refers to an antibody containing two independent antigen-binding fragments that each target independent targets. These targets can be epitopes present on different proteins or different epitopes present on the same target. Bispecific antibody molecules can be made using compensatory amino acid changes in the constant domains of the HCs of the parent monospecific bivalent antibody molecules. The resulting heterodimeric antibody contains one Fabs contributed from two different parent monospecific antibodies. Amino acid changes in the Fc domain leads to increased stability of the heterodimeric antibody with bispecificity that is stable over time. (Ridgway et al., Protein Engineering 9, 617-621 (1996), Gunasekaran et al., JBC 285, 19637-1 (2010), Moore et al., MAB 3:6 546-557 (2011), Strop et al., JMB 420, 204-219 (2012), Metz et al., Protein Engineering 25:10 571-580 (2012), Labrijn et al., PNAS 110:113, 5145-5150 (2013), Spreter Von Kreudenstein et al., MAB 5:5 646-654 (2013)). Bispecific antibodies can also include molecules that are generated using ScFv fusions. Two monospecific scfv are then independently joined to Fc domains able to form stable heterodimers to generate a single bispecific molecule (Mabry et al., PEDS 23:3 115-127 (2010). Bispecific molecules have dual binding capabilities.

An "anti-Sortilin antibody" or "Sortilin antibody" (used interchangeably herein, depending on the context wherein its written) is an antibody an antigen-binding fragment thereof which binds specifically to Sortilin, and especially to the Sortilin E Region, SEQ ID NO:146. An anti-Sortilin antibody that binds to the Sortilin E Region will usually bind to a conformational epitope or a linear epitope of 1, 2, 3, 4, 5, 6 or 7 consecutive amino acids within the E-Region with an affinity (IC50) at or below 22 nM, such as between 22 nM and 1 nM, between 10 nM and 1 nM or between 5 nM and 1 nM or even higher such as about 1 μM or 1 to 5 μM.

The term "human antibody" (which may be abbreviated to "humAb" or "HuMab"), as used herein, is intended to include antibodies having variable and constant domains derived from human germline immunoglobulin sequences. The human antibodies of the invention may include amino acid residues not encoded by human germline immunoglobulin sequences (e.g., mutations introduced by random or site-specific mutagenesis in vitro or during gene rearrangement or by somatic mutation in vivo).

The terms "monoclonal antibody" or "monoclonal antibody composition" as used herein refer to a preparation of antibody molecules of single molecular composition. A conventional monoclonal antibody composition displays a single binding specificity and affinity for a particular epitope. In certain embodiments a monoclonal antibody can be composed of more than one Fab domain thereby increasing the specificity to more than one target. The terms "monoclonal antibody" or "monoclonal antibody composition" are not intended to be limited by any particular method of production (e.g., recombinant, transgenic, hybridoma, etc.).

The term "antibody XX" is intended to denote an antibody or antigen-binding fragment thereof (for example antibody "6003-056"), comprising or consisting of the Light Chain, the Light Chain Variable domain, or the Light Chain Variable domain CDR1-3, as defined by its respective SEQ ID NO, and the Heavy Chain, Heavy Chain Variable Domain, or Heavy Chain Variable Domain CDR1-3 as defined by its respective SEQ ID NO. In certain embodiments the antibody or antigen-binding fragment thereof are defined by their entire Heavy Chain Variable Domain comprising as defined by their SEQ ID NO and their Light Chain Variable Domain as defined by their SEQ ID NO.

The numbering of amino acid residues can be performed by IMGT®, the international ImMunoGeneTics information System® or, Kabat, E. A., Wu, T. T., Perry, H. M., Gottesmann, K. S. & Foeller, C. (1991). Sequences of Proteins of Immunological Interest, 5th edit., NIH Publication no. 91-3242 U.S. Department of Health and Human Services; Chothia, C. & Lesk, A. M. (1987), or Canonical structures For The Hypervariable domains Of Immunoglobulins. J. Mol. Biol. 196, 901-917.

As used herein, an antibody or an antigen-binding fragment thereof is said to "specifically" bind a region of another molecule (i.e., an epitope) if it reacts or associates more frequently, more rapidly, with greater duration and/or with greater affinity or avidity with that epitope relative to alternative epitopes. In one embodiment, the antibody, or antigen-binding fragment thereof, of the invention binds at least 10-fold more strongly to its target (Sortilin) than to another molecule; preferably at least 50-fold more strongly and more preferably at least 100-fold more strongly. Preferably, the antibody, or antigen-binding fragment thereof, binds under physiological conditions, for example, in vivo. Thus, by "specifically binding to Sortilin", we include the ability of the antibody, or antigen-binding fragment thereof, to bind to Sortilin with such specificity and/or under such conditions. Methods suitable for determining such binding will be known to those skilled in the art, and exemplary methods are described in the accompanying Examples. As used herein, the term "binding" in the context of the binding of an antibody to a predetermined antigen typically refers to binding with an affinity corresponding to a KD of about $10^{-7}$ M or less, such as about $10^{-8}$ M or less, such as about $10^{-9}$ M or less when determined by for instance surface plasmon resonance (SPR) technology in either a BIAcore® 3000 or T200 instrument using the antigen as the ligand and the antibody as the analyte, and binds to the predetermined antigen with an affinity corresponding to a KD that is at least ten-fold lower, such as at least 100 fold lower, for instance at least 1,000 fold lower, such as at least 10,000 fold lower, for instance at least 100,000 fold lower than its affinity for binding to a non-specific antigen (e.g., BSA, casein) other than the predetermined antigen or a closely-related antigen. The amount with which the affinity is lower is dependent on the KD of the antibody, so that when the KD of the antibody is very low (that is, the antibody is highly specific), then the amount with which the affinity for the antigen is lower than the affinity for a non-specific antigen may be at least 10,000 fold. In particular, the invention pertains to anti-Sortilin antibodies that exhibit a binding affinity corresponding to at or below 22 nM, such as between 22 nM and 1 nM, between 10 nM and 1 nM or between 5 nM and 1 nM, when determined by, for instance, bioLayer interferometry using an Octet 384RED (Example 7).

In certain embodiments of the invention the invention relates to an antibody or antigen-binding fragment thereof able to compete with humAb antibody 30 or humAb antibody 900 for binding to Sortilin. In another embodiment the invention relates to an antibody or antigen-binding fragment thereof that is able to compete with antibody 30 for binding to the E region of Sortilin as defined in SEQ ID NO: 146. Such competitive binding inhibition can be determined using assays and methods well known in the art, for example using BIAcore® chips with immobilised human Sortilin and incubating with a reference antibody (such as antibody "30" or "900") with and without an antibody polypeptide to be tested. Alternatively, a pairwise mapping approach can be used, in which a reference antibody (such as antibody "30" or "900") is immobilised to the surface of the BIAcore® chip, human Sortilin antigen is bound to the immobilised antibody, and then a second antibody is tested for simultaneous binding ability to human Sortilin (see 'BIAcore® Assay Handbook', GE Healthcare Life Sciences, 29-0194-00 AA 05/2012; the disclosures of which are incorporated herein by reference). Alternatively, use of Octet 384Red (Example 7 & 8) or a similar approach to demonstrate competitive binding.

The term "kd" (sec−1 or 1/s), as used herein, refers to the dissociation rate constant of a particular antibody-antigen interaction. Said value is also referred to as the koff value.

The term "ka" (M−1×sec−1 or 1/Msec), as used herein, refers to the association rate constant of a particular antibody-antigen interaction.

The term "KD" (M), as used herein, refers to the dissociation equilibrium constant of a particular antibody-antigen interaction and is obtained by dividing the kd by the ka.

The term "KA" (M−1 or 1/M), as used herein, refers to the association equilibrium constant of a particular antibody-antigen interaction and is obtained by dividing the ka by the kd.

In one embodiment, the invention relates to an antibody, or antigen-binding fragment thereof, which exhibits one or more of the following properties:

(i) a binding affinity ($K_D$) for Sortilin of between 0.5-10 nM, such as 1-5 nM or 1-2 nM;
(ii) capability to reduce and/or inhibit clearance of PGRN by Sortilin-expressing cells;
(iii) capability to reduce and/or inhibit the endocytosis of PGRN by Sortilin-expressing cells;
(iv) capability to increase the amount and/or concentration of PGRN in the plasma in human-Sortilin-expressing knock-in mice.

The term "capability to reduce and/or inhibit clearance of PGRN by Sortilin-expressing cells" includes the ability to increase the concentration of PGRN in the medium by at least 20%, such as between 25% and 500%, between 25% and 400% or between 25% and 200% as measured by an ELISA assay as disclosed in Example 9.

The "capability to increase the amount and/or concentration of PGRN in the plasma in human-Sortilin-expressing knock-in mice" includes the ability to increase the concentration of PGRN in the plasma by at least 25% but preferably between 50 and 500 percent as measured by an ELISA assay as disclosed in Example 10.

In some antibodies, only part of a CDR, namely the subset of CDR residues required for binding, termed the SDRs, are needed to retain binding in a humanized antibody. CDR residues not contacting the relevant epitope and not in the SDRs can be identified based on previous studies (for example residues H60-H65 in CDR H2 are often not required), from regions of Kabat CDRs lying outside Chothia hypervariable loops (see, Kabat et al. (1992) SEQUENCES OF PROTEINS OF IMMUNOLOGICAL INTEREST, National Institutes of Health Publication No. 91-3242; Chothia, C. et al. (1987) "*Canonical Structures For The Hypervariable Regions Of Immunoglobulins*," J. Mol. Biol. 196:901-917), by molecular modeling and/or empirically, or as described in Gonzales, N. R. et al. (2004) "*SDR Grafting Of A Murine Antibody Using Multiple Human Germline Templates To Minimize Its Immunogenicity*," Mol. Immunol. 41:863-872. In such humanized antibodies at positions in which one or more donor CDR residues is absent or in which an entire donor CDR is omitted, the amino acid occupying the position can be an amino acid occupying the corresponding position (by Kabat numbering) in the acceptor antibody sequence. The number of such substitutions of acceptor for donor amino acids in the CDRs to include reflects a balance of competing considerations. Such substitutions are potentially advantageous in decreasing the number of mouse amino acids in a humanized antibody and consequently decreasing potential immunogenicity. However, substitutions can also cause changes of affinity, and significant reductions in affinity are preferably avoided. Positions for substitution within CDRs and amino acids to substitute can also be selected empirically.

(Eddy, S. R. (2004) "*Where Did The BLOSUM62 Alignment Score Matrix Come From?*," Nature Biotech. 22(8):1035-1036; Henikoff, J. G. (1992) "Amino acid substitution matrices from protein blocks," Proc. Natl. Acad. Sci. (USA) 89:10915-10919; Karlin, S. et al. (1990) "*Methods For Assessing The Statistical Significance Of Molecular Sequence Features By Using General Scoring Schemes*," Proc. Natl. Acad. Sci. (USA) 87:2264-2268; Altschul, S. F. (1991) "*Amino Acid Substitution Matrices From An Information Theoretic Perspective*," J. Mol. Biol. 219, 555-565. Currently, the most advanced BLOSUM database is the BLOSUM62 database (BLOSUM62.iij). Table 1 presents the BLOSUM62.iij substitution scores (the higher the score the more conservative the substitution and thus the more likely the substitution will not affect function). If an antigen-binding fragment comprising the resultant CDR fails to bind to Sortilin, for example, then the BLOSUM62.iij substitution score is deemed to be insufficiently conservative, and a new candidate substitution is selected and produced having a higher substitution score. Thus, for example, if the original residue was glutamate (E), and the non-functional substitute residue was histidine (H), then the BLOSUM62.iij substitution score will be 0, and more conservative changes (such as to aspartate, asparagine, glutamine, or lysine) are preferred.

TABLE 1

| | A | R | N | D | C | Q | E | G | H | I | L | K | M | F | P | S | T | W | Y | V |
|---|---|---|---|---|---|---|---|---|---|---|---|---|---|---|---|---|---|---|---|---|
| A | +4 | −1 | −2 | −2 | 0 | −1 | −1 | 0 | −2 | −1 | −1 | −1 | −1 | −2 | −1 | +1 | 0 | −3 | −2 | 0 |
| R | −1 | +5 | 0 | −2 | −3 | +1 | 0 | −2 | 0 | −3 | −2 | +2 | −1 | −3 | −2 | −1 | −1 | −3 | −2 | −3 |
| N | −2 | 0 | +6 | +1 | −3 | 0 | 0 | 0 | +1 | −3 | −3 | 0 | −2 | −3 | −2 | +1 | 0 | −4 | −2 | −3 |
| D | −2 | −2 | +1 | +6 | −3 | 0 | +2 | −1 | −1 | −3 | −4 | −1 | −3 | −3 | −1 | 0 | −1 | −4 | −3 | −3 |
| C | 0 | −3 | −3 | −3 | +9 | −3 | −4 | −3 | −3 | −1 | −1 | −3 | −1 | −2 | −3 | −1 | −1 | −2 | −2 | −1 |
| Q | −1 | +1 | 0 | 0 | −3 | +5 | +2 | −2 | 0 | −3 | −2 | +1 | 0 | −3 | −1 | 0 | −1 | −2 | −1 | −2 |
| E | −1 | 0 | 0 | +2 | −4 | +2 | +5 | −2 | 0 | −3 | −3 | +1 | −2 | −3 | −1 | 0 | −1 | −3 | −2 | −2 |
| G | 0 | −2 | 0 | −1 | −3 | −2 | −2 | +6 | −2 | −4 | −4 | −2 | −3 | −3 | −2 | 0 | −2 | −2 | −3 | −3 |
| H | −2 | 0 | +1 | −1 | −3 | 0 | 0 | −2 | +8 | −3 | −3 | −1 | −2 | −1 | −2 | −1 | −2 | −2 | +2 | −3 |
| I | −1 | −3 | −3 | −3 | −1 | −3 | −3 | −4 | −3 | +4 | +2 | −3 | +1 | 0 | −3 | −2 | −1 | −3 | −1 | +3 |
| L | −1 | −2 | −3 | −4 | −1 | −2 | −3 | −4 | −3 | +2 | +4 | −2 | +2 | 0 | −3 | −2 | −1 | −2 | −1 | +1 |
| K | −1 | +2 | 0 | −1 | −3 | +1 | +1 | −2 | −1 | −3 | −2 | +5 | −1 | −3 | −1 | 0 | −1 | −3 | −2 | −2 |
| M | −1 | −1 | −2 | −3 | −1 | 0 | −2 | −3 | −2 | +1 | +2 | −1 | +5 | 0 | −2 | −1 | −1 | −1 | −1 | +1 |
| F | −2 | −3 | −3 | −3 | −2 | −3 | −3 | −3 | −1 | 0 | 0 | −3 | 0 | +6 | −4 | −2 | −2 | +1 | +3 | −1 |
| P | −1 | −2 | −2 | −1 | −3 | −1 | −1 | −2 | −2 | −3 | −3 | −1 | −2 | −4 | +7 | −1 | −1 | −4 | −3 | −2 |
| S | +1 | −1 | +1 | 0 | −1 | 0 | 0 | 0 | −1 | −2 | −2 | 0 | −1 | −2 | −1 | +4 | +1 | −3 | −2 | −2 |
| T | 0 | −1 | 0 | −1 | −1 | −1 | −1 | −2 | −2 | −1 | −1 | −1 | −1 | −2 | −1 | +1 | +5 | −2 | −2 | 0 |
| W | −3 | −3 | −4 | −4 | −2 | −2 | −3 | −2 | −2 | −3 | −2 | −3 | −1 | +1 | −4 | −3 | −2 | +11 | +2 | −3 |
| Y | −2 | −2 | −2 | −3 | −2 | −1 | −2 | −3 | +2 | −1 | −1 | −2 | −1 | +3 | −3 | −2 | −2 | +2 | +7 | −1 |
| V | 0 | −3 | −3 | −3 | −1 | −2 | −2 | −3 | −3 | +3 | +1 | −2 | +1 | −1 | −2 | −2 | 0 | −3 | −1 | +4 |

The fact that a single amino acid alteration of a CDR residue can result in loss of functional binding (Rudikoff, S, etc. (1982) "*Single Amino Acid Substitution Altering Antigen-binding Specificity*," Proc. Natl. Acad. Sci. (USA) 79(6):1979-1983) provides a means for systematically identifying alternative functional CDR sequences. In one preferred method for obtaining such variant CDRs, a polynucleotide encoding the CDR is mutagenized (for example via random mutagenesis or by a site-directed method (e.g., polymerase chain-mediated amplification with primers that encode the mutated locus)) to produce a CDR having a substituted amino acid residue. By comparing the identity of the relevant residue in the original (functional) CDR sequence to the identity of the substituted (nonfunctional) variant CDR sequence, the BLOSUM62.iij substitution score for that substitution can be identified. The BLOSUM system provides a matrix of amino acid substitutions created by analyzing a database of sequences for trusted alignments The invention thus contemplates the use of random mutagenesis to identify improved CDRs. In the context of the present invention, conservative substitutions may be defined by substitutions within the classes of amino acids reflected in one or more of the following three tables:

Amino Acid Residue Classes for Conservative Substitutions:

TABLE 2

| | |
|---|---|
| Acidic Residues | Asp (D) and Glu (E) |
| Basic Residues | Lys (K), Arg (R), and His (H) |
| Hydrophilic Uncharged Residues | Ser (S), Thr (T), Asn (N), and Gln (Q) |
| Aliphatic Uncharged Residues | Cly (G), Ala (A), Val (V), Leu (L), and Ile (I) |
| Non-polar Uncharged Residues | Cys (C), Met (M), and Pro (P) |
| Aromatic Residues | Phe (F), Tyr (Y), and Trp (W) |

Alternative Conservative Amino Acid Residue Substitution Classes:

TABLE 3

| | | | |
|---|---|---|---|
| 1 | A | S | T |
| 2 | D | E | |
| 3 | N | Q | |
| 4 | R | K | |
| 5 | I | L | M |
| 6 | F | Y | W |

Alternative Physical and Functional Classifications of Amino Acid Residues:

TABLE 4

| | |
|---|---|
| Alcohol Group-Containing Residues | S and T |
| Aliphatic Residues | I, L, V and M |
| Cycloalkenyl-Associated Residues | F, H, W and Y |
| Hydrophobic Residues | A, C, F, G, H, I, L, M, R, T, V, W and Y |
| Negatively Charged Residues | D and E |
| Polar Residues | C, D, E, H, K, N, Q, R, S and T |
| Positively Charged Residues | H, K and R |
| Small Residues | A, C, D, G, N, P, S, T and V |
| Very Small Residues | A, G and S |
| Residues Involved In Turn Formation | A, C, D, E, G, H, K, N, Q, R, S, P and T |
| Flexible Residues | Q, T, K, S, G, P, D, E and R |

More conservative substitutions groupings include: valine-leucine-isoleucine, phenylalanine-tyrosine, lysine-arginine, alanine-valine, and asparagine-glutamine.

Additional groups of amino acids may also be formulated using the principles described in, e.g., Creighton (1984) Proteins: Structure and Molecular Properties (2d Ed. 1993), W. H. Freeman and Company.

Phage display technology can alternatively be used to increase (or decrease) CDR affinity. This technology, referred to as affinity maturation, employs mutagenesis or "CDR walking" and re-selection uses the target antigen or an antigenic antigen-binding fragment thereof to identify antibodies having CDRs that bind with higher (or lower) affinity to the antigen when compared with the initial or parental antibody (See, e.g. Glaser et al. (1992) J. Immunology 149:3903). Mutagenizing entire codons rather than single nucleotides results in a semi-randomized repertoire of amino acid mutations. Libraries can be constructed consisting of a pool of variant clones each of which differs by a single amino acid alteration in a single CDR and which contain variants representing each possible amino acid substitution for each CDR residue. Mutants with increased (or decreased) binding affinity for the antigen can be screened by contacting the immobilized mutants with labeled antigen. Any screening method known in the art can be used to identify mutant antibodies with increased or decreased affinity to the antigen (e.g., ELISA) (See Wu et al. 1998, Proc. Natl. Acad. Sci. (U.S.A.) 95:6037; Yelton et al., 1995, J. Immunology 155:1994). CDR walking which randomizes the Light Chain may be used possible (see, Schier et al., 1996, J. Mol. Bio. 263:551).

Methods for accomplishing such affinity maturation are described for example in: Krause, J. C. et al. (2011) "*An Insertion Mutation That Distorts Antibody Binding Site Architecture Enhances Function Of A Human Antibody*," MBio. 2 (1) pii: e00345-10. doi: 10.1128/mBio.00345-10; Kuan, C. T. et al. (2010) "*Affinity-Matured Anti-Glycoprotein NMB Recombinant Immunotoxins Targeting Malignant Gliomas And Melanomas*," Int. J. Cancer 10.1002/ijc.25645; Hackel, B. J. et al. (2010) "*Stability And CDR Composition Biases Enrich Binder Functionality Landscapes*," J. Mol. Biol. 401(1):84-96; Montgomery, D. L. et al. (2009) "*Affinity Maturation And Characterization Of A Human Monoclonal Antibody Against HIV-1 gp41*," MAntibodies 1(5):462-474; Gustchina, E. et al. (2009) "*Affinity Maturation By Targeted Diversification Of The CDR-H2 Loop Of A Monoclonal Fab Derived From A Synthetic Naïve Human Antibody Library And Directed Against The Internal Trimeric Coiled-Coil Of Gp41 Yields A Set Of Fantibodies With Improved HIV-1 Neutralization Potency And Breadth*," Virology 393(1):112-119; Finlay, W. J. et al. (2009) "*Affinity Maturation Of A Humanized Rat Antibody For Anti-RAGE Therapy: Comprehensive Mutagenesis Reveals A High Level Of Mutational Plasticity Both Inside And Outside The Complementarity-Determining Regions*," J. Mol. Biol. 388(3):541-558; Bostrom, J. et al. (2009) "*Improving Antibody Binding Affinity And Specificity For Therapeutic Development*," Methods Mol. Biol. 525:353-376; Steidl, S. et al. (2008) "*In Vitro Affinity Maturation Of Human GM-CSF Antibodies By Targeted CDR-Diversification*," Mol. Immunol. 46(1):135-144; and Barderas, R. et al. (2008) "*Affinity Maturation Of Antibodies Assisted By In Silico Modeling*," Proc. Natl. Acad. Sci. (USA) 105(26):9029-9034.

Thus, the sequence of CDR variants of encompassed antibodies or their antigen-binding fragments may differ from the sequence of the CDR of the parent antibody through substitutions; for instance substituted 4 amino acid residue, 3 amino acid residue, 2 amino acid residue or 1 of the amino acid residues. According to an embodiment of the invention it is furthermore envisaged that the amino acids in the CDR regions may be substituted with conservative substitutions, as defined in the above 3 tables.

The term "transgenic non-human animal" refers to a non-human animal having a genome comprising one or more human heavy and/or light chain transgenes or trans-chromosomes (either integrated or non-integrated into the animal's natural genomic DNA) and which is capable of expressing fully human antibodies. For example, a transgenic mouse can have a human light chain transgene and either a human heavy chain transgene or human heavy chain transchromosome, such that the mouse produces human anti-Sortilin antibody when immunized with Sortilin antigen and/or cells expressing Sortilin. The human heavy chain transgene may be integrated into the chromosomal DNA of the mouse, as is the case for transgenic mice, for instance HuMAb mice, such as HCo7 or HCo12 mice, or the human heavy chain transgene may be maintained extra-chromosomally, as is the case for trans-chromosomal KM mice as described in WO02/43478. Such transgenic and trans-chromosomal mice (collectively referred to herein as "transgenic mice") are capable of producing multiple isotypes of human monoclonal antibodies to a given antigen (such as IgG, IgA, IgM, IgD and/or IgE) by undergoing V-D-J recombination and isotype switching.

Transgenic, nonhuman animals can also be used for production of antibodies against a specific antigen by introducing genes encoding such specific antibody, for example by operatively linking the antibody genes to a gene encoding a protein, which is expressed in the milk of the animal.

The term "treatment" or "treating" as used herein means ameliorating, slowing, attenuating or reversing the progress or severity of a disease or disorder, or ameliorating, slowing, attenuating or reversing one or more symptoms or side effects of such disease or disorder. For purposes of this invention, "treatment" or "treating" further means an approach for obtaining beneficial or desired clinical results, where "beneficial or desired clinical results" include, without limitation, alleviation of a symptom, diminishment of the extent of a disorder or disease, stabilized (i.e., not worsening) disease or disorder state, delay or slowing of the progression a disease or disorder state, amelioration or palliation of a disease or disorder state, and remission of a disease or disorder, whether partial or total detectable or undetectable.

An "effective amount," when applied to an antibody or antigen-binding fragment thereof of the invention, refers to an amount sufficient, at dosages and for periods of time necessary, to achieve an intended biological effect or a desired therapeutic result including, without limitation, clinical results. The phrase "therapeutically effective amount," when applied to an antibody or antigen-binding fragment thereof of the invention, is intended to denote an amount of the antibody, or antigen-binding fragment thereof, that is sufficient to ameliorate, palliate, stabilize, reverse, slow, attenuate or delay the progression of a disorder or disease state, or of a symptom of the disorder or disease. In an embodiment, the method of the present invention provides for administration of the antibody, or antigen-binding fragment thereof, in combinations with other compounds. In such instances, the "effective amount" is the amount of the combination sufficient to cause the intended biological effect.

A therapeutically effective amount of an anti-Sortilin antibody or antigen-binding fragment thereof of the invention may vary according to factors such as the disease state, age, sex, and weight of the individual, and the ability of the anti-Sortilin antibody or antigen-binding fragment thereof to elicit a desired response in the individual. A therapeutically effective amount is also one in which any toxic or detrimental effects of the antibody or antibody portion are outweighed by the therapeutically beneficial effects.

The antibodies of the present invention are preferably a human or humanized antibody.

The numbering of amino acid residues in this region can be performed using for example IMGT®, the international ImMunoGeneTics information System® or, Kabat, E. A., Wu, T. T., Perry, H. M., Gottesmann, K. S. & Foeller, C. (1991). Sequences of Proteins of Immunological Interest, 5th edit., NIH Publication no. 91-3242 U.S. Department of Health and Human Services; Chothia, C. & Lesk, A. M. (1987), or Canonical structures For The Hypervariable domains Of Immunoglobulins. J. Mol. Biol. 196, 901-917.

Antibody 6003-028:

Accordingly, the invention relates to an antibody, or an antigen-binding fragment thereof, comprising or consisting of:

(a) a heavy Chain CDR1 having the amino acid sequence of SEQ ID NO:1;
(b) a Heavy Chain CDR2 having the amino acid sequence of SEQ ID NO:2;
(c) a Heavy Chain CDR3 having the amino acid sequence of SEQ ID NO:3;
(d) a light Chain CDR1 having the amino acid sequence of SEQ ID NO:4;
(e) a light Chain CDR2 having the amino acid sequence of SEQ ID NO:5; and
(f) a light Chain CDR3 having the amino acid sequence of SEQ ID NO:6.

Preferably, the monoclonal antibody may comprise or consist of the heavy chain variable domain of SEQ ID NO:109 and the light chain variable domain of SEQ ID NO:110.

Antibody 6003-056:

Accordingly, the invention relates to an antibody, or an antigen-binding fragment thereof, comprising or consisting of:

a. a heavy chain variable domain CDR1 comprising SEQ ID NO:7;
b. a heavy chain variable domain CDR 2 comprising SEQ ID NO:8;
c. a heavy chain variable domain CDR 3 comprising SEQ ID NO:9;
d. a light chain variable domain CDR 1 comprising SEQ ID NO:10;
e. a light chain variable domain CDR 2 comprising SEQ ID NO:11; and
f. a light chain variable domain CDR 3 comprising SEQ ID NO:12.

Preferably, the monoclonal antibody may comprise or consist of the heavy chain variable domain of SEQ ID NO:111 and the light chain variable domain of SEQ ID NO:112.

Antibody 6003-1286:

Accordingly, the invention relates to an antibody, or an antigen-binding fragment thereof, comprising or consisting of:

a. a heavy chain variable domain CDR1 comprising SEQ ID NO:13;
b. a heavy chain variable domain CDR 2 comprising SEQ ID NO:14;
c. a heavy chain variable domain CDR 3 comprising SEQ ID NO:15;
d. a light chain variable domain CDR 1 comprising SEQ ID NO:16;
e. a light chain variable domain CDR 2 comprising SEQ ID NO:17; and
f. a light chain variable domain CDR 3 comprising SEQ ID NO:18.

Preferably, the monoclonal antibody may comprise or consist of the heavy chain variable domain of SEQ ID NO:113 and the light chain variable domain of SEQ ID NO:114.

Antibody 6003-030:

Accordingly, the invention relates to an antibody, or an antigen-binding fragment thereof, comprising or consisting of:

a. a heavy chain variable domain CDR1 comprising SEQ ID NO:19;
b. a heavy chain variable domain CDR 2 comprising SEQ ID NO:20;
c. a heavy chain variable domain CDR 3 comprising SEQ ID NO:21;
d. a light chain variable domain CDR 1 comprising SEQ ID NO:22;
e. a light chain variable domain CDR 2 comprising SEQ ID NO:23; and
f. a light chain variable domain CDR 3 comprising SEQ ID NO:24.

Preferably, the monoclonal antibody may comprise or consist of the heavy chain variable domain of SEQ ID NO:115 and the light chain variable domain of SEQ ID NO:116.

Antibody 6003-1277:

Accordingly, the invention relates to an antibody, or an antigen-binding fragment thereof, comprising or consisting of:

a. a heavy chain variable domain CDR1 comprising SEQ ID NO:25;
b. a heavy chain variable domain CDR 2 comprising SEQ ID NO:26;

c. a heavy chain variable domain CDR 3 comprising SEQ ID NO:27;
d. a light chain variable domain CDR 1 comprising SEQ ID NO:28;
e. a light chain variable domain CDR 2 comprising SEQ ID NO:29; and
f. a light chain variable domain CDR 3 comprising SEQ ID NO:30.

Preferably, the monoclonal antibody may comprise or consist of the heavy chain variable domain of SEQ ID NO:117 and the light chain variable domain of SEQ ID NO:118.

Antibody 6003-381:

Accordingly, the invention relates to an antibody, or an antigen-binding fragment thereof, comprising or consisting of:

a. a heavy chain variable domain CDR1 comprising SEQ ID NO:31;
b. a heavy chain variable domain CDR 2 comprising SEQ ID NO:32;
c. a heavy chain variable domain CDR 3 comprising SEQ ID NO:33;
d. a light chain variable domain CDR 1 comprising SEQ ID NO:34;
e. a light chain variable domain CDR 2 comprising SEQ ID NO:35; and
f. a light chain variable domain CDR 3 comprising SEQ ID NO:36.

Preferably, the monoclonal antibody may comprise or consist of the heavy chain variable domain of SEQ ID NO:119 and the light chain variable domain of SEQ ID NO:120.

Antibody 6003-083:

Accordingly, the invention relates to an antibody, or an antigen-binding fragment thereof, comprising or consisting of:

a. a heavy chain variable domain CDR1 comprising SEQ ID NO:37;
b. a heavy chain variable domain CDR 2 comprising SEQ ID NO:38;
c. a heavy chain variable domain CDR 3 comprising SEQ ID NO:39;
d. a light chain variable domain CDR 1 comprising SEQ ID NO:40;
e. a light chain variable domain CDR 2 comprising SEQ ID NO:41; and
f. a light chain variable domain CDR 3 comprising SEQ ID NO:42.

Preferably, the monoclonal antibody may comprise or consist of the heavy chain variable domain of SEQ ID NO:121 and the light chain variable domain of SEQ ID NO:122.

Antibody 6003-799:

Accordingly, the invention relates to an antibody, or an antigen-binding fragment thereof, comprising or consisting of:

a. a heavy chain variable domain CDR1 comprising SEQ ID NO:43;
b. a heavy chain variable domain CDR 2 comprising SEQ ID NO:44;
c. a heavy chain variable domain CDR 3 comprising SEQ ID NO:45;
d. a light chain variable domain CDR 1 comprising SEQ ID NO:46;
e. a light chain variable domain CDR 2 comprising SEQ ID NO:47 and
f. a light chain variable domain CDR 3 comprising SEQ ID NO:48.

Preferably, the monoclonal antibody may comprise or consist of the heavy chain variable domain of SEQ ID NO:123 and the light chain variable domain of SEQ ID NO: 124.

Antibody 6003-910:

Accordingly, the invention relates to an antibody, or an antigen-binding fragment thereof, comprising or consisting of:

a. a heavy chain variable domain CDR1 comprising SEQ ID NO:49;
b. a heavy chain variable domain CDR 2 comprising SEQ ID NO:50;
c. a heavy chain variable domain CDR 3 comprising SEQ ID NO:51;
d. a light chain variable domain CDR 1 comprising SEQ ID NO:52;
e. a light chain variable domain CDR 2 comprising SEQ ID NO:53; and
f. a light chain variable domain CDR 3 comprising SEQ ID NO:54.

Preferably, the monoclonal antibody may comprise or consist of the heavy chain variable domain of SEQ ID NO: 125 and the light chain variable domain of SEQ ID NO: 126.

Antibody 6003-423:

Accordingly, the invention relates to an antibody, or an antigen-binding fragment thereof, comprising or consisting of:

a. a heavy chain variable domain CDR1 comprising SEQ ID NO:55;
b. a heavy chain variable domain CDR 2 comprising SEQ ID NO:56;
c. a heavy chain variable domain CDR 3 comprising SEQ ID NO:57;
d. a light chain variable domain CDR 1 comprising SEQ ID NO:58;
e. a light chain variable domain CDR 2 comprising SEQ ID NO:59; and
f. a light chain variable domain CDR 3 comprising SEQ ID NO:60.

Preferably, the monoclonal antibody may comprise or consist of the heavy chain variable domain of SEQ ID NO:127 and the light chain variable domain of SEQ ID NO:128.

Antibody 6003-822:

Accordingly, the invention relates to an antibody, or an antigen-binding fragment thereof, comprising or consisting of:

a. a heavy chain variable domain CDR1 comprising SEQ ID NO:61;
b. a heavy chain variable domain CDR 2 comprising SEQ ID NO:62;
c. a heavy chain variable domain CDR 3 comprising SEQ ID NO:63;
d. a light chain variable domain CDR 1 comprising SEQ ID NO:64;
e. a light chain variable domain CDR 2 comprising SEQ ID NO:65; and
f. a light chain variable domain CDR 3 comprising SEQ ID NO:66.

Preferably, the monoclonal antibody may comprise or consist of the heavy chain variable domain of SEQ ID NO:129 and the light chain variable domain of SEQ ID NO:130.

Antibody 6003-886:

Accordingly, the invention relates to an antibody, or an antigen-binding fragment thereof, comprising or consisting of:

a. a heavy chain variable domain CDR1 comprising SEQ ID NO:67;
b. a heavy chain variable domain CDR 2 comprising SEQ ID NO:68;
c. a heavy chain variable domain CDR 3 comprising SEQ ID NO:69;
d. a light chain variable domain CDR 1 comprising SEQ ID NO:70;
e. a light chain variable domain CDR 2 comprising SEQ ID NO:71; and
f. a light chain variable domain CDR 3 comprising SEQ ID NO:72.

Preferably, the monoclonal antibody may comprise or consist of the heavy chain variable domain of SEQ ID NO: 131 and the light chain variable domain of SEQ ID NO:132.

Antibody 6003-072:

Accordingly, the invention relates to an antibody, or an antigen-binding fragment thereof, comprising or consisting of:

a. a heavy chain variable domain CDR1 comprising SEQ ID NO:73;
b. a heavy chain variable domain CDR 2 comprising SEQ ID NO:74;
c. a heavy chain variable domain CDR 3 comprising SEQ ID NO:75;
d. a light chain variable domain CDR 1 comprising SEQ ID NO:76;
e. a light chain variable domain CDR 2 comprising SEQ ID NO:77; and
f. a light chain variable domain CDR 3 comprising SEQ ID NO:78.

Preferably, the monoclonal antibody may comprise or consist of the heavy chain variable domain of SEQ ID NO: 133 and the light chain variable domain of SEQ ID NO:134.

Antibody 6003-900:

Accordingly, the invention relates to an antibody, or an antigen-binding fragment thereof, comprising or consisting of:

a. a heavy chain variable domain CDR1 comprising SEQ ID NO:79;
b. a heavy chain variable domain CDR 2 comprising SEQ ID NO:80;
c. a heavy chain variable domain CDR 3 comprising SEQ ID NO:81;
d. a light chain variable domain CDR 1 comprising SEQ ID NO:82;
e. a light chain variable domain CDR 2 comprising SEQ ID NO:83; and
f. a light chain variable domain CDR 3 comprising SEQ ID NO:84.

Preferably, the monoclonal antibody may comprise or consist of the heavy chain variable domain of SEQ ID NO:135 and the light chain variable domain of SEQ ID NO: 136.

Antibody 6003-936:

Accordingly, the invention relates to an antibody, or an antigen-binding fragment thereof, comprising or consisting of:

a. a heavy chain variable domain CDR1 comprising SEQ ID NO:85;
b. a heavy chain variable domain CDR 2 comprising SEQ ID NO:86;
c. a heavy chain variable domain CDR 3 comprising SEQ ID NO:87;
d. a light chain variable domain CDR 1 comprising SEQ ID NO:88;
e. a light chain variable domain CDR 2 comprising SEQ ID NO:89; and
f. a light chain variable domain CDR 3 comprising SEQ ID NO:90.

Preferably, the monoclonal antibody may comprise or consist of the heavy chain variable domain of SEQ ID NO:137 and the light chain variable domain of SEQ ID NO:138.

Antibody 6003-408:

Accordingly, the invention relates to an antibody, or an antigen-binding fragment thereof, comprising or consisting of:

a. a heavy chain variable domain CDR1 comprising SEQ ID NO:91;
b. a heavy chain variable domain CDR 2 comprising SEQ ID NO:92;
c. a heavy chain variable domain CDR 3 comprising SEQ ID NO:93;
d. a light chain variable domain CDR 1 comprising SEQ ID NO:94;
e. a light chain variable domain CDR 2 comprising SEQ ID NO:95; and
f. a light chain variable domain CDR 3 comprising SEQ ID NO:96.

Preferably, the monoclonal antibody may comprise or consist of the heavy chain variable domain of SEQ ID NO: 139 and the light chain variable domain of SEQ ID NO:140.

Antibody 6003-471:

Accordingly, the invention relates to an antibody, or an antigen-binding fragment thereof, comprising or consisting of:

a. a heavy chain variable domain CDR1 comprising SEQ ID NO:97;
b. a heavy chain variable domain CDR 2 comprising SEQ ID NO:98;
c. a heavy chain variable domain CDR 3 comprising SEQ ID NO:99;
d. a light chain variable domain CDR 1 comprising SEQ ID NO:100;
e. a light chain variable domain CDR 2 comprising SEQ ID NO:101; and
f. a light chain variable domain CDR 3 comprising SEQ ID NO:102.

Preferably, the monoclonal antibody may comprise or consist of the heavy chain variable domain of SEQ ID NO:141 and the light chain variable domain of SEQ ID NO:142.

Antibody 6003-972:

Accordingly, the invention relates to an antibody, or an antigen-binding fragment thereof, comprising or consisting of:

a. a heavy chain variable domain CDR1 comprising SEQ ID NO:103;
b. a heavy chain variable domain CDR 2 comprising SEQ ID NO:104;
c. a heavy chain variable domain CDR 3 comprising SEQ ID NO:105;
d. a light chain variable domain CDR 1 comprising SEQ ID NO:106;
e. a light chain variable domain CDR 2 comprising SEQ ID NO:107; and
f. a light chain variable domain CDR 3 comprising SEQ ID NO:108.

Preferably, the monoclonal antibody may comprise or consist of the heavy chain variable domain of SEQ ID NO:143 and the light chain variable domain of SEQ ID NO: 144.

The antibodies mentioned above may, according to one embodiment, further comprise a variant with no more than 4 amino acid differences, or no more than 3 amino acid differences, or no more than 2 amino acid differences, or no more than 1 amino acid difference from said CDR1, CDR2, and/or CDR3 (HC and/or VC) sequences.

Further, the antibodies may be in a composition together with a pharmaceutically acceptable carrier. The antibodies of the invention may be used in therapy. In particular, the antibodies of the invention may be used in treating FTD or ALS or proteinopathies such as Alzheimer's Disease (AD).

The treatment envisioned by the present invention may be chronic and the patient may be treated at least 2 weeks, such as at least for 1 month, 6, months, 1 year or more.

The antibodies of the present invention may, for example, be monoclonal antibodies produced by the hybridoma method first described by Kohler et al., Nature 256, 495 (1975), or may be monoclonal antibodies produced by recombinant DNA or other methods. Monoclonal antibodies may also be isolated from phage antibody libraries using the techniques described in, for example, Clackson et al., Nature 352, 624-628 (1991) and Marks et al., J. Mol. Biol. 222, 581-597 (1991). Monoclonal antibodies may be obtained from any suitable source. Thus, for example, monoclonal antibodies may be obtained from hybridomas prepared from murine splenic B lymphocyte cells obtained from mice immunized with an antigen of interest, for instance, in the form of cells expressing the antigen on the surface, or a nucleic acid encoding an antigen of interest. Monoclonal antibodies may also be obtained from hybridomas derived from antibody-expressing cells of immunized humans or from non-human mammals such as rats, rabbits, dogs, sheep, goats, primates, etc.

In one embodiment, the antibody of the invention is a human antibody. Human monoclonal antibodies directed against Sortilin may be generated using transgenic or transchromosomal mice carrying parts of the human immune system rather than the mouse system. Such transgenic and trans-chromosomic mice include mice referred to herein as HuMAb mice and KM mice, respectively.

The HuMAb mouse contains a human immunoglobulin gene minilocus that encodes unrearranged human heavy variable and constant (μ and Y) and light variable and constant (κ) chain immunoglobulin sequences, together with targeted mutations that inactivate the endogenous μ and K chain loci (Lonberg, N. et al., Nature 368, 856-859 (1994)). Accordingly, the mice exhibit reduced expression of mouse IgM or K and in response to immunization, the introduced human heavy and light chain transgenes, undergo class switching and somatic mutation to generate high affinity human IgG, κ monoclonal antibodies (Lonberg, N. et al. (1994), supra; reviewed in Lonberg, N., Handbook of Experimental Pharmacology 113, 49-101 (1994), Lonberg, N. and Huszar, D., Intern. Rev. Immunol. Vol. 13 65-93 (1995) and Harding, F. and Lonberg, N., Ann. N. Y. Acad. Sci 764 536-546 (1995)). The preparation of HuMAb mice is described in detail in Taylor, L. et al., Nucleic Acids Research 20, 6287-6295 (1992), Chen, J. et al., International Immunology 5, 647-656 (1993), Tuaillon et al., J. Immunol. 152, 2912-2920 (1994), Taylor, L. et al., International Immunology 6, 579-591 (1994), Fishwild, D. et al., Nature Biotechnology 14, 845-851 (1996). See also U.S. Pat. Nos. 5,545,806, 5,569,825, 5,625,126, 5,633,425, 5,789,650, 5,877,397, 5,661,016, 5,814,318, 5,874,299, 5,770,429, 5,545,807, WO 98/24884, WO 94/25585, WO 93/1227, WO 92/22645, WO 92/03918 and WO 01/09187.

The HCo7, HCo12, HCo17 and HCo20 mice have a JKD disruption in their endogenous light chain (kappa) genes (as described in Chen et al., EMBO J. 12, 811-820 (1993)), a CMD disruption in their endogenous heavy chain genes (as described in Example 1 of WO 01/14424), and a KCo5 human kappa light chain transgene (as described in Fishwild et al., Nature Biotechnology 14, 845-851 (1996)). Additionally, the HCo7 mice have a HCo7 human heavy chain transgene (as described in U.S. Pat. No. 5,770,429), the HCo12 mice have a HCo12 human heavy chain transgene (as described in Example 2 of WO 01/14424), the HCo17 mice have a HCo17 human heavy chain transgene (as described in Example 2 of WO 01/09187) and the HCo20 mice have a HCo20 human heavy chain transgene. The resulting mice express human immunoglobulin heavy and kappa light chain transgenes in a background homozygous for disruption of the endogenous mouse heavy and kappa light chain loci.

In the KM mouse strain, the endogenous mouse kappa light chain gene has been homozygously disrupted as described in Chen et al., EMBO J. 12, 811-820 (1993) and the endogenous mouse heavy chain gene has been homozygously disrupted as described in Example 1 of WO 01/09187. This mouse strain carries a human kappa light chain transgene, KCo5, as described in Fishwild et al., Nature Biotechnology 14, 845-851 (1996). This mouse strain also carries a human heavy chain transchromosome composed of chromosome 14 fragment hCF (SC20) as described in WO 02/43478. HCo12-Balb/c, HCo17-Balb/c and HCo20-Balb/c mice can be generated by crossing HCo12, HCo17 and HCo20 to KCo5 [J/K] (Balb) as described in WO 09/097006.

In the KM mouse strain, the endogenous mouse kappa light chain gene has been homozygously disrupted as described in Chen et al., EMBO J. 12, 811-820 (1993) and the endogenous mouse heavy chain gene has been homozygously disrupted as described in Example 1 of WO 01/09187. This mouse strain carries a human kappa light chain transgene, KCo5, as described in Fishwild et al., Nature Biotechnology 14, 845-851 (1996). This mouse strain also carries a human heavy chain trans-chromosome composed of chromosome 14 antigen-binding fragment hCF (SC20) as described in WO 02/43478.

Splenocytes from these transgenic mice may be used to generate hybridomas that secrete human monoclonal antibodies according to well-known techniques. Human monoclonal or polyclonal antibodies of the present invention, or antibodies of the present invention originating from other species may also be generated transgenically through the generation of another non-human mammal or plant that is transgenic for the immunoglobulin heavy and light chain sequences of interest and production of the antibody in a recoverable form therefrom. In connection with the transgenic production in mammals, antibodies may be produced in, and recovered from, the milk of goats, cows, or other mammals. See for instance U.S. Pat. Nos. 5,827,690, 5,756,687, 5,750,172 and 5,741,957.

The antibody of the invention may be of any isotype. The choice of isotype typically will be guided by the desired effector functions, such as ADCC induction. Exemplary isotypes are IgG1, IgG2, IgG3, and IgG4. Either of the human light chain constant domains, kappa or lambda, may be used. If desired, the class of an anti-Sortilin antibody of the present invention may be switched by known methods.

For example, an antibody of the present invention that was originally IgM may be class switched to an IgG antibody of the present invention. Further, class switching techniques may be used to convert one IgG subclass to another, for instance from IgGI to IgG2. Thus, the effector function of the antibodies of the present invention may be changed by isotype switching to, e.g., an IgG1, IgG2, IgG3, IgG4 antibody for various therapeutic uses. In one embodiment an antibody of the present invention is an IgG1 antibody, for instance an IgG1, K. An antibody is said to be of a particular isotype if its amino acid sequence is most homologous to that isotype, relative to other isotypes.

In one embodiment, the antibody of the invention is a full-length antibody, preferably an IgG antibody, in particular an IgG1, K antibody. In another embodiment, the antibody of the invention is an antibody antigen-binding fragment or a single-chain antibody.

Antibodies and antigen-binding fragments thereof may e.g. be obtained by antigen-binding fragmentation using conventional techniques, and antigen-binding fragments screened for utility in the same manner as described herein for whole antibodies. For example, F(ab')2 antigen-binding fragments may be generated by treating antibody with pepsin. The resulting F(ab')2 antigen-binding fragment may be treated to reduce disulfide bridges to produce Fab' antigen-binding fragments. Fab antigen-binding fragments may be obtained by treating an IgG antibody with papain; Fab' antigen-binding fragments may be obtained with pepsin digestion of IgG antibody. An F(ab') antigen-binding fragment may also be produced by binding Fab'-described below via a thioether bond or a disulfide bond. A Fab' antigen-binding fragment is an antibody antigen-binding fragment obtained by cutting a disulfide bond of the hinge domain of the F(ab')2. A Fab'-antigen-binding fragment may be obtained by treating an F(ab')2 antigen-binding fragment with a reducing agent, such as dithiothreitol. Antibody antigen-binding fragment may also be generated by expression of nucleic acids encoding such antigen-binding fragments in recombinant cells (see for instance Evans et al., J. Immunol. Meth. 184, 123-38 (1995)). For example, a chimeric gene encoding a portion of an F(ab')2 antigen-binding fragment could include DNA sequences encoding the CH1 domain and hinge domain of the H chain, followed by a translational stop codon to yield such a truncated antibody antigen-binding fragment molecule.

In one embodiment, the anti-Sortilin antibody is a monovalent antibody, preferably a monovalent antibody as described in WO2007059782 (which is incorporated herein by reference in its entirety) having a deletion of the hinge region. Accordingly, in one embodiment, the antibody is a monovalent antibody, wherein said anti-Sortilin antibody is constructed by a method comprising: i) providing a nucleic acid construct encoding the light chain of said monovalent antibody, said construct comprising a nucleotide sequence encoding the VL region of a selected antigen specific anti-Sortilin antibody and a nucleotide sequence encoding the constant CL region of an Ig, wherein said nucleotide sequence encoding the VL region of a selected antigen specific antibody and said nucleotide sequence encoding the CL region of an Ig are operably linked together, and wherein, in case of an IgG1 subtype, the nucleotide sequence encoding the CL region has been modified such that the CL region does not contain any amino acids capable of forming disulfide bonds or covalent bonds with other peptides comprising an identical amino acid sequence of the CL region in the presence of polyclonal human IgG or when administered to an animal or human being; ii) providing a nucleic acid construct encoding the heavy chain of said monovalent antibody, said construct comprising a nucleotide sequence encoding the VH region of a selected antigen specific antibody and a nucleotide sequence encoding a constant CH region of a human Ig, wherein the nucleotide sequence encoding the CH region has been modified such that the region corresponding to the hinge region and, as required by the Ig subtype, other regions of the CH region, such as the CH3 region, does not comprise any amino acid residues which participate in the formation of disulphide bonds or covalent or stable non-covalent inter-heavy chain bonds with other peptides comprising an identical amino acid sequence of the CH region of the human Ig in the presence of polyclonal human IgG or when administered to an animal human being, wherein said nucleotide sequence encoding the VH region of a selected antigen specific antibody and said nucleotide sequence encoding the CH region of said Ig are operably linked together; iii) providing a cell expression system for producing said monovalent antibody; iv) producing said monovalent antibody by co-expressing the nucleic acid constructs of (i) and (ii) in cells of the cell expression system of (iii).

Similarly, in one embodiment, the anti-Sortilin antibody is a monovalent antibody, which comprises:

(i) a variable domain of an antibody of the invention as described herein or an antigen-binding part of the said domain, and (ii) a CH domain of an immunoglobulin or a domain thereof comprising the CH2 and CH3 domains, wherein the CH domain or domain thereof has been modified such that the domain corresponding to the hinge domain and, if the immunoglobulin is not an IgG4 subtype, other domains of the CH domain, such as the CH3 domain, do not comprise any amino acid residues, which are capable of forming disulfide bonds with an identical CH domain or other covalent or stable non-covalent inter-heavy chain bonds with an identical CH domain in the presence of polyclonal human IgG.

In a further embodiment, the heavy chain of the monovalent antibody has been modified such that the entire hinge region has been deleted.

In another further embodiment, the sequence of the monovalent antibody has been modified so that it does not comprise any acceptor sites for N-linked glycosylation.

The invention also includes "Bispecific Antibodies," wherein an anti-Sortilin binding region (e.g., a Sortilin-binding region of an anti-Sortilin monoclonal antibody) is part of a bivalent or polyvalent bispecific scaffold that targets more than one epitope, (for example a second epitope could comprise an epitope of an active transport receptor, such that the Bispecific Antibody would exhibit improved transcytosis across a biological barrier, such as the Blood Brain Barrier). Thus, in another further embodiment, the monovalent Fab of an anti-Sortilin antibody may be joined to an additional Fab or scfv that targets a different protein to generate a bispecific antibody. A bispecific antibody can have a dual function, for example a therapeutic function imparted by an anti-sortilin binding domain and a transport function that can bind to a receptor molecule to enhance transfer cross a biological barrier, such as the blood brain barrier.

Antibodies and antigen-binding fragments thereof of the invention also include single chain antibodies. Single chain antibodies are peptides in which the heavy and light chain Fv domains are connected. In one embodiment, the present invention provides a single-chain Fv (scFv) wherein the heavy and light chains in the Fv of an anti-Sortilin antibody of the present invention are joined with a flexible peptide linker (typically of about 10, 12, 15 or more amino acid residues) in a single peptide chain. Methods of producing such antibodies are described in for instance U.S. Pat. No. 4,946,778, Pluckthun in The Pharmacology of Monoclonal Antibodies, vol. 113, Rosenburg and Moore eds. Springer-Verlag, New York, pp. 269-315 (1994), Bird et al., Science 242, 423-426 (1988), Huston et al., PNAS USA 85, 5879-5883 (1988) and McCafferty et al., Nature 348, 552-554 (1990). The single chain antibody may be monovalent, if only a single VH and VL are used, bivalent, if two VH and VL are used, or polyvalent, if more than two VH and VL are used.

The antibodies and antigen-binding fragments thereof described herein may be modified by inclusion of any suitable number of modified amino acids and/or associations with such conjugated substituents. Suitability in this context is generally determined by the ability to at least substantially retain the Sortilin selectivity and/or Sortilin specificity associated with the non-derivatized parent anti-Sortilin antibody. The inclusion of one or more modified amino acids may be advantageous in, for example, increasing polypeptide serum half-life, reducing polypeptide antigenicity, or increasing polypeptide storage stability. Amino acid(s) are modified, for example, co-translationally or post-translationally during recombinant production (e.g., N-linked glycosylation at N—X—S/T motifs during expression in mammalian cells) or modified by synthetic means. Non-limiting examples of a modified amino acid include a glycosylated amino acid, a sulfated amino acid, a prenylated (e.g., farnesylated, geranyl-geranylated) amino acid, an acetylated amino acid, an acylated amino acid, a PEGylated amino acid, a biotinylated amino acid, a carboxylated amino acid, a phosphorylated amino acid, and the like. References adequate to guide one of skill in the modification of amino acids are replete throughout the literature. Example protocols are found in Walker (1998) Protein Protocols On CD-Rom, Humana Press, Totowa, NJ. The modified amino acid may, for instance, be selected from a glycosylated amino acid, a PEGylated amino acid, a farnesylated amino acid, an acetylated amino acid, a biotinylated amino acid, an amino acid conjugated to a lipid moiety, or an amino acid conjugated to an organic derivatizing agent.

The antibodies and antigen-binding fragments thereof of the invention, may also be chemically modified by covalent conjugation to a polymer to for instance increase their circulating half-life. Exemplary polymers, and methods to attach them to peptides, are illustrated in for instance U.S. Pat. Nos. 4,766,106; 4,179,337; 4,495,285 and 4,609,546. Additional illustrative polymers include polyoxyethylated polyols and polyethylene glycol (PEG) (e.g., a PEG with a molecular weight of between about 1,000 and about 40,000, such as between about 2,000 and about 20,000, e.g., about 3,000-12,000 g/mol).

The antibodies and antigen-binding fragments thereof of the present invention may further be used in a diagnostic method or as a diagnostic imaging ligand.

In one embodiment, antibodies and antigen-binding fragments thereof of the invention comprising one or more radiolabeled amino acids are provided. A radiolabeled anti-Sortilin antibody may be used for both diagnostic and therapeutic purposes (conjugation to radiolabeled molecules is another possible feature). Nonlimiting examples of such labels include, but are not limited to bismuth ($^{213}$Bi), carbon ($^{11}$C, $^{13}$C, $^{14}$C), chromium ($^{51}$Cr), cobalt ($^{57}$Co, $^{60}$Co), copper ($^{64}$Cu), dysprosium ($^{165}$Dy), erbium ($^{169}$Er), fluorine ($^{18}$F), gadolinium ($^{153}$Gd, $^{159}$Gd), gallium ($^{68}$Ga, $^{67}$Ga), germanium ($^{68}$Ge), gold ($^{198}$Au), holmium ($^{166}$Ho), hydrogen ($^{3}$H), indium ($^{111}$In, $^{112}$In, $^{113}$In, $^{115}$In), iodine ($^{121}$I, $^{123}$I, $^{125}$I, $^{131}$I), iridium (192Ir), iron ($^{59}$Fe), krypton ($^{81m}$Kr), lanthanum ($^{140}$La), lutetium ($^{17}$Lu), manganese ($^{54}$Mn), molybdenum ($^{99}$Mo), nitrogen ($^{13}$N, $^{15}$N), oxygen ($^{15}$O), palladium ($^{103}$Pd), phosphorus ($^{32}$P), potassium ($^{42}$K), praseodymium ($^{142}$Pr), promethium ($^{149}$Pm), rhenium ($^{186}$Re, $^{188}$Re), rhodium ($^{105}$Rh), rubidium ($^{81}$Rb, $^{82}$Rb), ruthenium ($^{82}$Ru, $^{97}$Ru), samarium ($^{153}$Sm), scandium ($^{47}$Sc), selenium ($^{75}$Se), sodium ($^{24}$Na), strontium ($^{85}$Sr, $^{89}$Sr, $^{92}$Sr), sulfur ($^{35}$S), technetium ($^{99}$Tc), thallium ($^{201}$Tl), tin ($^{113}$Sn, $^{117}$Sn), xenon ($^{133}$Xe), ytterbium ($^{169}$Yb, $^{175}$Yb, $^{177}$Yb), yttrium ($^{90}$Y) and zinc ($^{65}$Zn). Methods for preparing radiolabeled amino acids and related peptide derivatives are known in the art (see for instance Junghans et al., in Cancer Chemotherapy and Biotherapy 655-686 (2nd edition, Chafner and Longo, eds., Lippincott Raven (1996)) and U.S. Pat. Nos. 4,681,581, 4,735,210, 5,101,827, 5,102,990 (U.S. RE35, 500), U.S. Pat. Nos. 5,648,471 and 5,697,902. For example, a radioisotope may be conjugated by a chloramine T method (Lindegren, S. et al. (1998) "*Chloramine-T In High-Specific-Activity Radioiodination Of Antibodies Using N-Succinimidyl*-3-(*Trimethylstannyl*)*Benzoate As An Intermediate*," Nucl. Med. Biol. 25 (7): 659-665; Kurth, M. et al. (1993) "*Site-Specific Conjugation Of A Radio iodinated Phenethylamine Derivative To A Monoclonal Antibody Results In Increased Radioactivity Localization In Tumor*," J. Med. Chem. 36(9):1255-1261; Rea, D. W. et al. (1990) "Site-specifically radio-iodinated antibody for targeting tumors," Cancer Res. 50(3 Suppl):857s-861s).

The invention also provides anti-Sortilin antibodies and antigen-binding fragments thereof that are detectably labeled using a fluorescent label (such as a rare earth chelate (e.g., a europium chelate)), a fluorescein-type label (e.g., fluorescein, fluorescein isothiocyanate, 5-carboxyfluorescein, 6-carboxy fluorescein, dichlorotriazinylamine fluorescein), a rhodamine-type label (e.g., ALEXA FLUOR® 568 (Invitrogen), TAMRA® or dansyl chloride), VIVOTAG 680 XL FLUOROCHROME™ (Perkin Elmer), phycoerythrin; umbelliferone, Lissamine; a cyanine; a phycoerythrin, Texas Red, BODIPY FL-SE® (Invitrogen) or an analogue thereof, all of which are suitable for optical detection. Chemiluminescent labels may be employed (e.g., luminol, luciferase, luciferin, and aequorin). Such diagnosis and detection can also be accomplished by coupling the diagnostic molecule of the present invention to detectable substances including, but not limited to, various enzymes, enzymes including, but not limited to, horseradish peroxidase, alkaline phosphatase, beta-galactosidase, or acetylcholinesterase, or to prosthetic group complexes such as, but not limited to, streptavidin/biotin and avidin/biotin.

Chemiluminescent labels may be employed (e.g., luminol, luciferase, luciferin, and aequorin). Such diagnosis and detection can also be accomplished by coupling the diagnostic molecule of the present invention to detectable substances including, but not limited to, various enzymes, enzymes including, but not limited to, horseradish peroxidase, alkaline phosphatase, beta-galactosidase, or acetylcholinesterase, or to prosthetic group complexes such as, but not limited to, streptavidin/biotin and avidin/biotin. Paramagnetic labels can also be employed, and are preferably detected using Positron Emission Tomography (PET) or Single-Photon Emission Computed Tomography (SPECT). Such paramagnetic labels include, but are not limited to compounds containing paramagnetic ions of Aluminum (Al), Barium (Ba), Calcium (Ca), Cerium (Ce), Dysprosium (Dy), Erbium (Er), Europium (Eu), Gadolinium (Gd), Holmium (Ho), Iridium (Ir), Lithium (Li), Magnesium (Mg), Manganese (Mn), Molybdenum (M), Neodymium (Nd), Osmium (Os), Oxygen (O), Palladium (Pd), Platinum (Pt), Rhodium (Rh), Ruthenium (Ru), Samarium (Sm), Sodium (Na), Strontium (Sr), Terbium (Tb), Thulium (Tm), Tin (Sn), Titanium (Ti), Tungsten (W), and Zirconium (Zi), and particularly, $Co^{+2}$, $CR^{+2}$, $Cr^{+3}$, $Cu^{+2}$, $Fe^{+2}$, $Fe^{+3}$, $Ga^{+3}$, $Mn^{+3}$, $Ni^{+2}$, $Ti^{+3}$, $V^{+3}$, and $V^{+4}$, positron emitting metals using various positron emission tomographies, and non-radioactive paramagnetic metal ions.

Thus in one embodiment the anti-Sortilin antibody or Sortilin-binding fragment thereof of the invention may be labelled with a fluorescent label, a chemiluminescent label, a paramagnetic label, a radioisotopic label or an enzyme label. The labelled antibody of fragment may be used in detecting or measuring the presence or amount of said Sortilin in the brain of a subject. This method may comprise the detection or measurement of in vivo imaging of anti-Sortilin antibody or Sortilin-binding fragment bound to said Sortilin and may comprises ex vivo imaging of said anti-Sortilin antibody or Sortilin-binding fragment bound to such Sortilin.

In a further aspect, the invention relates to an expression vector encoding one or more polypeptide chains of an antibody of the invention or an antigen-binding-domain thereof. Such expression vectors may be used for recombinant production of the antibodies and antigen-binding fragments of the invention.

An expression vector in the context of the present invention may be any suitable DNA or RNA vector, including chromosomal, non-chromosomal, and synthetic nucleic acid vectors (a nucleic acid sequence comprising a suitable set of expression control elements). Examples of such vectors include derivatives of SV40, bacterial plasmids, phage DNA, baculovirus, yeast plasmids, vectors derived from combinations of plasmids and phage DNA, and viral nucleic acid (RNA or DNA) vectors. In one embodiment, an anti-Sortilin antibody-encoding nucleic acid is comprised in a naked DNA or RNA vector, including, for example, a linear expression element (as described in, for instance, Sykes and Johnston, Nat Biotech 12, 355-59 (1997)), a compacted nucleic acid vector (as described in for instance U.S. Pat. No. 6,077,835 and/or WO 00/70087), a plasmid vector such as pBR322, pUC 19/18, or pUC 118/119, a "midge" minimally-sized nucleic acid vector (as described in, for instance, Schakowski et al., Mol Ther 3, 793-800 (2001)), or as a precipitated nucleic acid vector construct, such as a $CaPO_4$-precipitated construct (as described in, for instance, WO 00/46147, Benevity and Reshef, PNAS USA 83, 9551-55 (1986), Wigler et al., Cell 14, 725 (1978), and Coraro and Pearson, Somatic Cell Genetics 2, 603 (1981)). Such nucleic acid vectors and the usage thereof are well known in the art (see for instance U.S. Pat. Nos. 5,589,466 and 5,973,972).

In one embodiment, the vector is suitable for expression of anti-Sortilin antibodies or antigen-binding fragments thereof in a bacterial cell. Examples of such vectors include expression vectors such as BlueScript (Stratagene), pIN vectors (Van Heeke & Schuster, J Biol Chem 264, 5503-5509 (1989), pET vectors (Novagen, Madison, WI) and the like).

An expression vector may also or alternatively be a vector suitable for expression in a yeast system. Any vector suitable for expression in a yeast system may be employed. Suitable vectors include, for example, vectors comprising constitutive or inducible promoters such as alpha factor, alcohol oxidase and PGH (reviewed in: F. Ausubel et al., ed. Current Protocols in Molecular Biology, Greene Publishing and Wiley InterScience New York (1987), Grant et al., Methods in Enzymol 153, 516-544 (1987), Mattanovich, D. et al. Methods Mol. Biol. 824, 329-358 (2012), Celik, E. et al. Biotechnol. Adv. 30(5), 1108-1118 (2012), Li, P. et al. Appl. Biochem. Biotechnol. 142(2), 105-124 (2007), Böer, E. et al. Appl. Microbiol. Biotechnol. 77(3), 513-523 (2007), van der Vaart, J. M. Methods Mol. Biol. 178, 359-366 (2002), and Holliger, P. Methods Mol. Biol. 178, 349-357 (2002)).

In an expression vector of the invention, anti-Sortilin antibody-encoding nucleic acids may comprise or be associated with any suitable promoter, enhancer, and other expression-facilitating elements. Examples of such elements include strong expression promoters (e.g., human CMV IE promoter/enhancer as well as RSV, SV40, SL3-3, MMTV, and HIV LTR promoters), effective poly (A) termination sequences, an origin of replication for plasmid product in *E. coli*, an antibiotic resistance gene as selectable marker, and/or a convenient cloning site (e.g., a polylinker). Nucleic acids may also comprise an inducible promoter as opposed to a constitutive promoter such as CMV IE (the skilled artisan will recognize that such terms are actually descriptors of a degree of gene expression under certain conditions).

In an even further aspect, the invention relates to a recombinant eukaryotic or prokaryotic host cell, such as a transfectoma, which produces an antibody or antigen-binding fragment thereof of the invention as defined herein or a bispecific molecule of the invention as defined herein. Examples of host cells include yeast, bacteria, and mammalian cells, such as CHO or HEK cells. For example, in one embodiment, the present invention provides a cell comprising a nucleic acid stably integrated into the cellular genome that comprises a sequence coding for expression of an anti-Sortilin antibody of the present invention or an antigen-binding fragment thereof. In another embodiment, the present invention provides a cell comprising a non-integrated nucleic acid, such as a plasmid, cosmid, phagemid, or linear expression element, which comprises a sequence coding for expression of an anti-Sortilin antibody or antigen-binding fragment thereof of the invention.

In a further aspect, the invention relates to a method for producing an anti-Sortilin antibody of the invention, said method comprising the steps of a) culturing a hybridoma or a host cell of the invention as described herein above, and b) purifying the antibody of the invention from the culture media.

In one embodiment, the invention relates to a preparation that, as such term is used herein, comprises an anti-Sortilin antibody as defined herein, and that is substantially free of naturally-arising antibodies that are either not capable of binding to sortilin or that do not materially alter the anti-Sortilin functionality of the preparation. Thus, such a preparation does not encompass naturally-arising serum, or a purified derivative of such serum, that comprises a mixture of an anti-Sortilin antibody and another antibody that does not alter the functionality of the anti-Sortilin antibody of the preparation, wherein such functionality is:

(i) a binding affinity ($K_D$) for Sortilin;
(ii) a;
(iii) a capability to reduce and/or inhibit clearance of PGRN by Sortilin-expressing cells;
(iv) a capability to reduce and/or inhibit the endocytosis of PGRN by Sortilin-expressing cells;
(v) a capability to increase the amount and/or concentration of PGRN in the plasma in human-Sortilin-expressing knock-in mice; a capability to increase the amount and/or concentration of PGRN in the brain and/or (vi) a capability, when administered chronically, to provide treatment of frontotemporal dementia (FTD) and/or amyotrophic lateral sclerosis (ALS).

The invention particularly relates to preparations of such an anti-Sortilin antibody having a structural change in its amino acid sequence (in any of its CDRs, variable domains, framework residues and/or constant domains) relative to the structure of a naturally-occurring anti-Sortilin antibody, wherein said structural change causes the anti-Sortilin antibody monoclonal antibody to exhibit a markedly altered functionality (i.e., more than a 20% difference, more than a 40% difference, more than a 60% difference, more than an 80% difference, more than a 100% difference, more than a 150% difference, more than a 2-fold difference, more than a 4-fold difference, more than a 5-fold difference, or more than a 10-fold difference in functionality) relative to the functionality exhibited by said naturally-occurring anti-Sortilin antibody; wherein such functionality is:

(i) a binding affinity ($K_D$) for Sortilin;

(ii) a capability to reduce and/or inhibit clearance of PGRN by Sortilin-expressing cells;

(iii) a capability to reduce and/or inhibit the endocytosis of PGRN by Sortilin-expressing cells;

(iv) a capability to increase the amount and/or concentration of PGRN in the plasma in human-Sortilin-expressing knock-in mice;

(v) a capability to increase the amount and/or concentration of PGRN in the brain and/or (vi) a capability, when administered chronically, to provide treatment of frontotemporal dementia (FTD), amyotrophic lateral sclerosis (ALS) and/or Alzheimer's Disease (AD).

especially wherein such altered functionality is a result of the structural change and thus is inseparable from it.

The term "substantially free" of naturally-arising antibodies refers to the complete absence of such naturally-arising antibodies in such preparations, or of the inclusion of a concentration of such naturally-arising antibodies in such preparations that does not materially affect the Sortilin-binding properties of the preparations. An antibody is said to be "isolated" if it has no naturally-arising counterpart or has been separated or purified from components which naturally accompany it.

The term "naturally-arising antibodies," as it relates to such preparations, refers to antibodies (including naturally-arising autoantibodies) elicited within living humans or other animals, as a natural consequence to the functioning of their immune systems.

Thus, the preparations of the present invention do not exclude, and indeed explicitly encompass, such preparations that contain an anti-Sortilin antibody and a deliberately added additional antibody capable of binding to an epitope that is not possessed by Sortilin. Such preparations particularly include embodiments thereof wherein the preparation exhibits enhanced efficacy in treating frontotemporal dementia (FTD) and/or amyotrophic lateral sclerosis (ALS).

The antibodies of antigen-binding fragments thereof of the present invention may be produced in different cell lines, such as a human cell line, a mammal non-human cell line, and insect cell line, for example a CHO cell line, HEK cell line, BHK-21 cell line, murine cell line (such as a myeloma cell line), fibrosarcoma cell line, PER.C6 cell line, HKB-11 cell line, CAP cell line and HuH-7 human cell line (Dumont et al, 2015, Crit Rev Biotechnol. September 18:1-13, the contents which is included herein by reference).

In an even further aspect, the invention relates to a pharmaceutical composition comprising:

(i) an anti-Sortilin antibody or antigen-binding fragment thereof, both as defined herein, or a preparation, as such term is defined herein, that comprises such an anti-Sortilin antibody or antigen-binding fragment thereof; and (ii) a pharmaceutically-acceptable carrier.

The pharmaceutical compositions may be formulated with pharmaceutically acceptable carriers or diluents as well as any other known adjuvants and excipients in accordance with conventional techniques such as those disclosed in Remington: The Science and Practice of Pharmacy, 22nd Edition, Gennaro, Ed., Mack Publishing Co., Easton, PA, 2013.

The pharmaceutically acceptable carriers or diluents as well as any other known adjuvants and excipients should be suitable for the chosen compound of the present invention and the chosen mode of administration. Suitability for carriers and other components of pharmaceutical compositions is determined based on the lack of significant negative impact on the desired biological properties of the chosen compound or pharmaceutical composition of the present invention (e.g., less than a substantial impact (10% or less relative inhibition, 5% or less relative inhibition, etc.)) on epitope binding.

A pharmaceutical composition of the present invention may also include diluents, fillers, salts, buffers, detergents (e.g., a non-ionic detergent, such as Tween-20 or Tween-80), stabilizers (e.g., sugars or protein-free amino acids), preservatives, tissue fixatives, solubilizers, and/or other materials suitable for inclusion in a pharmaceutical composition. The diluent is selected to not to affect the biological activity of the combination. Examples of such diluents are distilled water, physiological phosphate-buffered saline, Ringer's solutions, dextrose solution, and Hank's solution. In addition, the pharmaceutical composition or formulation may also include other carriers, or non-toxic, nontherapeutic, non-immunogenic stabilizers and the like. The compositions may also include large, slowly metabolized macromolecules, such as proteins, polysaccharides like chitosan, polylactic acids, polyglycolic acids and copolymers (e.g., latex functionalized sepharose, agarose, cellulose, and the like), polymeric amino acids, amino acid copolymers, and lipid aggregates (e.g., oil droplets or liposomes).

The actual dosage levels of the active ingredients in the pharmaceutical compositions of the present invention may be varied so as to obtain an amount of the active ingredient which is effective to achieve the desired therapeutic response for a particular patient, composition, and mode of administration. The selected dosage level will depend upon a variety of pharmacokinetic factors including the activity of the particular compositions of the present invention employed, or the amide thereof, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts.

The pharmaceutical composition may be administered by any suitable route and mode, including: parenteral, topical, oral or intranasal means for prophylactic and/or therapeutic treatment. In one embodiment, a pharmaceutical composition of the present invention is administered parenterally. The phrases "parenteral administration" and "administered parenterally" as used herein means modes of administration other than enteral and topical administration, usually by injection, and include epidermal, intravenous, intramuscular, intraarterial, intrathecal, intracapsular, intraorbital, intracardiac, intradermal, intraperitoneal, intratendinous, transtracheal, subcutaneous, subcuticular, intraarticular, subcapsular, subarachnoid, intraspinal, intracranial, intrathoracic, epidural and intrasternal injection and infusion. Additional suitable routes of administering a compound of the present invention in vivo and in vitro are well known in the art and may be selected by those of ordinary skill in the art. In one embodiment that pharmaceutical composition is administered by intravenous or subcutaneous injection or infusion.

Pharmaceutically acceptable carriers include any and all suitable solvents, dispersion media, coatings, antibacterial and antifungal agents, isotonicity agents, antioxidants and absorption delaying agents, and the like that are physiologically compatible with a compound of the present invention.

Examples of suitable aqueous and non-aqueous carriers which may be employed in the pharmaceutical compositions of the present invention include water, saline, phosphate buffered saline, ethanol, dextrose, polyols (such as glycerol, propylene glycol, polyethylene glycol, and the like), and suitable mixtures thereof, vegetable oils, such as olive oil, corn oil, peanut oil, cottonseed oil, and sesame oil, carboxymethyl cellulose colloidal solutions, tragacanth gum and injectable organic esters, such as ethyl oleate, and/or various buffers. Other carriers are well known in the pharmaceutical arts.

Pharmaceutically acceptable carriers include sterile aqueous solutions or dispersions and sterile powders for the extemporaneous preparation of sterile injectable solutions or dispersion. The use of such media and agents for pharmaceutically active substances is known in the art. Except insofar as any conventional media or agent is incompatible with the active compound, use thereof in the pharmaceutical compositions of the present invention is contemplated.

Proper fluidity may be maintained, for example, by the use of coating materials, such as lecithin, by the maintenance of the required particle size in the case of dispersions, and by the use of surfactants.

Pharmaceutical compositions of the present invention may also comprise pharmaceutically acceptable antioxidants for instance (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Pharmaceutical compositions of the present invention may also comprise isotonicity agents, such as sugars, polyalcohols, such as mannitol, sorbitol, glycerol or sodium chloride in the compositions.

The pharmaceutical compositions of the present invention may also contain one or more adjuvants appropriate for the chosen route of administration such as preservatives, wetting agents, emulsifying agents, dispersing agents, preservatives or buffers, which may enhance the shelf life or effectiveness of the pharmaceutical composition. The compounds of the present invention may be prepared with carriers that will protect the compound against rapid release, such as a controlled release formulation, including implants, transdermal patches, and microencapsulated delivery systems. Such carriers may include gelatin, glyceryl monostearate, glyceryl distearate, biodegradable, biocompatible polymers such as ethylene vinyl acetate, polyanhydrides, polyglycolic acid, collagen, polyorthoesters, and polylactic acid alone or with a wax, or other materials well known in the art. Methods for the preparation of such formulations are generally known to those skilled in the art. See, e.g., Sustained and Controlled Release Drug Delivery Systems, J. R. Robinson, ed., Marcel Dekker, Inc., New York, 1978.

In one embodiment, the compounds of the present invention may be formulated to ensure proper distribution in vivo. Pharmaceutically acceptable carriers for parenteral administration include sterile aqueous solutions or dispersions and sterile powders for the extemporaneous preparation of sterile injectable solutions or dispersion. The use of such media and agents for pharmaceutically active substances is known in the art. Except insofar as any conventional media or agent is incompatible with the active compound, use thereof in the pharmaceutical compositions of the present invention is contemplated. Supplementary active compounds may also be incorporated into the compositions.

Pharmaceutical compositions for injection must typically be sterile and stable under the conditions of manufacture and storage. The composition may be formulated as a solution, micro-emulsion, liposome, or other ordered structure suitable to high drug concentration. The carrier may be an aqueous or non-aqueous solvent or dispersion medium containing for instance water, ethanol, polyols (such as glycerol, propylene glycol, polyethylene glycol, and the like), and suitable mixtures thereof, vegetable oils, such as olive oil, and injectable organic esters, such as ethyl oleate. The proper fluidity may be maintained, for example, by the use of a coating such as lecithin, by the maintenance of the required particle size in the case of dispersion and by the use of surfactants. In many cases, it will be preferable to include isotonic agents, for example, sugars, polyalcohols such as glycerol, mannitol, sorbitol, or sodium chloride in the composition. Prolonged absorption of the injectable compositions may be brought about by including in the composition an agent that delays antibody absorption, for example, monostearate salts and gelatin. Sterile injectable solutions may be prepared by incorporating the active compound in the required amount in an appropriate solvent with one or a combination of ingredients e.g. as enumerated above, as required, followed by sterilization microfiltration. Generally, dispersions are prepared by incorporating the active compound into a sterile vehicle that contains a basic dispersion medium and the required other ingredients e.g. from those enumerated above. In the case of sterile powders for the preparation of sterile injectable solutions, examples of methods of preparation are vacuum drying and freeze-drying (lyophilization) that yield a powder of the active ingredient plus any additional desired ingredient from a previously sterile-filtered solution thereof.

Sterile injectable solutions may be prepared by incorporating the active compound in the required amount in an appropriate solvent with one or a combination of ingredients enumerated above, as required, followed by sterilization microfiltration. Generally, dispersions are prepared by incorporating the active compound into a sterile vehicle that contains a basic dispersion medium and the required other ingredients from those enumerated above. In the case of sterile powders for the preparation of sterile injectable solutions, examples of methods of preparation are vacuum drying and freeze-drying (lyophilization) that yield a powder of the active ingredient plus any additional desired ingredient from a previously sterile-filtered solution thereof.

Dosage regimens in the above methods of treatment and uses described herein are adjusted to provide the optimum desired response (e.g., a therapeutic response). For example, a single bolus may be administered, several divided doses may be administered over time or the dose may be proportionally reduced or increased as indicated by the exigencies of the therapeutic situation. Parenteral compositions may be formulated in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier. The specification for the dosage unit forms of the present invention are dictated by and directly dependent on (a) the unique characteristics of the active compound and the particular therapeutic effect to be achieved, and (b) the limitations inherent in the art of compounding such an active compound for the treatment of sensitivity in individuals.

The effective dosages and the dosage regimens for the anti-Sortilin antibodies depend on the disease or condition to be treated and may be determined by the persons skilled in the art. An exemplary, non-limiting range for a therapeutically effective amount of an antibody of the present invention is about 0.1-10 mg/kg/body weight, such as about 0.1-5 mg/kg/body weight, for example about 0.1-2 mg/kg/body weight, such as about 0.1-1 mg/kg/body weight, for instance about 0.15, about 0.2, about 0.5, about 1, about 1.5 or about 2 mg/kg/body weight.

A physician or veterinarian having ordinary skill in the art may readily determine and prescribe the effective amount of the pharmaceutical composition required. For example, the physician or veterinarian could start doses of the anti-Sortilin antibody employed in the pharmaceutical composition at levels lower than that required in order to achieve the desired therapeutic effect and gradually increase the dosage until the desired effect is achieved. In general, a suitable daily dose of a composition of the present invention will be that amount of the compound which is the lowest dose effective to produce a therapeutic effect. Such an effective dose will generally depend upon the factors described above. Administration may e.g. be intravenous, intramuscular, intraperitoneal, or subcutaneous, and for instance administered proximal to the site of the target. If desired, the effective daily dose of a pharmaceutical composition may be administered as two, three, four, five, six or more sub-doses administered separately at appropriate intervals throughout the day, optionally, in unit dosage forms. While it is possible for a compound of the present invention to be administered alone, it is preferable to administer the compound as a pharmaceutical composition as described above.

The labelled antibodies or antigen-binding fragments thereof of the invention can be used for diagnostic purposes to detect, diagnose, or monitor diseases or disorders. The invention provides for the detection or diagnosis of a neurodegenerative or cognitive disease or disorder, including but not limited to FTD, ALS or—proteinopathies such as Alzheimer's Disease (AD), comprising: (a) assaying the existence of pyroglutamate Aβ fragments in cells or tissue samples of a subject using one or more antibodies that specifically bind to Sortilin; and (b) comparing the level of the antigen with a control level, e.g. levels in normal tissue samples, whereby an increase in the assayed level of antigen compared to the control level of antigen is indicative of the disease or disorder, or indicative of the severity of the disease or disorder.

The antibodies or antigen-binding fragments thereof of the invention can be used to assay Sortilin or antigen-binding fragments of Sortilin in a biological sample using immuno-histochemical methods well-known in the art. Other antibody-based methods useful for detecting protein include immunoassays such as the enzyme linked immunoassay (ELISA) and the radioimmunoassay assay (RIA) and mesoscale discovery platform based assays (MSD). Suitable antibody labels may be used in such kits and methods, and labels known in the art include enzyme labels, such as alkaline phosphatase and glucose oxidase; radioisotope labels, such as iodine ($^{125}I$, $^{131}I$), carbon ($^{14}C$), sulfur ($^{35}S$), tritium ($^{3}H$), indium ($^{121}In$), and technetium ($^{99m}Tc$); and luminescent labels, such as luminol and luciferase; and fluorescent labels, such as fluorescein and rhodamine.

The presence of labeled anti-Sortilin antibodies or their Sortilin-binding fragments may be detected in vivo for diagnostic purposes. In one embodiment, diagnosis comprises: a) administering to a subject an effective amount of such labeled molecule; b) waiting for a time interval following administration to allow the labeled molecule to concentrate at sites (if any) of Aβ deposition and to allow for unbound labeled molecule to be cleared to background level; c) determining a background level; and d) detecting the labeled molecule in the subject, such that detection of labeled molecule above the background level is indicative that the subject has the disease or disorder, or is indicative of the severity of the disease or disorder. In accordance with such embodiment, the molecule is labeled with an imaging moiety suitable for detection using a particular imaging system known to those skilled in the art. Background levels may be determined by various methods known in the art, including comparing the amount of labeled antibody detected to a standard value previously determined for a particular imaging system. Methods and systems that may be used in the diagnostic methods of the invention include, but are not limited to, computed tomography (CT), whole body scan such as positron emission tomography (PET), magnetic resonance imaging (MRI), and sonography.

In a further aspect, the invention relates to an antibody, or antigen-binding fragment thereof, of the invention, for use in medicine.

In a further aspect, the invention relates to an antibody, or antigen-binding fragment thereof, of the invention, for use in treating a disease associated with decreased PGRN levels in the brain of a patient, In a further aspect, the invention relates to the use of the antibody, or antigen-binding fragment thereof, of the invention, in the manufacture of a medicament for treating a disease associated with decreased PGRN levels in the brain of a patient, In a further aspect, the invention relates to a method of preventing or treating a disease associated with decreased PGRN or decreased functional PGRN levels in the brain of a patient, comprising administering an effective dosage of an antibody of the invention, or an antigen-binding fragment thereof.

It is preferred that in the uses and methods of those aspects of the invention the disease is: FTD; ALS; or proteinopathies, such as AD.

Preferably, in the uses and methods of those aspects of the invention, the treatment is chronic, and is preferably for at least 2 weeks, such as at least for 1 month, 6, months, 1 year or more.

In a further aspect, the invention provides a kit comprising the antibody, or antigen-binding fragment thereof, of the invention.

TABLE 5

| Sequences | | | | |
|---|---|---|---|---|
| Antibody | 6003-028 | | | |
| Seq ID No | 1 | CDR | 1 | Heavy Chain |
| Seq ID No | 2 | CDR | 2 | Heavy Chain |
| Seq ID No | 3 | CDR | 3 | Heavy Chain |
| Seq ID No | 4 | CDR | 1 | Light Chain |
| Seq ID No | 5 | CDR | 2 | Light Chain |
| Seq ID No | 6 | CDR | 3 | Light Chain |
| Antibody | 6003-056 | | | |
| Seq ID No | 7 | CDR | 1 | Heavy Chain |
| Seq ID No | 8 | CDR | 2 | Heavy Chain |
| Seq ID No | 9 | CDR | 3 | Heavy Chain |
| Seq ID No | 10 | CDR | 1 | Light Chain |
| Seq ID No | 11 | CDR | 2 | Light Chain |
| Seq ID No | 12 | CDR | 3 | Light Chain |
| Antibody | 6003-1286 | | | |
| Seq ID No | 13 | CDR | 1 | Heavy Chain |
| Seq ID No | 14 | CDR | 2 | Heavy Chain |
| Seq ID No | 15 | CDR | 3 | Heavy Chain |
| Seq ID No | 16 | CDR | 1 | Light Chain |
| Seq ID No | 17 | CDR | 2 | Light Chain |
| Seq ID No | 18 | CDR | 3 | Light Chain |
| Antibody | 6003-030 | | | |
| Seq ID No | 19 | CDR | 1 | Heavy Chain |
| Seq ID No | 20 | CDR | 2 | Heavy Chain |
| Seq ID No | 21 | CDR | 3 | Heavy Chain |
| Seq ID No | 22 | CDR | 1 | Light Chain |
| Seq ID No | 23 | CDR | 2 | Light Chain |
| Seq ID No | 24 | CDR | 3 | Light Chain |
| Antibody | 6003-1277 | | | |
| Seq ID No | 25 | CDR | 1 | Heavy Chain |
| Seq ID No | 26 | CDR | 2 | Heavy Chain |
| Seq ID No | 27 | CDR | 3 | Heavy Chain |
| Seq ID No | 28 | CDR | 1 | Light Chain |
| Seq ID No | 29 | CDR | 2 | Light Chain |
| Seq ID No | 30 | CDR | 3 | Light Chain |
| Antibody | 6003-381 | | | |
| Seq ID No | 31 | CDR | 1 | Heavy Chain |
| Seq ID No | 32 | CDR | 2 | Heavy Chain |
| Seq ID No | 33 | CDR | 3 | Heavy Chain |
| Seq ID No | 34 | CDR | 1 | Light Chain |
| Seq ID No | 35 | CDR | 2 | Light Chain |
| Seq ID No | 36 | CDR | 3 | Light Chain |
| Antibody | 6003-083 | | | |
| Seq ID No | 37 | CDR | 1 | Heavy Chain |
| Seq ID No | 38 | CDR | 2 | Heavy Chain |
| Seq ID No | 39 | CDR | 3 | Heavy Chain |
| Seq ID No | 40 | CDR | 1 | Light Chain |
| Seq ID No | 41 | CDR | 2 | Light Chain |
| Seq ID No | 42 | CDR | 3 | Light Chain |
| Antibody | 6003-799 | | | |
| Seq ID No | 43 | CDR | 1 | Heavy Chain |
| Seq ID No | 44 | CDR | 2 | Heavy Chain |
| Seq ID No | 45 | CDR | 3 | Heavy Chain |
| Seq ID No | 46 | CDR | 1 | Light Chain |
| Seq ID No | 47 | CDR | 2 | Light Chain |
| Seq ID No | 48 | CDR | 3 | Light Chain |
| Antibody | 6003-910 | | | |
| Seq ID No | 49 | CDR | 1 | Heavy Chain |
| Seq ID No | 50 | CDR | 2 | Heavy Chain |
| Seq ID No | 51 | CDR | 3 | Heavy Chain |
| Seq ID No | 52 | CDR | 1 | Light Chain |
| Seq ID No | 53 | CDR | 2 | Light Chain |
| Seq ID No | 54 | CDR | 3 | Light Chain |
| Antibody | 6003-423 | | | |
| Seq ID No | 55 | CDR | 1 | Heavy Chain |
| Seq ID No | 56 | CDR | 2 | Heavy Chain |
| Seq ID No | 57 | CDR | 3 | Heavy Chain |
| Seq ID No | 58 | CDR | 1 | Light Chain |
| Seq ID No | 59 | CDR | 2 | Light Chain |
| Seq ID No | 60 | CDR | 3 | Light Chain |
| Antibody | 6003-822 | | | |
| Seq ID No | 61 | CDR | 1 | Heavy Chain |
| Seq ID No | 62 | CDR | 2 | Heavy Chain |
| Seq ID No | 63 | CDR | 3 | Heavy Chain |
| Seq ID No | 64 | CDR | 1 | Light Chain |
| Seq ID No | 65 | CDR | 2 | Light Chain |
| Seq ID No | 66 | CDR | 3 | Light Chain |

TABLE 5-continued

| Sequences | | | | |
|---|---|---|---|---|
| Antibody | 6003-886 | | | |
| Seq ID No | 67 | CDR | 1 | Heavy Chain |
| Seq ID No | 68 | CDR | 2 | Heavy Chain |
| Seq ID No | 69 | CDR | 3 | Heavy Chain |
| Seq ID No | 70 | CDR | 1 | Light Chain |
| Seq ID No | 71 | CDR | 2 | Light Chain |
| Seq ID No | 72 | CDR | 3 | Light Chain |
| Antibody | 6003-072 | | | |
| Seq ID No | 73 | CDR | 1 | Heavy Chain |
| Seq ID No | 74 | CDR | 2 | Heavy Chain |
| Seq ID No | 75 | CDR | 3 | Heavy Chain |
| Seq ID No | 76 | CDR | 1 | Light Chain |
| Seq ID No | 77 | CDR | 2 | Light Chain |
| Seq ID No | 78 | CDR | 3 | Light Chain |
| Antibody | 6003-900 | | | |
| Seq ID No | 79 | CDR | 1 | Heavy Chain |
| Seq ID No | 80 | CDR | 2 | Heavy Chain |
| Seq ID No | 81 | CDR | 3 | Heavy Chain |
| Seq ID No | 82 | CDR | 1 | Light Chain |
| Seq ID No | 83 | CDR | 2 | Light Chain |
| Seq ID No | 84 | CDR | 3 | Light Chain |
| Antibody | 6003-936 | | | |
| Seq ID No | 85 | CDR | 1 | Heavy Chain |
| Seq ID No | 86 | CDR | 2 | Heavy Chain |
| Seq ID No | 87 | CDR | 3 | Heavy Chain |
| Seq ID No | 88 | CDR | 1 | Light Chain |
| Seq ID No | 89 | CDR | 2 | Light Chain |
| Seq ID No | 90 | CDR | 3 | Light Chain |
| Antibody | 6003-408 | | | |
| Seq ID No | 91 | CDR | 1 | Heavy Chain |
| Seq ID No | 92 | CDR | 2 | Heavy Chain |
| Seq ID No | 93 | CDR | 3 | Heavy Chain |
| Seq ID No | 94 | CDR | 1 | Light Chain |
| Seq ID No | 95 | CDR | 2 | Light Chain |
| Seq ID No | 96 | CDR | 3 | Light Chain |
| Antibody | 6003-471 | | | |
| Seq ID No | 97 | CDR | 1 | Heavy Chain |
| Seq ID No | 98 | CDR | 2 | Heavy Chain |
| Seq ID No | 99 | CDR | 3 | Heavy Chain |
| Seq ID No | 100 | CDR | 1 | Light Chain |
| Seq ID No | 101 | CDR | 2 | Light Chain |
| Seq ID No | 102 | CDR | 3 | Light Chain |
| Antibody | 6003-972 | | | |
| Seq ID No | 103 | CDR | 1 | Heavy Chain |
| Seq ID No | 104 | CDR | 2 | Heavy Chain |
| Seq ID No | 105 | CDR | 3 | Heavy Chain |
| Seq ID No | 106 | CDR | 1 | Light Chain |
| Seq ID No | 107 | CDR | 2 | Light Chain |
| Seq ID No | 108 | CDR | 3 | Light Chain |
| Seq ID No | 109 | HC | | 6003-028 |
| Seq ID No | 110 | LC | | 6003-028 |
| Seq ID No | 111 | HC | | 6003-056 |
| Seq ID No | 112 | LC | | 6003-056 |
| Seq ID No | 113 | HC | | 6003-1286 |
| Seq ID No | 114 | LC | | 6003-1286 |
| Seq ID No | 115 | HC | | 6003-030 |
| Seq ID No | 116 | LC | | 6003-030 |
| Seq ID No | 117 | HC | | 6003-1277 |
| Seq ID No | 118 | LC | | 6003-1277 |
| Seq ID No | 119 | HC | | 6003-381 |
| Seq ID No | 120 | LC | | 6003-381 |
| Seq ID No | 121 | HC | | 6003-083 |
| Seq ID No | 122 | LC | | 6003-083 |
| Seq ID No | 123 | HC | | 6003-799 |
| Seq ID No | 124 | LC | | 6003-799 |
| Seq ID No | 125 | HC | | 6003-910 |
| Seq ID No | 126 | LC | | 6003-910 |
| Seq ID No | 127 | HC | | 6003-423 |
| Seq ID No | 128 | LC | | 6003-423 |
| Seq ID No | 129 | HC | | 6003-822 |
| Seq ID No | 130 | LC | | 6003-822 |
| Seq ID No | 131 | HC | | 6003-886 |
| Seq ID No | 132 | LC | | 6003-886 |
| Seq ID No | 133 | HC | | 6003-072 |
| Seq ID No | 134 | LC | | 6003-072 |
| Seq ID No | 135 | HC | | 6003-900 |
| Seq ID No | 136 | LC | | 6003-900 |
| Seq ID No | 137 | HC | | 6003-936 |

TABLE 5-continued

| Sequences | | | |
|---|---|---|---|
| Seq ID No | 138 | LC | 6003-936 |
| Seq ID No | 139 | HC | 6003-408 |
| Seq ID No | 140 | LC | 6003-408 |
| Seq ID No | 141 | HC | 6003-471 |
| Seq ID No | 142 | LC | 6003-471 |
| Seq ID No | 143 | HC | 6003-972 |
| Seq ID No | 144 | LC | 6003-972 |
| Seq ID No | 145 | Full human Sortilin sequence isoform 1 | |
| Seq ID No | 146 | "E Region" as identified by present invention | |
| Seq ID No | 147 | Sortilin "hSORTECDBAP" | |
| Seq ID No | 148 | Sortilin SORTECDBAP_hBACK | |
| Seq ID No | 149 | Sortilin SORTECDBAP_tetra | |
| Seq ID No | 150 | Sortilin SORTECDBAP_hB01-05 | |
| Seq ID No | 151 | Sortilin SORTECDBAP_hRIM | |
| Seq ID No | 152 | Sortilin SORTECDBAP_hB06-10 | |
| Seq ID No | 153 | Sortilin SORTECDBAP_hB12390 | |
| Seq ID No | 154 | Sortilin SORTECDBAP_hB45678 | |
| Seq ID No | 155 | Sortilin SORTECD HIS | |
| Seq ID No | 156 | HDX-MS construct | |

The listing or discussion in this specification of an apparently prior-published document should not necessarily be taken as an acknowledgement that the document is part of the state of the art or is common general knowledge.

Embodiments

As would be apparent from the text and the Examples the invention further relates to the below embodiments:

1. An antibody, or an antigen-binding fragment thereof, capable of specifically binding to Sortilin and inhibiting binding of PGRN to Sortilin.
2. The antibody, or antigen-binding fragment thereof, according to Embodiment 1, wherein the antibody comprises or consists of an intact antibody.
3. The antibody, or antigen-binding fragment thereof, according to Embodiment 1 or 2, wherein the antigen-binding fragment comprises or consists of an antigen-binding fragment selected from the group consisting of: an Fv fragment (e.g. single chain Fv or a disulphide-bonded Fv); a Fab-like fragment (e.g. Fab fragment or F(ab')2 fragment); and a domain antibody (e.g. a single VH variable domain or VL variable domain).
4. The antibody, or antigen-binding fragment thereof, according to any preceding Embodiment, wherein the antibody is selected from the group consisting of: an antibody of subtype IgG1, IgG2, IgG3 or IgG4.
5. The antibody, or antigen-binding fragment thereof, according to any preceding Embodiment, wherein said antibody or antigen-binding fragment thereof binds specifically to the E region of Sortilin as defined in SEQ ID NO: 146.
6. The antibody, or antigen-binding fragment thereof, according to any preceding Embodiment, wherein said antibody or fragment thereof binds specifically to at least 3 consecutive amino acids, such as 4, 5, 6 or 7 consecutive amino acids, of the E region of Sortilin as defined in SEQ ID NO: 146.
7. The antibody, or antigen-binding fragment thereof, according to any preceding Embodiment, wherein the antibody or antigen-binding fragment exhibits one or more of the following properties:
   (i) a binding affinity ($K_D$) for Sortilin of between 0.5-10 nM, such as 1-5 nM or 1-2 nM, or even higher such as between 0.5 μM and 500 μM
   (ii) capability to reduce and/or inhibit clearance of PGRN by Sortilin-expressing cells;
   (iii) capability to reduce and/or inhibit the endocytosis of PGRN by Sortilin-expressing cells;
   (iv) capability to increase the amount and/or concentration of PGRN in the plasma in human-Sortilin-expressing knock-in mice.
8. The antibody, or antigen-binding fragment thereof, according to Embodiment 5, which is human or humanized.
9. The antibody, or antigen-binding fragment thereof, according to Embodiment 6, which is human or humanized.
10. The antibody, or antigen-binding fragment thereof, according to any previous Embodiment, wherein the antibody or antigen-binding fragment thereof is human or is humanized.
11. The antibody, or antigen-binding fragment thereof, according to any preceding Embodiment, comprising a light chain variable domain comprising one or more of the CDR 1-3 Light Chain as listed for each of the antibodies defined in Table 5, or an amino acid sequence having no more than 4 amino acid differences, or no more than 3 amino acid differences, or no more than 2 amino acid differences, or no more than 1 amino acid difference.
12. The antibody, or antigen-binding fragment thereof, according to Embodiment 11, comprising a light chain variable domain comprising the CDR 1-3 Light Chain as listed for each of the antibodies defined in Table 5.
13. The antibody, or antigen-binding fragment thereof, according to Embodiment 11 or 12, comprising a light chain variable domain comprising or consisting of the amino acid sequence VL as listed for each of the antibodies defined in Table 5.
14 The antibody, or antigen-binding fragment thereof, according to any of Embodiments 11 to 13, comprising a light chain comprising or consisting of the amino acid sequence of VL as listed for each of the antibodies defined in Table 5.
15. The antibody, or antigen-binding fragment thereof, according to any preceding Embodiment, comprising a heavy chain variable domain comprising one or more CDR 1-3 Heavy Chain as listed for each of the antibodies defined in Table 5, or an amino acid sequence having no more than 4 amino acid differences, or no more than 3 amino acid differences, or no more than 2 amino acid differences, or no more than 1 amino acid difference.
16. The antibody, or antigen-binding fragment thereof, according to Embodiment 15, comprising a heavy chain variable domain comprising the CDR 1-3 Heavy Chain as listed for each of the antibodies defined in Table 5.
17 An antibody, or antigen-binding fragment thereof, according to Embodiment 15 or 16 comprising a heavy chain variable domain comprising or consisting of the amino acid sequence of VH as listed for each of the antibodies defined in Table 5.
18. The antibody, or antigen-binding fragment thereof, according to any of Embodiments 15 to 17, comprising a heavy chain comprising or consisting of the amino acid sequence VL as listed for each of the antibodies defined in Table 5.
19. The antibody, or antigen-binding fragment thereof, according to any preceding embodiment, comprising a light chain variable domain comprising or consisting of the amino acid sequence of VL as listed for each of the antibodies defined in Table 5, and a heavy chain variable domain comprising or consisting of the amino acid sequence of VH as listed for each of the antibodies defined in Table 5.

20. The antibody, or antigen-binding fragment thereof, according to any preceding embodiment, comprising a light chain comprising or consisting of the amino acid sequence of VL as listed for each of the antibodies defined in Table 5, and a heavy chain comprising or consisting of the amino acid sequence of VH as listed for each of the antibodies defined in Table 5.
21. The antibody, or antigen-binding fragment thereof, according to any preceding Embodiment, wherein said antibody or antigen-binding fragment thereof competes with the antibody or antigen-binding fragment thereof defined in Embodiment 20 for binding to Sortilin.
22. The antibody, or antigen-binding fragment thereof, according to any preceding Embodiment, wherein the antibody or antigen-binding fragment comprises an Fc region.
23. The antibody, or antigen-binding fragment thereof, according to any preceding Embodiment, wherein the antibody or antigen-binding fragment further comprises a moiety for increasing in vivo half-life.
24. The antibody, or antigen-binding fragment thereof, according to Embodiment 22, wherein the moiety for increasing the in vivo half-life is selected from the group consisting of polyethylene glycol (PEG), human serum albumin, glycosylation groups, fatty acids and dextran.
25. The antibody, or antigen-binding fragment thereof, according to any preceding Embodiment, wherein the antibody or antigen-binding fragment further comprises a detectable moiety.
26. The antibody, or antigen-binding fragment thereof, according to Embodiment 25, wherein the detectable moiety is selected from the group consisting of: a fluorescent label; a chemiluminescent label; a paramagnetic label; a radioisotopic label; or an enzyme label.
27. The antibody, or antigen-binding fragment thereof, according to Embodiment 25 or 26, wherein the detectable moiety comprises or consists of a radioisotope.
28. The antibody, or antigen-binding fragment thereof, according to Embodiment 26 or 27, wherein the radioisotope is selected from the group consisting of $^{99m}$Tc, $^{111}$In, $^{67}$Ga, $^{68}$Ga, $^{72}$As, $^{89}$Zr, $^{123}$I and $^{201}$Tl.
29. The antibody, or antigen-binding fragment thereof, according to Embodiment 25, wherein the detectable moiety comprises or consists of a paramagnetic isotope.
30. The antibody, or antigen-binding fragment thereof, according to Embodiment 29 wherein the paramagnetic isotope is selected from the group consisting of 157Gd, 55 Mn, 162Dy, 52Cr and 56Fe.
31 The antibody, or antigen-binding fragment thereof, according to any of Embodiments 25 to 30, wherein the detectable moiety is detectable by an imaging technique such as SPECT, PET, MRI, optical or ultrasound imaging.
32 The antibody, or antigen-binding fragment thereof, according to any of Embodiments 25 to 31, wherein the detectable moiety is joined to the antibody or antigen-binding fragment thereof indirectly, via a linking moiety.
33. The antibody, or antigen-binding fragment thereof, according to Embodiment 32 wherein the linking moiety is selected from the group consisting of: derivatives of 1,4,7,10-tetraazacyclododecane-1,4,7,10, tetraacetic acid (DOTA); deferoxamine (DFO); derivatives of diethylenetriaminepentaacetic avid (DTPA); derivatives of S-2-(4-Isothiocyanatobenzyl)-1,4,7-triazacyclononane-1,4,7-triacetic acid (NOTA); and derivatives of 1,4,8,11-tetraazacyclododecan-1,4,8,11-tetraacetic acid (TETA).
34 An isolated nucleic acid molecule encoding an antibody or antigen-binding fragment thereof as defined in any of Embodiments 1-33.
35. A nucleic acid molecule according to Embodiment 34 wherein the molecule is a cDNA molecule.
36. A vector comprising a nucleic acid molecule as defined in Embodiment 34 or 35.
37. A recombinant host cell comprising a nucleic acid molecule as defined in any of Embodiments 34-36.
38. A method for producing an antibody or antigen-binding fragment as defined in any of Embodiments 1-33, the method comprising culturing a host cell as defined in Embodiment 37 under conditions which permit expression of the encoded antibody or antigen-binding fragment thereof.
39. A preparation comprising the antibody or antigen-binding fragment thereof according to any one of the previous Embodiments, wherein said preparation is substantially free of naturally-arising antibodies that are either not capable of binding to Sortilin or that do not materially alter an anti-Sortilin functionality of the preparation, said functionality being selected from the group consisting of:
   (i) a binding affinity ($K_D$) for Sortilin;
   (ii) a capability to reduce and/or inhibit clearance of PGRN by Sortilin-expressing cells;
   (iii) a capability to reduce and/or inhibit the endocytosis of PGRN by Sortilin-expressing cells;
   (iv) a capability to increase the amount and/or concentration of PGRN in the plasma in human-Sortilin-expressing knock-in mice; and/or
   (v) a capability, when administered chronically, to provide treatment of frontotemporal dementia (FTD) and/or amyotrophic lateral sclerosis (ALS).
40. A preparation comprising the monoclonal antibody or antigen-binding fragment thereof according to any one of the previous Embodiments, wherein said monoclonal antibody possesses a structural change in its amino acid sequence, relative to the structure of a naturally-occurring anti-Sortilin antibody, wherein said structural change causes said monoclonal antibody to exhibit an altered functionality relative to the functionality exhibited by said naturally-occurring anti-Sortilin antibody, wherein said functionality is:
   (i) a binding affinity (KD) for Sortilin;
   (ii) a capability to reduce and/or inhibit clearance of PGRN by Sortilin-expressing cells;
   (iii) a capability to reduce and/or inhibit the endocytosis of PGRN by Sortilin-expressing cells;
   (iv) a capability to increase the amount and/or concentration of PGRN in the plasma in human-Sortilin-expressing knock-in mice; and/or
   (v) a capability, when administered chronically, to provide treatment of frontotemporal dementia (FTD) and/or amyotrophic lateral sclerosis (ALS).
41. A pharmaceutical composition comprising an antibody, or antigen-binding fragment thereof, as defined in any of Embodiments 1-33, or the preparation of any one of embodiments 39-40, and a pharmaceutically-acceptable carrier.

42 The antibody, or antigen-binding fragment thereof, as defined in any of Embodiments 1-33, or the preparation of any one of embodiments 39-40, for use in medicine.

43. The antibody, or antigen-binding fragment thereof, as defined in any of Embodiments 1-33, or the preparation of any one of embodiments 39-40, for use in preventing and/or treating a disease associated with decreased PGRN or decreased functional PGRN levels in the brain of a patient.

44 Use of an antibody, or antigen-binding fragment thereof, as defined in any of Embodiments 1-33, or the preparation of any one of embodiments 39-40, in the manufacture of a medicament for preventing and/or treating a disease associated with decreased PGRN levels in the brain of a patient.

45. The antibody or antigen-binding fragment thereof for use according to Embodiment 43, or the use according to Embodiment 44, wherein the disease is selected from the group consisting of: FTD; ALS; proteinopathies, such as AD, PD.

46. A method of preventing or treating a disease associated with decreased PGRN levels in the brain of a patient, comprising administering an effective dosage of an antibody or a fragment thereof as defined in any of Embodiments 1-33, the preparation of any one of Embodiments 39-40, or the pharmaceutical composition of Embodiment 41.

47 The antibody, or antigen-binding fragment thereof, for use according to Embodiment 43, or the use according to Embodiment 44, or the method according to Embodiment 46, wherein the disease is selected from the group consisting of: FTD; ALS; or proteinopathies, such as AD, PD.

48. The antibody, or antigen-binding fragment thereof, for use; or the use; or the method according to Embodiment 46 or 47, wherein the treatment is chronic.

49. The antibody, or antigen-binding fragment thereof, for use; or the use; or the method, according to Embodiment 48, wherein the chronic treatment is for at least 2 weeks, such as at least for 1 month, 6, months, 1 year or more 50. The antibody, or antigen-binding fragment thereof, as defined in any of Embodiments 1-33, the preparation of any one of Embodiments 39-40, or the pharmaceutical composition of Embodiment 41, which is capable of specifically binding to Sortilin, but which binding does not inhibit or substantially inhibit the binding of neurotensin or AF38469 (Schrøder T J et al., Bioorg Med Chem Lett. 2014 Jan. 1; 24(1):177-80) to Sortilin.

51. A kit comprising the antibody, or antigen-binding fragment thereof, as defined in any of Embodiments 1-33, the preparation, as defined in any one of Embodiments 39-40, or the pharmaceutical composition as defined in Embodiment 41.

Preferred, non-limiting examples which embody certain aspects of the invention will now be described, with reference to the accompanying FIGURES.

EXAMPLES

Examples 1-3 describe the generation of sortilin constructs Example 1 discloses the shuffle constructs. Example 2 discloses the expression of sortilin constructs. Example 3 discloses the purification of sortilin constructs. Examples 4-6 describe the generation of sortilin antibodies Example 4 discloses the immunization and the hybridomas. Example 5 discloses the sequence analysis. Example 6 discloses the purification of antibodies.

Examples 7-11 describe the characterization of sortilin antibodies

Example 7 discloses the binding to sortilin. Example 8 discloses the cross blocking ability of Sortilin antibodies. Example 9 discloses extracellular PGRN levels in iPSCs Example 10 discloses plasma PGRN levels

Example 1

For use in both the hybridoma screening process and as a diversification of the panel of antibodies, so called 'shuffle constructs" were designed, constructed and produced, making a set of chimeric sortilin molecules containing amino acid sequences derived from both human sortilin and a distantly related species (tetraodon) with significantly reduced sequence homology. The rationale being that the overall sortilin structure and functionality of these chimeric constructs would be retained but that loss of binding of antibodies to certain chimeric constructs would indicate the involvement of the specific exchanged regions in binding. Soluble extracellular region (ECD, aa 1-755) constructs were tagged with either a BAP tag (biotin acceptor peptide), enabling the "in vitro" biotinylation of the proteins by co-expression of biotin ligase or a His tag, enabling easy purification. Expression vectors encoding the following proteins were prepared: SORT-ECDBAP, SORT-ECDBAP-hB01-05, SORT-ECDBAPhB06-10, SORT-ECDBAP-hB12390, SORT-ECDBAP-hB45678, SORT-ECDBAPtetra, SORT, SORT-tetra.

Figure 2A:
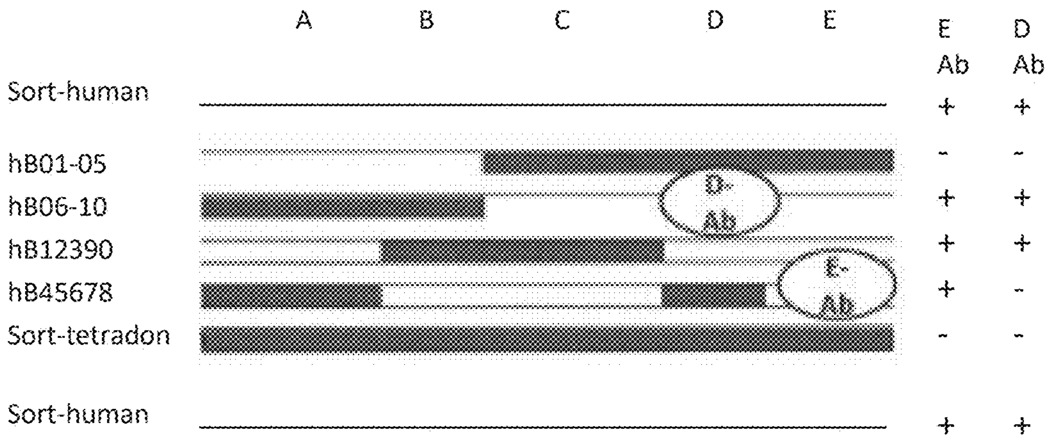
Figure 2B:
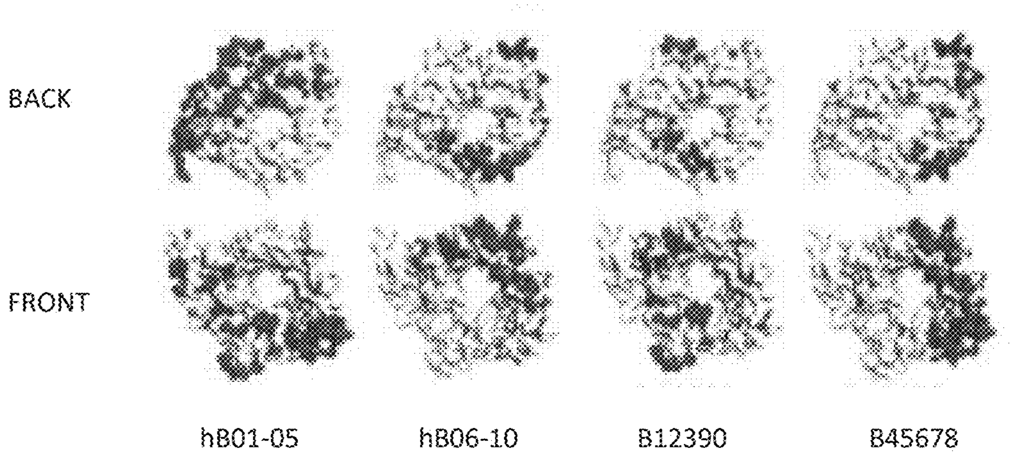

The Sortilin sequences can be found in SEQ ID NOs: 147-155 and FIG. 2 shows schematic presentation of the region assignment of antibodies based on binding to Sortilin shuffle constructs.

Example 2

In the case of antibody expression, the appropriate heavy chain and light chain vectors, as described in Examples 4, 5 and 6, were co-expressed in HEK-293F cells.

Example 3: Purification of His-Tagged Sortilin

SORTECDHis was expressed in HEK-293F cells. The His-tag in the proteins enables purification with immobilized metal affinity chromatography. In this process NiNTA Superflow Cartridge (Qiagen) is equilibrated with 50 mM $NAH_2PO_4$, 300 mM NaCl and 10 mM Imidazole pH 8.0. Column is loaded with His tagged protein with a residence time of 1 minute. Column is washed with 50 mM $NAH_2PO_4$, 300 mM NaCl and 20 mM Imidazole pH 8.0. Protein is eluted with 50 mM $NAH_2PO_4$, 300 mM NaCl and 250 mM Imidazole pH 8.0. Subsequently the protein is dialyzed to PBS using a Slide-A-Lyzer with a cut off of 10.000 mwco (Thermo Scientific). After dialyzing the protein is sterile filtered using a 0.2 micron SFCA filter (Thermo Scientific). Clones were characterized for sortilin mRNA expression using qPCR. Highest expressing clones were than analyzed by FACS (Guava, Millipore) using an anti-sortilin polyclonal antibody (Polyclonal Goat Sortilin Biotinylated Ab, Cat. No: BAF2934 (R & D Systems)) to determine the surface expressed levels of Sortilin.

Example 4

A—Immunization Procedure of Transgenic Mice

Antibodies HuMab Sortilin were derived from the immunizations of HuMAb mouse strains HCo12, HCo17, HCo20, HCo12-BALB/c, HCo17-BALB/c and HCo20-BALB/c (human monoclonal antibody; Medarex Inc., San Jose, CA, USA), These mice are double knock out for the mouse immunoglobulin (lg) heavy and mouse kappa light chain, which substantially inactivate the expression of antibodies that are completely murine. The various mouse strains were made transgenic by the insertion of human Ig heavy and human Ig kappa light chain loci and differ in the number of human VH (variable domain of heavy chain) and VL (variable domain of light chain) genes. HCo12-BALB/c mice were derived by crossbreeding with KCo5-BALB/c (kappa light chain transgenic) mice.

48 mice were immunized alternating intraperitoneally (IP) with 20 μg SORTECDHis (SEQ ID NO: 155) and subcutaneously (SC, at the tail base) with the same protein, with an interval of 14 days. A maximum of eight immunizations were performed, 4 IP and 4 SC.

In one protocol, the first immunization was performed with SORTECDHis in complete Freund's adjuvant (CFA; Difco Laboratories, Detroit, MI, USA), the following immunizations in incomplete Freund's adjuvant (IFA). A second protocol used SAS as an adjuvant in all immunization steps. When serum titers were found to be sufficient (dilution of serum of 1/50 or lower found positive in antigen specific screening assay on at least two sequential, biweekly, screening events), mice were additionally boosted twice intravenously (IV) with 10 μg SORTECDHis protein in 100 μL PBS, four and three days before fusion.

B—HuMab Hybridoma—Generation

HuMAb mice with sufficient antigen-specific titer development as defined above were sacrificed and the spleen and lymph nodes flanking the abdominal aorta and caval vein were collected. Fusion of splenocytes and lymph node cells with a mouse myeloma cell line was done by electrofusion using a CEEF 50 Electrofusion System (Cyto Pulse Sciences, Glen Burnie, MD, USA), essentially according to the manufacturer's instructions. Fused cells were seeded in fusion medium containing 10% Fetal Clone I Bovine serum (Perbio), 1 mM sodium pyruvate (Cambrex), 0.5 U/mL penicillin, 0.5 U/mL streptomycin (Cambrex), 50 M 2-mercaptoethanol (Invitrogen), 600 ng/ml interleukin 6 (IL-6) (Strathmann), 1×HAT (Sigma) and 0.5 mg/mL kanamycin (Invitrogen) in HyQ mADCF-Mab (Perbio). After ten days, supernatant was harvested and cells were refreshed with harvest medium, containing 10% Fetal Clone I Bovine serum, 0.5 U/mL penicillin, 0.5 U/mL streptomycin, 600 ng/ml IL-6 and 1×proHT (Cambrex) in HyQ mADCF-Mab. Supernatants of the hybridoma cultures were screened by primary screening assays and streptavidin beads coupled to SORTECDBAP (SEQ ID NO 147), SORTECDBAPhB06-10 (SEQ ID NO 152), SORTECDBAPhB12390 (SEQ ID NO 153), to detect hybridomas producing human (or chimeric) anti-Sortilin antibodies. Hybridoma cells from the best primary wells were seeded in semisolid medium made from 40% CloneMedia (Genetix, Hampshire, UK) and 60% HyQ 2× complete medium (Hyclone, Waltham, USA). For each primary well, a well of a Genetix black 6-well plate was seeded. From each well, 25 sub clones were picked, using the ClonePix system (Genetix). The sub clones were picked in harvest medium. After seven days, the supernatants of the sub clones were screened again for Sortilin-specific human IgG binding and the human IgG concentration was measured using Octet 384red (Fortebio, Menlo Park, USA). From each primary well, the best sub clone was selected and expanded in expansion medium containing only 600 ng/ml IL-6, 0.5 U/mL penicillin, 0.5 U/mL streptomycin and 1×proHT. The sub clones were expanded from one 96-well plate well to one 24-well plate well to four 24-well plate wells to six 6-well plate wells. Clones derived by this process were designated as primary clones (PC).

The anti-sortilin HuMab antibodies of the invention were identified and subjected to sequence analysis.

Example 5: Sequence Analysis of the Sortilin-Specific HuMab Variable Domains and Cloning in Expression Vectors Total RNA was prepared from 0.2 to 5×106 hybridoma cells and 5'-RACE-Complementary DNA (cDNA) was prepared from 100 ng total RNA, using the SMART RACE cDNA Amplification kit (Clontech), according to the manufacturer's instructions. VH and VL coding regions were amplified by PCR and cloned directly, in frame, in the p33G1f and p33Kappa expression vectors (containing the human IgG1/kappa constant domain encoding sequences), by ligation independent cloning (Aslanidis, C. and P. J. de Jong, Nucleic Acids Res 1990; 18(20): 6069-74). For each antibody, 16 VL clones and 16 VH clones were sequenced. Clones with a correct Open Reading Frame (ORF) were selected for further study and expression. Vectors of all combinations of heavy chains and light chains were transiently co-expressed in Freestyle™ 293-F cells using 293fectin.

The resulting sequences are shown in the Sequence Listing (SEQ ID NOs: 1-144) herein. CDR sequences were defined according to the pub-lished guidelines.

Example 6: Purification of Antibodies

Culture supernatant was filtered over 0.2 μm dead-end filters, loaded on 5 mL Protein A columns (rProtein A FF, Amersham Bioscience) and eluted with 0.1 M citric acid-NaOH, pH 3. The eluate was immediately neutralized with 2 M Tris-HCl, pH 9 and dialyzed to 12.6 mM $NaH_2PO_4$, 140 mM NaCl, pH 7.4 (B. Braun), O/N (over night). After dialysis, samples were sterile-filtered over 0.2 μm dead-end filters. Purity was determined by SDS-PAGE and concentration was measured by nephelometry and absorbance at 280 nm. Purified antibodies were aliquoted and stored at 80° C. Once thawed, purified antibody aliquots were kept at 4° C. Mass spectrometry was performed to identify the molecular mass of the antibody heavy and light chains expressed by the hybridomas.

Example 7: Affinity of Sortilin Specific HuMab to Recombinant Extracellular Region of Sortilin Binding kinetics of anti-Sortilin HuMab antibodies to Sortilin were determined using Octet 384RED (Fortebio, Menlo Park, USA). HuMab solutions of 2 μg/ml were made by dilution in sample diluent (ForteBio, art. No. 18-5028). Prot A sensors (ForteBio, art. no. 18-0004) were prewetted with kinetics buffer (1:10 sample diluent in PBS) for at least 600 seconds. Subsequently sensors were immobilized with HuMab solution for 600 seconds. A baseline response was obtained by dipping in kinetics buffer for 120 seconds. Association of SORTECD constructs was performed during a 1000 seconds incubation. This was followed by dissociation in kinetics buffer for 100 seconds. After dissociation, sensors were regenerated (10 mM Glycine pH 1.0) and neutralized (kinetics buffer) 3 times for 5 seconds. All HuMab were analysed using four concentrations of SORTECD constructs (10, 5, 2.5 and 1.25 μg/ml). A molecular weight of 76.8 kDA was used for SORTECDHis. Data was fitted with ForteBio Analysis 6.4 software, using a global full fit. Results are shown in FIG. 3.

Example 8: Antibody Cross Block of Anti-Sortilin HuMantibodies

Antibody cross-block studies were performed using Octet 384RED (Fortebio, Menlo Park, USA). HuMab antibody solutions of 2 μg/ml were made by dilution in sample diluent (ForteBio, art. No. 18-5028). Amine reactive sensors (ForteBio, art. no. 18-0008) were used for immobilization of HuMantibodies. Prior to coupling to amine reactive sensors, HuMantibodies were diluted in MES pH 6.0 buffer (18-5027). Coupling was performed at 30° C. and 1000 rpm as follows: Amine reactive sensors were prewet in PBS and subsequently activated with EDC/NHS (ForteBio. Art. no. 18-1033/18-1034) activation solution (according to manufacturer's instruction) for 300 seconds. Activated sensors were immobilized with HuMantibodies during 600 seconds. Immobilized sensors were quenched for remaining amine reactivity with Ethanolamine (ForteBio, cat no. 18-1039). After quenching sensors were placed in PBS until use. Cross block analysis starts with establishing a baseline response at 30° C. and 1000 rpm. Baseline response was obtained by dipping in sample diluent for 120 seconds. Association of SORTECDHis was performed during 300 seconds directly followed by association of HuMab for 300 seconds. After association of HuMab, sensors were regenerated (10 mM Glycine pH 1.0) and neutralized (sample diluent) 3 times for 5 seconds. Data was processed using ForteBio Analysis 6.4 software. Antibodies were grouped based on their binding profiles on the different Sortilin shuffle constructs (FIG. 2 and FIG. 3). To confirm that all the antibodies from Region E bind to the same region on human wild type Sortilin ECD, their ability to block each other's binding to the wild type human Sortilin ECD was characterised in a cross blocking study using the Octet384 red. For example, when antibodies from the same region were tested, the primary antibody would block binding of the secondary antibody and vice versa. Whereas, when antibodies from different regions were tested, there would be no cross blocking as only one region is blocked by the primary antibody and the remaining regions are available for the secondary antibody to bind. FIG. 4 shows that 22 out of 26 antibodies from E domain cross block all antibodies from the group and the remaining 4 antibodies cross block 20 out of 26 antibodies which confirms that most of these antibodies bind in the same region on sortilin and rest of them have overlapping binding sites and/or bind in close proximity in the E region. This confirms classification of the antibodies to Region E based on shuffle constructs. Further, these data also confirm that the chimeric Sortilin constructs retain similarity to the native human wild type Sortilin ECD.

Example 9

ELISA Assay for Extracellular PGRN in iPSCs

Figure 5:
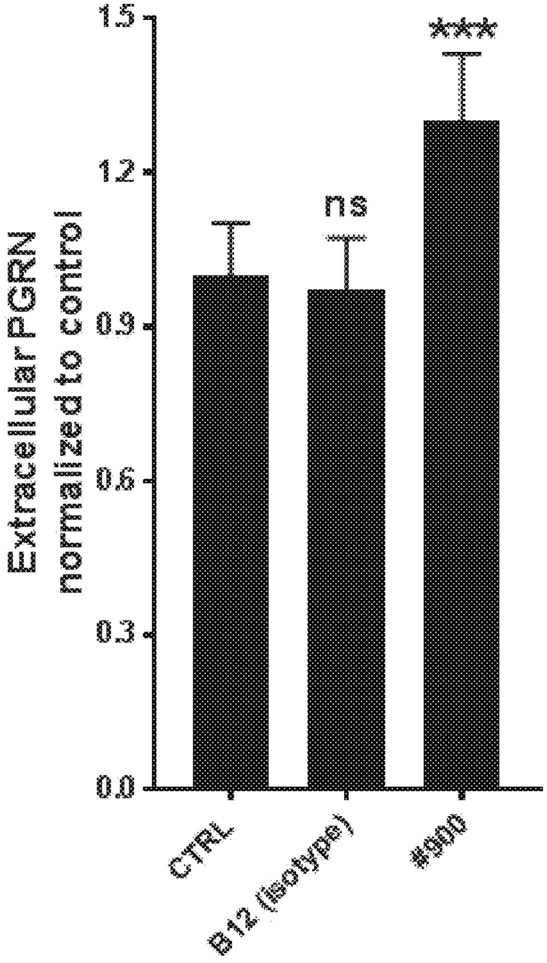
FIG. 5 shows the effect of Sortilin antibodies on extracellular PGRN in neuronal differentiated induced pluripotent stem cells (iPSCs) generated from an apparently heathy male (18 years). (Example 9)

The sortilin E-region antibody 900 increased PGRN levels whereas the control antibody B12 did not affect extracellular progranulin levels. The assay was performed with growth factor matured iPSC neurons plated into 96 wells plate. Antibodies were added to the cell media. The culture media was collected after 72 hrs exposure and analysed by human PGRN ELISA (Biovendor) and samples analysed according to the manufacturer's instructions. Sortilin human antibody 900 increased PGRN levels in the media collected from the iPSC neurons, whereas no effect was seen of the control antibody B12 (FIG. 5). Media with antibodies not exposed to the cells showed no signal in the PGRN ELISA. CellTiter-Glo Luminescent cell viability assay (Promega) showed no effect on viability of antibody applications. Data is presented as mean±SD. Data was analyzed by one-way Anova followed by Dunnett's analysis ***$p<0.001$.

The iPSC line was generated from human fibroblasts sampled from an apparently heathy male (18 years) by reprogramming according to a non-integrative method as described in Rasmussen et al. (Stem Cell Reports. 2014 Sep. 9; 3(3):404-13). The clone named NHDF K1_shp53 (deposited in the European Bank of induced Pluripotent Stem Cells as BIONi010-A) was used. The iPSCs were cultured in monolayer in mTeSR1 media (Stemcell Technologies) on matrigel (BD Biosciences). Neuronal differentiation was initiated day 0 by dual SMAD inhibition (100 nM LDN and 10 μM SB431542 in N3 media (50% DMEM/F12+50% Neurobasal media supplemented with 0.5% N2, 1% B27 with RA, 0.5 mM GlutaMAX-I, 0.5% NEA, 50 UM 2-mercaptoethanol and 2.5 μg/mL insulin) of iPSCs plated at high density. The cells were split at day 12 and from now on plated on poly-L-ornithine/laminin. LDN and SB431542 were withdrawn from day 13. From this time point, the cells were split approximately every 5 day until the neuronal progenitor cells (NPCs) were frozen day 21 to generate a NPC bank. These NPCs were thawed, allowed to proliferate for approximately 4 days before re-plating day 25 and subjecting to day final maturation medium (N3 with 20 ng/ml BDNF, 10 ng/mLGDNF, 500 μM db-CAMP, 200 μM ascorbic acid) from day 26. Day 32, the cells were subjected to final re-plating into assay plates in maturation medium. FACS studies have confirmed surface expression of the sortilin receptor on iPSC neurons from other lines generated in a similar way. Antibodies were applied day 56 and samples collected day 59.

Example 10 Effect of Antibodies on Plasma PGRN Levels in Mice

To analyze the effect of antibodies on PGRN levels in plasma, humanized Sortilin KI mice were given a single injection (10 mg/kg) of the sortilin antibody or isotype control by subcutaneous injections. The animals were anaesthetized and sacrificed 48 hrs time points after dosing and plasma PGRN levels determined by ELISA.

Mice were anaesthetized with 0.4 ml Avertin IP and heart blood was collected and transferred to a 500 μl kEDTA vial. Samples were kept on ice until centrifuged at 3600G for 15 min at 4° C. The plasma was pipetted in to a micronic vial and frozen at −20° C. PGRN in the samples was measured using PGRN ELISA kit (Adipogen) as per the manufacturer's instructions.

Figure 6:
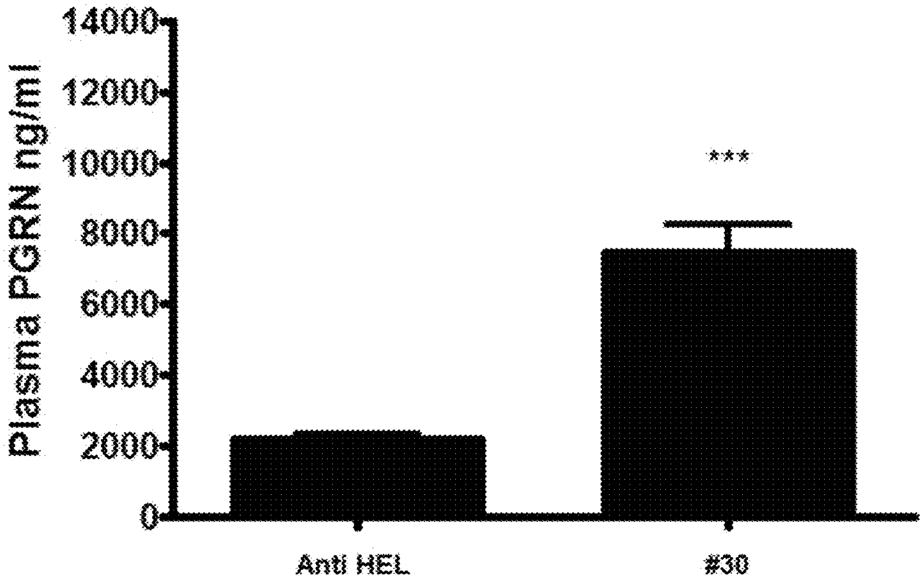
FIG. 6 shows plasma PGRN levels in human Sortilin Knock in (KI) mice treated with Sortilin human E-Domain binding antibody (Example 10). Antibody #30 increases plasma PGRN levels as compared to isotype control antibody, anti-HEL, treated mice.

Mice treated with Sortilin humab, #30, showed an increase in plasma PGRN levels after 48 hrs compared to Anti-HEL, isotype control antibody. Results can be seen in FIG. 6.

Example 11

Figure 7A:
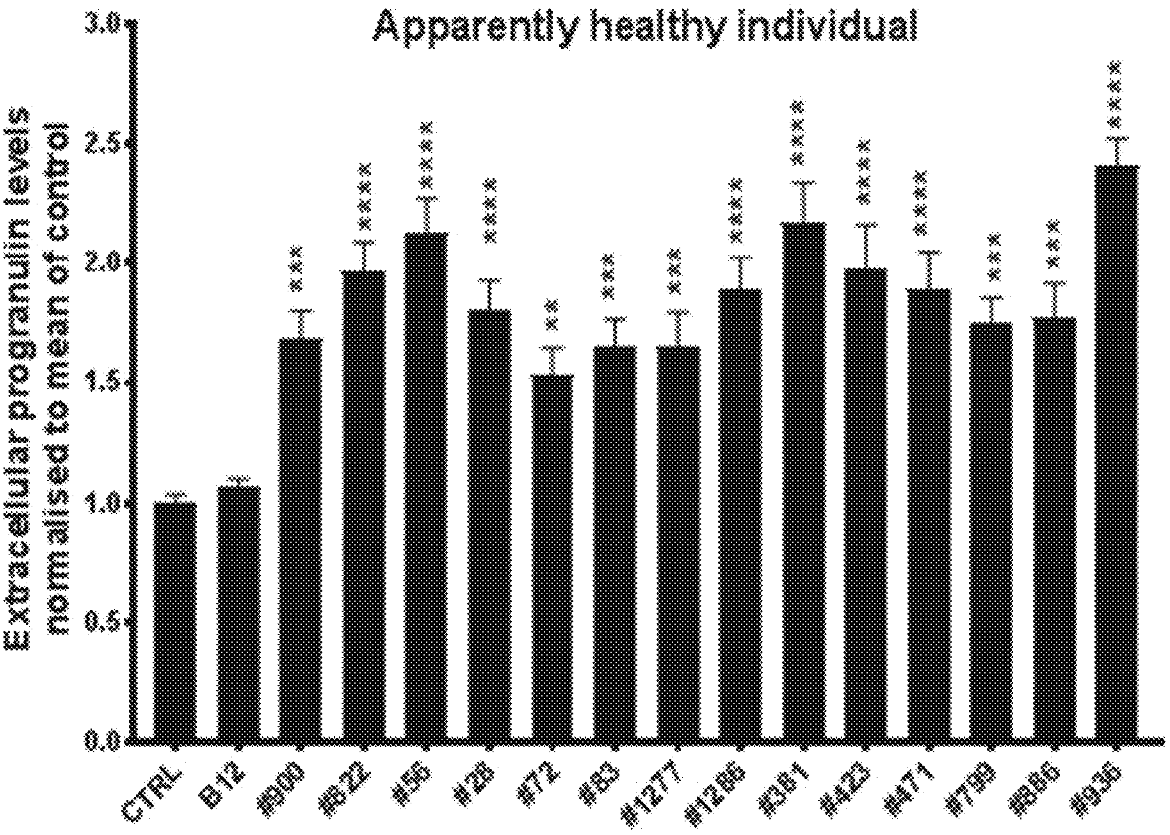
Figure 7B:
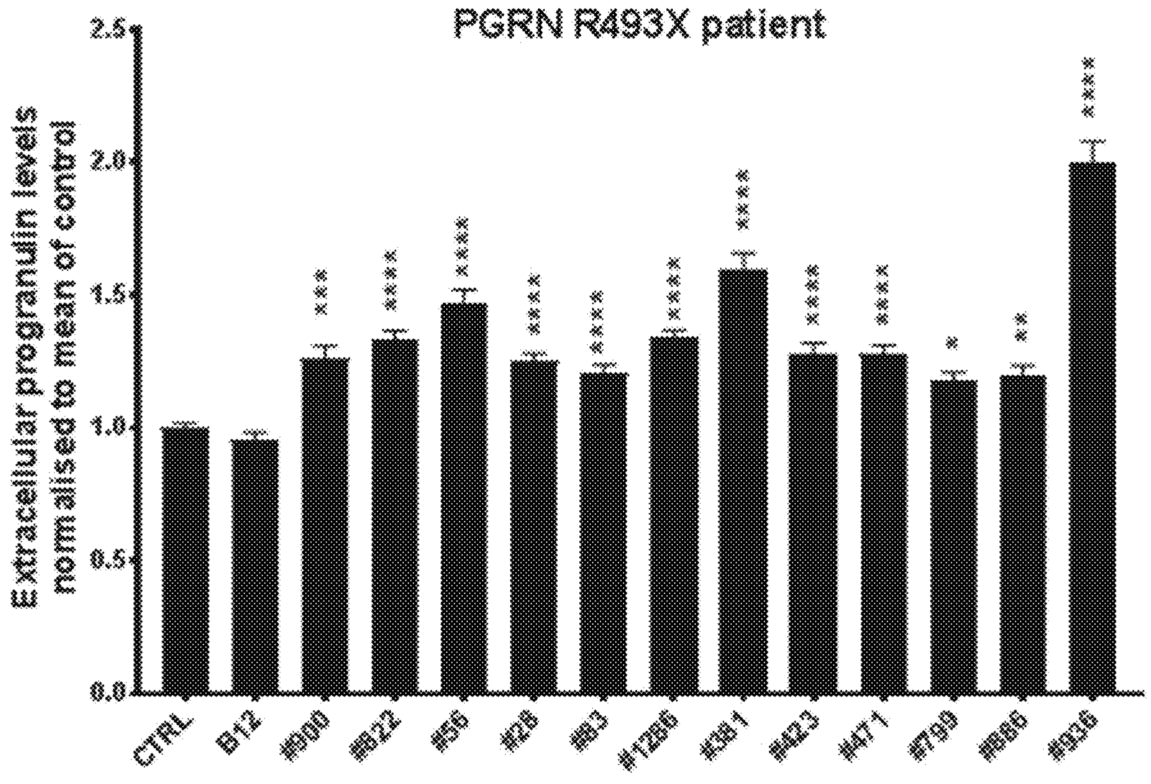
Figure 8A:
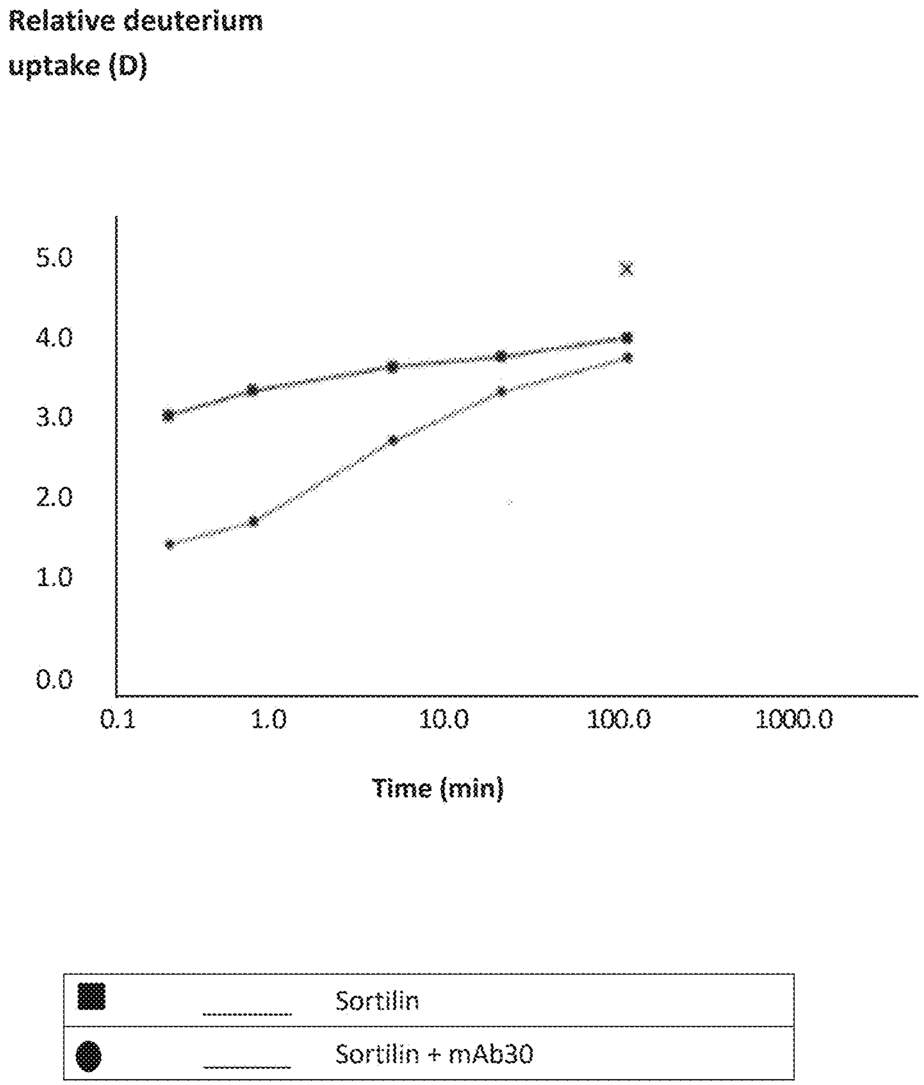
Figure 8B:
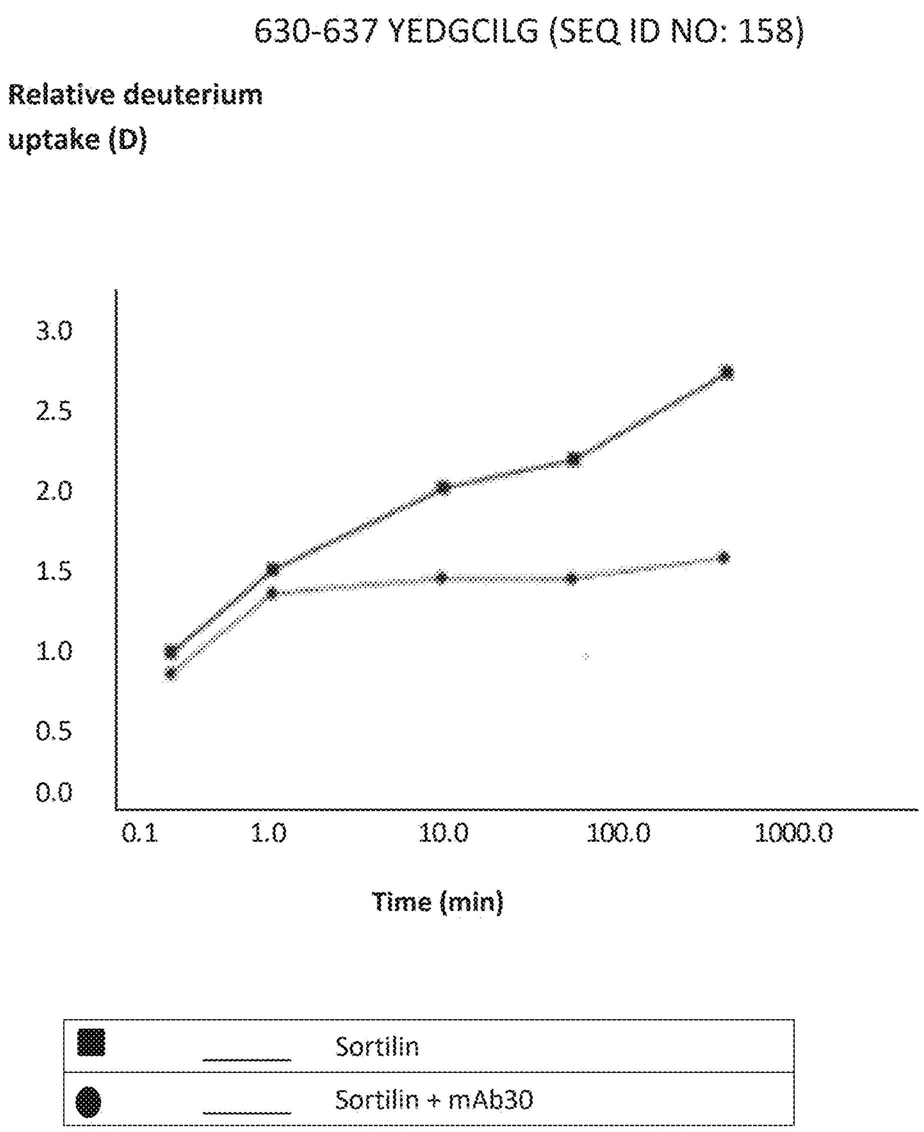
Figure 8C:
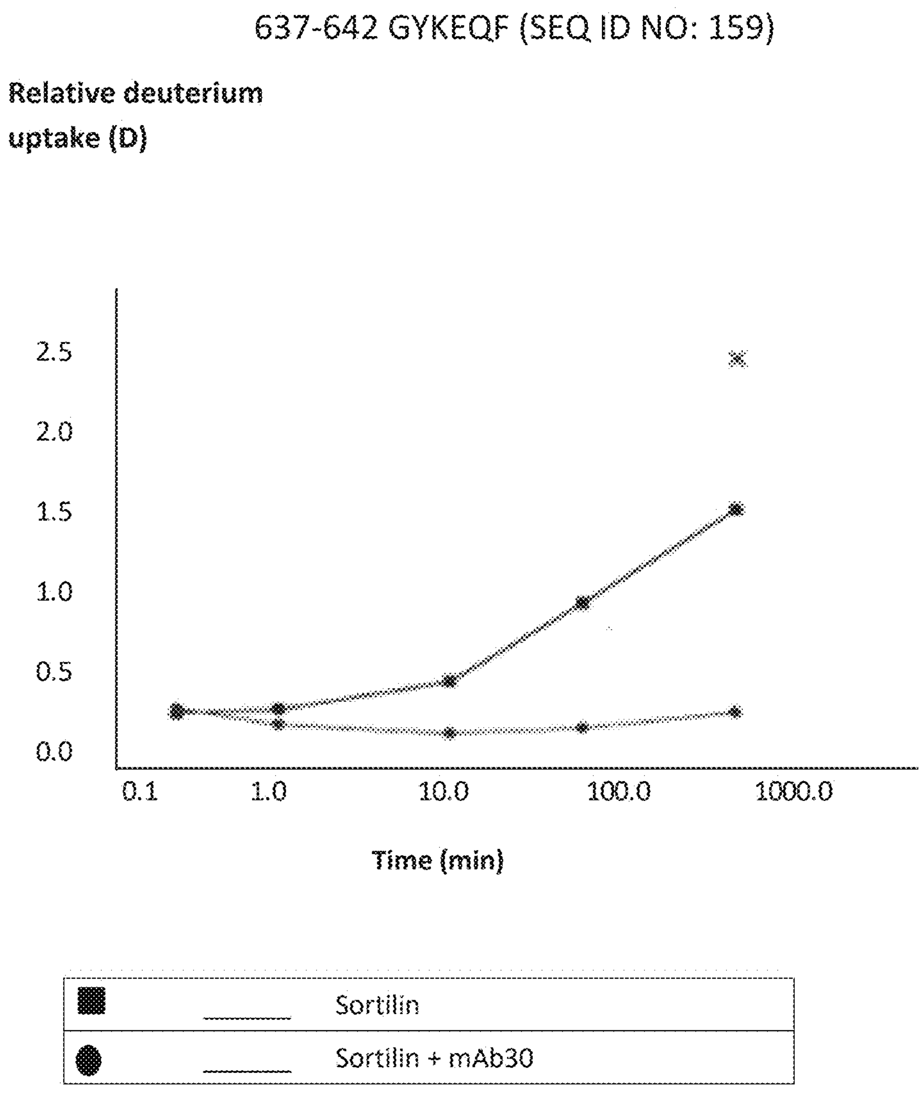
Figure 8D:
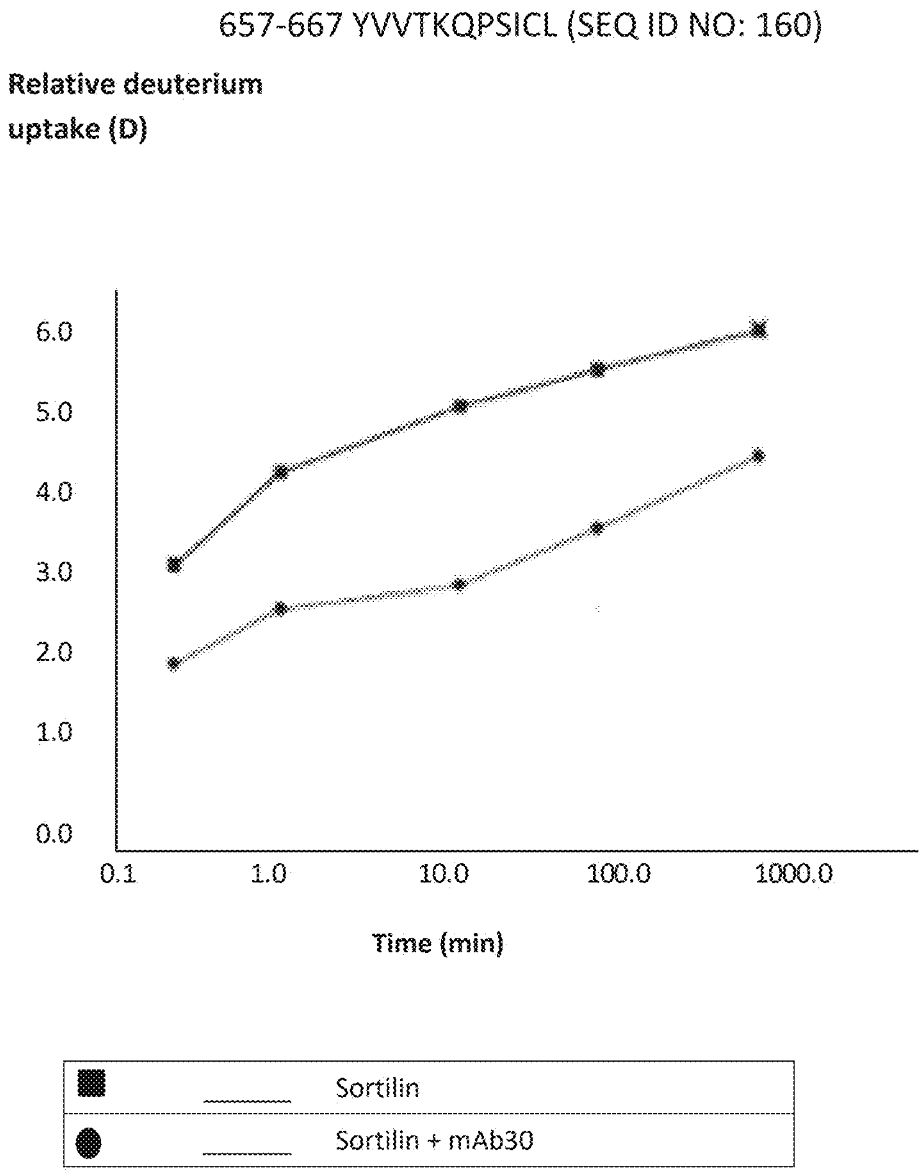
Figure 8E:
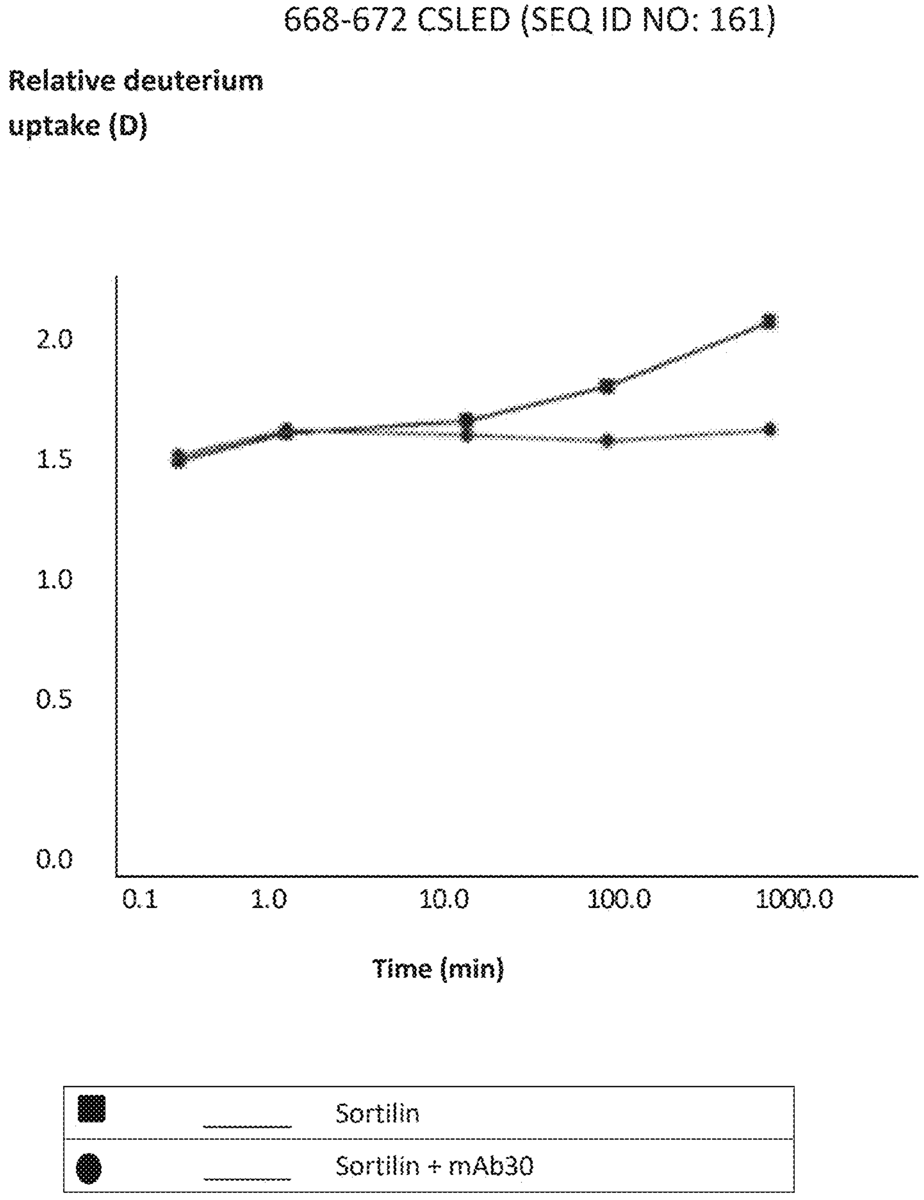
Figure 8F:
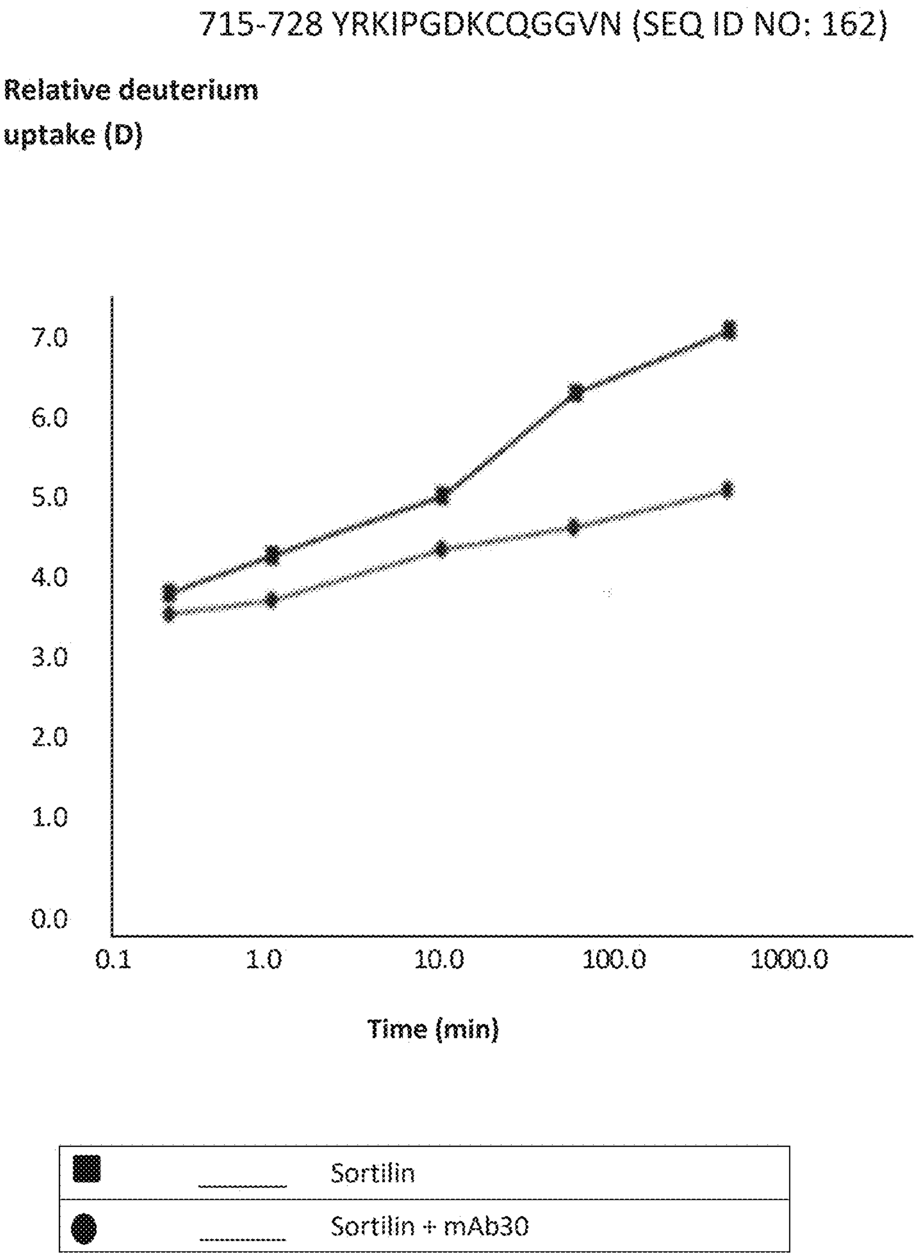

FIGS. 7A and B show the effects of Sortilin antibodies on extracellular PGRN in neuronal differentiated induced pluripotent stem cells (iPSCs) generated from an apparently heathy individual as well as from a PGRN R493X patient.

The anti-sortilin human antibodies #72, #1277, #83, #900, #799, #886, #28, #471, #1286, #822, #423, #56, #381, #936 increased extracellular PGRN levels whereas the control antibody B12 did not. The assay was performed with growth factor matured iPSC neurons plated into 96 wells plate. Antibodies were added to the cell media. The culture media from the iPSC neurons was collected after 72 hrs exposure and analysed by human PGRN ELISA (Biovendor) according to the manufacturer's instructions. Media with antibodies not exposed to the cells showed no signal in the PGRN ELISA. CellTiter-Glo Luminescent cell viability assay (Promega) showed no effect on viability (quantification of intracellular ATP levels) of antibody applications. Data is presented as mean±SEM of three experimental runs with six replicates in each run. Data was analyzed by one-way ANOVA followed by Dunnett's analysis *p<0.05, p<0.01, *p<0.001, ****p<0.0001.

The iPSC lines were reprogramming according to non-integrative methods from human fibroblasts sampled from an apparently heathy individual (18 y male) as well as from PGRN R493X patient (65 y male). The clones used are named BIONi010-A (apparently heathy individual) and LUBi001-A (PGRN R493X patient). They are deposited in the European Bank of induced Pluripotent Stem Cells and distributed by European Collection of Authenticated Cell Cultures. The iPSCs were cultured in monolayer on matrigel (BD Biosciences) in mTeSR1 media (Stemcell Technologies) and Essential 8 madia (Gibco), respectively. Neuronal differentiation was initiated day 0 by dual SMAD inhibition (100 nM LDN and 10 μM SB431542) in N3 media (50% DMEM/F12+50% Neurobasal media supplemented with 0.5% N2, 1% B27 with RA, 0.5 mM GlutaMAX-I, 0.5% NEA, 50 μM 2-mercaptoethanol and 2.5 μg/mL insulin) of iPSCs plated at high density. The cells were split at day 12 and from now on plated on poly-L-ornithine/laminin. LDN and SB431542 were replaced by 20 ng/ml of FGF2 from day 13. From this time point, the cells were split approximately every 5 day until the neuronal progenitor cells (NPCs) were frozen day 21 to generate a NPC bank. These NPCs were thawed, allowed to proliferate before replating day 25 and subjecting to maturation medium (N3 with 20 ng/mL BDNF, 10 ng/ml GDNF, 500 μM db-CAMP, 200 μM ascorbic acid) from day 26. Day 32, the cells were final re-plated into assay plates in maturation medium. FACS studies on BIONi010-A iPSC neurons confirmed surface expression of the sortilin receptor. Antibodies were applied day 57 and samples collected after 72 hours, i.e. day 60.

Example 12: Epitope Mapping of Antibodies Targeting the Progranulin-Sortilin Interaction by Hydrogen/Deuterium Exchange Followed by Mass Spectrometry In hydrogen/deuterium exchange followed by mass spectrometry (HDX-MS) the exchange rate of backbone amide hydrogens in a protein is measured. Hereby, it is possible to probe the conformational dynamics of the entire protein backbone except at proline residues. The rate of the exchange reaction is determined by the hydrogen bonding status of the backbone amide and to a lesser extent its solvent accessibility.

Subtle changes in these two parameters e.g. caused by the presence of a ligand can be observed as a change in deuterium incorporation.

To sub-localize the changes in deuterium incorporation the protein is treated with an acid stable protease (e.g. pepsin), which generates local regions of typically ten to fifteen amino acids. Regions that shows a perturbation in the presence of a ligand is either directly involved in the binding interface or allosterically affected by the binding event.

Epitope Mapping of Antibodies

The deuterium incorporation of the extra cellular region of Sortilin (SEQ ID NO:156) was measured in the—absence and presence of mAb30 which binds the E region. To secure that the measurements were conducted at steady-state conditions the complexes were equilibrated for 15 min at 25° C. before the exchange reaction was initiated. The exchange reaction was initiated by dilution of the protein samples 1:9 (v/v) into deuterated buffer (99% D2O, 20 mM tris, 150 mM NaCl, pDread=7.6). After various time points (15s, 1 min, 10 min, 1 h and 8 h) the exchange reaction was quenched by 1:1 (v/v) dilution with ice-cold quench buffer (2 M glycine, 0.8 M tris-(2-carboxyethyl)phosphine (TCEP), pH=2.3), thereby decreasing the pH to 2.46. The quenched samples were immediately placed inside a −80° freezer and stored until analysis. Fully deuterated control samples were prepared by diluting sortilin samples 1:9 (v/v) into a deuterated denaturation buffer (6 M guanidinium chloride, 99% D2O, 20 mM tris, 150 mM NaCl, pDread=7.6) followed by incubation at 25° C. for 16 h before they were quenched and handled as described above.

The quenched samples were thawed and injected into a cooled (0° C.) reverse-phase UPLC-HDX-system (Waters Inc., USA) equipped with a home-packed pepsin column (internal volume of 60 μL, pepsin beads acquired from Thermo Scientific Inc.). Here, the deuterated protein samples were subjected to online pepsin digestion at 20° C., and the resulting peptic peptides were separated by reverse-phase UPLC.

The peptides were ionized by electrospray ionization into a mass spectrometer (Synapt G2 mass spectrometer, Waters Inc, UK), where the peptides were further separated by ion mobility before final mass determination.

The Identification of peptides was performed on fully reduced and non-deuterated samples by tandem mass spectrometry using a combination of data independent (MSe) and data dependent acquisition.

Data Analysis

Identification of Peptides

The acquired mass spectra were lock mass corrected against GFP and analyzed in PLGS 3.0, which matched precursor and fragment ions to a local protein database. All peptide identifications were carefully assessed manually.

Determination of deuterium incorporation: The acquired mass spectra were lock mass corrected against GFP and the software DynamX 3.0 (Waters Inc., USA) was used to determine the deuterium incorporation for all peptides of sortilin either in absence or presence of antibodies.

A peptide was considered to be a part of the binding epitope if a protection from exchange larger than 0.5D was observed in presence of an antibody.

TABLE 1

Table of identified conformational epitopes by HDX-MS.

| Antibody | Epitope mapping by HDX-MS relative to SEQ ID NO: 145 | | |
|---|---|---|---|
| 30 | 617-642 | 657-672 | 715-728 |

The invention claimed is:

1. An anti-sortilin antibody, or antigen-binding fragment thereof, comprising:

(A)i. a heavy chain variable domain CDR1 comprising SEQ ID NO: 19;

ii. a heavy chain variable domain CDR2 comprising SEQ ID NO: 20;

iii. a heavy chain variable domain CDR3 comprising SEQ ID NO: 21;

iv. a light chain variable domain CDR1 comprising SEQ ID NO: 22;

v. a light chain variable domain CDR2 comprising SEQ ID NO: 23; and vi. a light chain variable domain CDR3 comprising SEQ ID NO: 24, or (B) a heavy chain variable domain comprising SEQ ID NO: 115; and a light chain variable domain comprising SEQ ID NO: 116.

2. A pharmaceutical composition comprising the antibody, or antigen-binding fragment thereof, as defined in claim 1, and a pharmaceutically-acceptable carrier.

3. A kit comprising the antibody, or antigen-binding fragment thereof, as defined in claim 1.

4. An antibody, or antigen-binding fragment thereof, as defined in claim 1 which has been produced or manufactured in a cell line, wherein the cell line is a human cell line, a mammalian non-human cell line, an insect cell line, a yeast cell line or a bacterial cell line.

5. The anti-sortilin antibody of claim 1, wherein the anti-sortilin antibody comprises a heavy chain constant domain and a light chain constant domain.

6. The anti-sortilin antibody of claim 5, wherein the heavy chain constant domain is an IgG1 constant domain.

7. The anti-sortilin antibody of claim 5, wherein the light chain constant domain is a kappa constant domain.

8. The anti-sortilin antibody of claim 1, wherein the anti-sortilin antibody is a full-length anti-sortilin antibody.

9. The anti-sortilin antibody of claim 8, wherein the full-length anti-sortilin antibody is an IgG antibody.

10. The anti-sortilin antibody of claim 8, wherein the full-length anti-sortilin antibody is an IgG1 antibody.

11. The anti-sortilin antibody of claim 8, wherein the full-length anti-sortilin antibody is an IgG1 kappa antibody.

12. A method of administering to a subject the anti-sortilin antibody, or antigen-binding fragment thereof, of claim 4.

* * * * *

SEQUENCE LISTING

```
<160> NUMBER OF SEQ ID NOS: 162

<210> SEQ ID NO 1
<211> LENGTH: 4
<212> TYPE: PRT
<213> ORGANISM: Artificial Sequence
<220> FEATURE:
<223> OTHER INFORMATION: 6003-028 HC CDR 1

<400> SEQUENCE: 1

Tyr Ala Met Ser
1


<210> SEQ ID NO 2
<211> LENGTH: 16
<212> TYPE: PRT
<213> ORGANISM: Artificial
<220> FEATURE:
<223> OTHER INFORMATION: 6003-028 HC CDR2

<400> SEQUENCE: 2

Thr Ile Ser Gly Arg Gly Gly Ser Thr Tyr Tyr Ala Asp Ser Val Lys
1               5                   10                  15


<210> SEQ ID NO 3
<211> LENGTH: 11
<212> TYPE: PRT
<213> ORGANISM: Artificial
<220> FEATURE:
<223> OTHER INFORMATION: 6003-028 HC CDR3

<400> SEQUENCE: 3

Asn Leu Tyr Ser Asn Tyr Trp Tyr Phe Asp Leu
1               5                   10


<210> SEQ ID NO 4
<211> LENGTH: 11
<212> TYPE: PRT
<213> ORGANISM: Artificial
<220> FEATURE:
<223> OTHER INFORMATION: 6003-028 LC CDR1

<400> SEQUENCE: 4

Arg Ala Ser Gln Ser Val Ser Ser Phe Leu Ala
1               5                   10


<210> SEQ ID NO 5
<211> LENGTH: 7
<212> TYPE: PRT
<213> ORGANISM: Artificial
<220> FEATURE:
<223> OTHER INFORMATION: 6003-028 LC CDR2

<400> SEQUENCE: 5

Asp Ala Ser Asn Arg Ala Thr
1               5


<210> SEQ ID NO 6
<211> LENGTH: 9
<212> TYPE: PRT
<213> ORGANISM: Artificial
<220> FEATURE:
<223> OTHER INFORMATION: 6003-028 LC CDR3

<400> SEQUENCE: 6

Gln Gln Arg Ser Asn Trp Pro Leu Thr
1               5
```

<210> SEQ ID NO 7
<211> LENGTH: 5
<212> TYPE: PRT
<213> ORGANISM: Artificial
<220> FEATURE:
<223> OTHER INFORMATION: 6003-056 HC CDR1

<400> SEQUENCE: 7

Ser Tyr Ala Met His
1               5

<210> SEQ ID NO 8
<211> LENGTH: 17
<212> TYPE: PRT
<213> ORGANISM: Artificial
<220> FEATURE:
<223> OTHER INFORMATION: 6003-056 HC CDR2

<400> SEQUENCE: 8

Ala Ile Ser Gly Arg Gly Gly Ser Thr Tyr Tyr Ala Asp Ser Val Lys
1               5                   10                  15

Gly

<210> SEQ ID NO 9
<211> LENGTH: 10
<212> TYPE: PRT
<213> ORGANISM: Artificial
<220> FEATURE:
<223> OTHER INFORMATION: 6003-056 HC CDR3

<400> SEQUENCE: 9

Ile Ile Pro Ser Leu Tyr Trp Tyr Phe Asp
1               5                   10

<210> SEQ ID NO 10
<211> LENGTH: 11
<212> TYPE: PRT
<213> ORGANISM: Artificial
<220> FEATURE:
<223> OTHER INFORMATION: 6003-056 LC CDR1

<400> SEQUENCE: 10

Arg Ala Ser Gln Ser Val Ser Ser Phe Leu Ala
1               5                   10

<210> SEQ ID NO 11
<211> LENGTH: 7
<212> TYPE: PRT
<213> ORGANISM: Artificial
<220> FEATURE:
<223> OTHER INFORMATION: 6003-056 LC CDR2

<400> SEQUENCE: 11

Asp Ala Ser Asn Arg Ala Thr
1               5

<210> SEQ ID NO 12
<211> LENGTH: 9
<212> TYPE: PRT
<213> ORGANISM: Artificial
<220> FEATURE:
<223> OTHER INFORMATION: 6003-056 LC CDR3

<400> SEQUENCE: 12

Gln Gln Arg Ser Asn Trp Pro Leu Thr 1 5

<210> SEQ ID NO 13
<211> LENGTH: 5
<212> TYPE: PRT
<213> ORGANISM: Artificial
<220> FEATURE:
<223> OTHER INFORMATION: 6003-1286 HC CDR1

<400> SEQUENCE: 13

Ser Tyr Ala Met Ser
1 5

<210> SEQ ID NO 14
<211> LENGTH: 17
<212> TYPE: PRT
<213> ORGANISM: Artificial
<220> FEATURE:
<223> OTHER INFORMATION: 6003-1286 HC CDR2

<400> SEQUENCE: 14

Thr Ile Ser Gly Arg Gly Gly Asn Thr Tyr Tyr Ala Asp Ser Val Lys
1 5 10 15

Gly

<210> SEQ ID NO 15
<211> LENGTH: 10
<212> TYPE: PRT
<213> ORGANISM: Artificial
<220> FEATURE:
<223> OTHER INFORMATION: 6003-1286 HC CDR3

<400> SEQUENCE: 15

Asn Ile Tyr Ser His Tyr Trp Tyr Phe Asp
1 5 10

<210> SEQ ID NO 16
<211> LENGTH: 11
<212> TYPE: PRT
<213> ORGANISM: Artificial
<220> FEATURE:
<223> OTHER INFORMATION: 6003-1286 LC CDR1

<400> SEQUENCE: 16

Arg Ala Ser Gln Ser Val Asn Ser Tyr Leu Ala
1 5 10

<210> SEQ ID NO 17
<211> LENGTH: 7
<212> TYPE: PRT
<213> ORGANISM: Artificial
<220> FEATURE:
<223> OTHER INFORMATION: 6003-1286 LC CDR2

<400> SEQUENCE: 17

Asp Ala Ser Asn Arg Ala Thr
1 5

<210> SEQ ID NO 18
<211> LENGTH: 10
<212> TYPE: PRT
<213> ORGANISM: Artificial
<220> FEATURE:
<223> OTHER INFORMATION: 6003-1286 LC CDR3

<400> SEQUENCE: 18

Gln Gln Arg Ser Asn Trp Pro Leu Thr Phe
1 5 10

<210> SEQ ID NO 19
<211> LENGTH: 5
<212> TYPE: PRT
<213> ORGANISM: Artificial
<220> FEATURE:
<223> OTHER INFORMATION: 6003-030 HC CDR1

<400> SEQUENCE: 19

Ser Tyr Ala Met Ser
1 5

<210> SEQ ID NO 20
<211> LENGTH: 17
<212> TYPE: PRT
<213> ORGANISM: Artificial
<220> FEATURE:
<223> OTHER INFORMATION: 6003-030 HC CDR2

<400> SEQUENCE: 20

Thr Ile Ser Gly Arg Gly Gly Asn Thr Tyr Tyr Ala Asp Ser Val Lys
1 5 10 15

Gly

<210> SEQ ID NO 21
<211> LENGTH: 11
<212> TYPE: PRT
<213> ORGANISM: Artificial
<220> FEATURE:
<223> OTHER INFORMATION: 6003-030 HC CDR3

<400> SEQUENCE: 21

Ile Ile Pro Ser Leu Tyr Trp Tyr Phe Asp Leu
1 5 10

<210> SEQ ID NO 22
<211> LENGTH: 11
<212> TYPE: PRT
<213> ORGANISM: Artificial
<220> FEATURE:
<223> OTHER INFORMATION: 6003-030 LC CDR1

<400> SEQUENCE: 22

Arg Ala Ser Gln Ser Val Ser Ser Tyr Leu Ala
1 5 10

<210> SEQ ID NO 23
<211> LENGTH: 7
<212> TYPE: PRT
<213> ORGANISM: Artificial
<220> FEATURE:
<223> OTHER INFORMATION: 6003-030 LC CDR2

<400> SEQUENCE: 23

Asp Ala Ser Asn Arg Ala Thr
1 5

<210> SEQ ID NO 24
<211> LENGTH: 9
<212> TYPE: PRT
<213> ORGANISM: Artificial
<220> FEATURE:
<223> OTHER INFORMATION: 6003-030 LC CDR3

<400> SEQUENCE: 24

Gln Gln Arg Ser Asn Trp Pro Leu Thr
1 5

<210> SEQ ID NO 25
<211> LENGTH: 5
<212> TYPE: PRT
<213> ORGANISM: Artificial
<220> FEATURE:
<223> OTHER INFORMATION: 6003-1277 HC CDR1

<400> SEQUENCE: 25

His Tyr Gly Ile Ser
1 5

<210> SEQ ID NO 26
<211> LENGTH: 17
<212> TYPE: PRT
<213> ORGANISM: Artificial
<220> FEATURE:
<223> OTHER INFORMATION: 6003-1277 HC CDR2

<400> SEQUENCE: 26

Trp Ile Asn Thr Tyr Asn Gly Asn Thr Lys Tyr Ala Gln Lys Leu Gln
1 5 10 15

Gly

<210> SEQ ID NO 27
<211> LENGTH: 7
<212> TYPE: PRT
<213> ORGANISM: Artificial
<220> FEATURE:
<223> OTHER INFORMATION: 6003-1277 HC CDR3

<400> SEQUENCE: 27

Leu Gly Arg Asn Phe Asp Tyr
1 5

<210> SEQ ID NO 28
<211> LENGTH: 11
<212> TYPE: PRT
<213> ORGANISM: Artificial
<220> FEATURE:
<223> OTHER INFORMATION: 6003-1277 LC CDR1

<400> SEQUENCE: 28

Arg Ala Ser Gln Ser Val Ser Ser Tyr Leu Ala
1 5 10

<210> SEQ ID NO 29
<211> LENGTH: 7
<212> TYPE: PRT
<213> ORGANISM: Artificial
<220> FEATURE:
<223> OTHER INFORMATION: 6003-1277 LC CDR2

<400> SEQUENCE: 29

Asp Ala Ser Asn Arg Ala Thr
1 5

<210> SEQ ID NO 30
<211> LENGTH: 10
<212> TYPE: PRT
<213> ORGANISM: Artificial
<220> FEATURE:
<223> OTHER INFORMATION: 6003-1277 LC CDR3

<400> SEQUENCE: 30

Gln Gln Arg Ser Asn Trp Pro Ala Leu Thr
1 5 10

<210> SEQ ID NO 31
<211> LENGTH: 5
<212> TYPE: PRT
<213> ORGANISM: Artificial
<220> FEATURE:
<223> OTHER INFORMATION: 6003-381 HC CDR1

<400> SEQUENCE: 31

Asn Tyr Val Met His
1 5

<210> SEQ ID NO 32
<211> LENGTH: 17
<212> TYPE: PRT
<213> ORGANISM: Artificial
<220> FEATURE:
<223> OTHER INFORMATION: 6003-381 HC CDR2

<400> SEQUENCE: 32

Ala Ile Ser Tyr Asn Gly Asn Asn Lys Tyr Tyr Ala Asp Ser Val Lys
1 5 10 15

Gly

<210> SEQ ID NO 33
<211> LENGTH: 8
<212> TYPE: PRT
<213> ORGANISM: Artificial
<220> FEATURE:
<223> OTHER INFORMATION: 6003-381 HC CDR3

<400> SEQUENCE: 33

Gly Leu Asn Asp Ala Phe Asp Ile
1 5

<210> SEQ ID NO 34
<211> LENGTH: 10
<212> TYPE: PRT
<213> ORGANISM: Artificial
<220> FEATURE:
<223> OTHER INFORMATION: 6003-381 LC CDR1

<400> SEQUENCE: 34

Ala Ser Gln Ser Val Ser Gly Tyr Leu Ala
1 5 10

<210> SEQ ID NO 35
<211> LENGTH: 7
<212> TYPE: PRT
<213> ORGANISM: Artificial
<220> FEATURE:
<223> OTHER INFORMATION: 6003-381 LC CDR2

<400> SEQUENCE: 35

Asn Ala Ser Asn Arg Ala Thr
1 5

<210> SEQ ID NO 36
<211> LENGTH: 10
<212> TYPE: PRT
<213> ORGANISM: Artificial
<220> FEATURE:
<223> OTHER INFORMATION: 6003-381 LC CDR3

<400> SEQUENCE: 36

Gln Gln Arg Ser Asn Trp Pro Pro Leu Thr
1 5 10

<210> SEQ ID NO 37
<211> LENGTH: 5
<212> TYPE: PRT
<213> ORGANISM: Artificial
<220> FEATURE:
<223> OTHER INFORMATION: 6003-83 HC CDR1

<400> SEQUENCE: 37

Ser Tyr Ala Met Ser
1 5

<210> SEQ ID NO 38
<211> LENGTH: 17
<212> TYPE: PRT
<213> ORGANISM: Artificial
<220> FEATURE:
<223> OTHER INFORMATION: 6003-83 HC CDR2

<400> SEQUENCE: 38

Thr Ile Ser Gly Arg Gly Gly Ser Thr Tyr Tyr Ala Asp Ser Val Lys
1 5 10 15

Gly

<210> SEQ ID NO 39
<211> LENGTH: 10
<212> TYPE: PRT
<213> ORGANISM: Artificial
<220> FEATURE:
<223> OTHER INFORMATION: 6003-83 HC CDR3

<400> SEQUENCE: 39

Ile Val Ala Thr Met Tyr Trp Tyr Phe Asp
1 5 10

<210> SEQ ID NO 40
<211> LENGTH: 11
<212> TYPE: PRT
<213> ORGANISM: Artificial
<220> FEATURE:
<223> OTHER INFORMATION: 6003-83 LC CDR1

<400> SEQUENCE: 40

Arg Ala Ser Gln Ser Val Ser Ser Tyr Leu Ala
1 5 10

<210> SEQ ID NO 41
<211> LENGTH: 7
<212> TYPE: PRT
<213> ORGANISM: Artificial
<220> FEATURE:
<223> OTHER INFORMATION: 6003-83 LC CDR2

<400> SEQUENCE: 41

Asp Ala Ser Asn Arg Ala Thr
1 5

<210> SEQ ID NO 42
<211> LENGTH: 9
<212> TYPE: PRT
<213> ORGANISM: Artificial
<220> FEATURE:

<223> OTHER INFORMATION: 6003-83 LC CDR3

<400> SEQUENCE: 42

Gln Gln Arg Ser Asn Trp Pro Ile Thr
1 5

<210> SEQ ID NO 43
<211> LENGTH: 5
<212> TYPE: PRT
<213> ORGANISM: Artificial
<220> FEATURE:
<223> OTHER INFORMATION: 6003-799 HC CDR1

<400> SEQUENCE: 43

Ser Tyr Gly Met His
1 5

<210> SEQ ID NO 44
<211> LENGTH: 17
<212> TYPE: PRT
<213> ORGANISM: Artificial
<220> FEATURE:
<223> OTHER INFORMATION: 6003-799 HC CDR2

<400> SEQUENCE: 44

Val Ile Ser Tyr Asp Gly Ser Asn Lys Tyr Tyr Ala Asp Ser Val Lys
1 5 10 15

Gly

<210> SEQ ID NO 45
<211> LENGTH: 8
<212> TYPE: PRT
<213> ORGANISM: Artificial
<220> FEATURE:
<223> OTHER INFORMATION: 6003-799 HC CDR3

<400> SEQUENCE: 45

Leu Thr Gly Asp Ala Phe Asp Ile
1 5

<210> SEQ ID NO 46
<211> LENGTH: 11
<212> TYPE: PRT
<213> ORGANISM: Artificial
<220> FEATURE:
<223> OTHER INFORMATION: 6003-799 LC CDR1

<400> SEQUENCE: 46

Arg Ala Ser Gln Ser Val Ser Ser Tyr Leu Val
1 5 10

<210> SEQ ID NO 47
<211> LENGTH: 7
<212> TYPE: PRT
<213> ORGANISM: Artificial
<220> FEATURE:
<223> OTHER INFORMATION: 6003-799 LC CDR2

<400> SEQUENCE: 47

His Ala Ser Asn Arg Ala Thr
1 5

<210> SEQ ID NO 48
<211> LENGTH: 10
<212> TYPE: PRT
<213> ORGANISM: Artificial

<220> FEATURE:
<223> OTHER INFORMATION: 6003-799 LC CDR3

<400> SEQUENCE: 48

Gln Gln Arg Ser Asn Trp Pro Arg Ile Thr
1 5 10

<210> SEQ ID NO 49
<211> LENGTH: 5
<212> TYPE: PRT
<213> ORGANISM: Artificial
<220> FEATURE:
<223> OTHER INFORMATION: 6003-910 HC CDR1

<400> SEQUENCE: 49

Ser Tyr Ala Met Ser
1 5

<210> SEQ ID NO 50
<211> LENGTH: 17
<212> TYPE: PRT
<213> ORGANISM: Artificial
<220> FEATURE:
<223> OTHER INFORMATION: 6003-910 HC CDR2

<400> SEQUENCE: 50

Ala Ile Ser Gly Ser Gly Gly Ser Thr Tyr Tyr Val Asp Ser Val Lys
1 5 10 15

Gly

<210> SEQ ID NO 51
<211> LENGTH: 14
<212> TYPE: PRT
<213> ORGANISM: Artificial
<220> FEATURE:
<223> OTHER INFORMATION: 6003-910 HC CDR3

<400> SEQUENCE: 51

Asp Ile Arg Gly Ile Gly Phe Gly Tyr Tyr Tyr Gly Met Asp
1 5 10

<210> SEQ ID NO 52
<211> LENGTH: 11
<212> TYPE: PRT
<213> ORGANISM: Artificial
<220> FEATURE:
<223> OTHER INFORMATION: 6003-910 LC CDR1

<400> SEQUENCE: 52

Arg Ala Ser Gln Ser Val Ser Ser Tyr Leu Val
1 5 10

<210> SEQ ID NO 53
<211> LENGTH: 7
<212> TYPE: PRT
<213> ORGANISM: Artificial
<220> FEATURE:
<223> OTHER INFORMATION: 6003-910 LC CDR2

<400> SEQUENCE: 53

Asp Ala Ser Asn Arg Ala Thr
1 5

<210> SEQ ID NO 54
<211> LENGTH: 9
<212> TYPE: PRT

<213> ORGANISM: Artificial
<220> FEATURE:
<223> OTHER INFORMATION: 6003-910 LC CDR3

<400> SEQUENCE: 54

Gln Gln Arg Ser Asn Trp Pro Pro Thr
1 5

<210> SEQ ID NO 55
<211> LENGTH: 5
<212> TYPE: PRT
<213> ORGANISM: Artificial
<220> FEATURE:
<223> OTHER INFORMATION: 6002-423 HC CDR1

<400> SEQUENCE: 55

Ser Tyr Val Met Ser
1 5

<210> SEQ ID NO 56
<211> LENGTH: 17
<212> TYPE: PRT
<213> ORGANISM: Artificial
<220> FEATURE:
<223> OTHER INFORMATION: 6003-423 HC CDR2

<400> SEQUENCE: 56

Thr Ile Ser Gly Gly Gly Gly Asn Thr Asn Tyr Thr Asp Ser Val Lys
1 5 10 15

Gly

<210> SEQ ID NO 57
<211> LENGTH: 8
<212> TYPE: PRT
<213> ORGANISM: Artificial
<220> FEATURE:
<223> OTHER INFORMATION: 6003-423 HC CDR3

<400> SEQUENCE: 57

Asn Trp Gly Ser Gly Phe Asp Tyr
1 5

<210> SEQ ID NO 58
<211> LENGTH: 11
<212> TYPE: PRT
<213> ORGANISM: Artificial
<220> FEATURE:
<223> OTHER INFORMATION: 6003-423 LC CDR1

<400> SEQUENCE: 58

Arg Ala Ser Gln Ser Val Ser Ser Tyr Leu Ala
1 5 10

<210> SEQ ID NO 59
<211> LENGTH: 7
<212> TYPE: PRT
<213> ORGANISM: Artificial
<220> FEATURE:
<223> OTHER INFORMATION: 6003-423 LC CDR2

<400> SEQUENCE: 59

Asp Ala Ser Asn Arg Ala Thr
1 5

<210> SEQ ID NO 60
<211> LENGTH: 10

<212> TYPE: PRT
<213> ORGANISM: Artificial
<220> FEATURE:
<223> OTHER INFORMATION: 6003-423 LC CDR3

<400> SEQUENCE: 60

Gln Gln Arg Ser Asn Trp Leu Ile Phe Thr
1 5 10

<210> SEQ ID NO 61
<211> LENGTH: 5
<212> TYPE: PRT
<213> ORGANISM: Artificial
<220> FEATURE:
<223> OTHER INFORMATION: 6003-822 HC CDR1

<400> SEQUENCE: 61

Ser Tyr Ala Met Ser
1 5

<210> SEQ ID NO 62
<211> LENGTH: 17
<212> TYPE: PRT
<213> ORGANISM: Artificial
<220> FEATURE:
<223> OTHER INFORMATION: 6003-822 HC CDR2

<400> SEQUENCE: 62

Ser Ile Ser Gly Arg Leu Gly Thr Thr Tyr Tyr Ala Ala Ser Val Lys
1 5 10 15

Gly

<210> SEQ ID NO 63
<211> LENGTH: 9
<212> TYPE: PRT
<213> ORGANISM: Artificial
<220> FEATURE:
<223> OTHER INFORMATION: 6003-822 HC CDR3

<400> SEQUENCE: 63

Lys Ala Pro Ser Asp Ala Phe Asp Ile
1 5

<210> SEQ ID NO 64
<211> LENGTH: 11
<212> TYPE: PRT
<213> ORGANISM: Artificial
<220> FEATURE:
<223> OTHER INFORMATION: 6003-822 LC CDR1

<400> SEQUENCE: 64

Arg Ala Ser Gln Ser Val Ser Ser Tyr Leu Ala
1 5 10

<210> SEQ ID NO 65
<211> LENGTH: 7
<212> TYPE: PRT
<213> ORGANISM: Artificial
<220> FEATURE:
<223> OTHER INFORMATION: 6003-822 LC CDR2

<400> SEQUENCE: 65

Asp Ala Ser Asn Arg Ala Thr
1 5

<210> SEQ ID NO 66

<211> LENGTH: 10
<212> TYPE: PRT
<213> ORGANISM: Artificial
<220> FEATURE:
<223> OTHER INFORMATION: 6003-822 LC CDR3

<400> SEQUENCE: 66

Gln Gln Arg Ser Asn Trp Pro Ile Phe Thr
1 5 10

<210> SEQ ID NO 67
<211> LENGTH: 5
<212> TYPE: PRT
<213> ORGANISM: Artificial
<220> FEATURE:
<223> OTHER INFORMATION: 6003-886 HC CDR1

<400> SEQUENCE: 67

Lys Tyr Gly Ile Ser
1 5

<210> SEQ ID NO 68
<211> LENGTH: 17
<212> TYPE: PRT
<213> ORGANISM: Artificial
<220> FEATURE:
<223> OTHER INFORMATION: 6003-886 HC CDR2

<400> SEQUENCE: 68

Trp Ile Ser Ala Tyr Asn Gly Asn Thr Asn Tyr Ala Gln Lys Leu Gln
1 5 10 15

Asp

<210> SEQ ID NO 69
<211> LENGTH: 15
<212> TYPE: PRT
<213> ORGANISM: Artificial
<220> FEATURE:
<223> OTHER INFORMATION: 6003-886 HC CDR3

<400> SEQUENCE: 69

Asp Gly Pro Leu Thr Gly Asp Phe Thr Phe Tyr Gly Met Asp Val
1 5 10 15

<210> SEQ ID NO 70
<211> LENGTH: 11
<212> TYPE: PRT
<213> ORGANISM: Artificial
<220> FEATURE:
<223> OTHER INFORMATION: 6003-886 LC CDR1

<400> SEQUENCE: 70

Arg Ala Ser Gln Ser Val Ser Ser Tyr Leu Ala
1 5 10

<210> SEQ ID NO 71
<211> LENGTH: 7
<212> TYPE: PRT
<213> ORGANISM: Artificial
<220> FEATURE:
<223> OTHER INFORMATION: 6003-886 LC CDR2

<400> SEQUENCE: 71

Asp Ala Ser Asn Arg Ala Thr
1 5

<210> SEQ ID NO 72
<211> LENGTH: 10
<212> TYPE: PRT
<213> ORGANISM: Artificial
<220> FEATURE:
<223> OTHER INFORMATION: 6003-886 LC CDR3

<400> SEQUENCE: 72

Gln Gln Arg Ser Asn Trp Pro Pro Phe Thr
1 5 10

<210> SEQ ID NO 73
<211> LENGTH: 5
<212> TYPE: PRT
<213> ORGANISM: Artificial
<220> FEATURE:
<223> OTHER INFORMATION: 6003-72 HC CDR1

<400> SEQUENCE: 73

Ser Tyr Ala Met Asn
1 5

<210> SEQ ID NO 74
<211> LENGTH: 17
<212> TYPE: PRT
<213> ORGANISM: Artificial
<220> FEATURE:
<223> OTHER INFORMATION: 6003-72 HC CDR2

<400> SEQUENCE: 74

Ala Ile Ser Gly Ser Gly Gly Ser Thr Tyr Tyr Ala Asp Ser Val Lys
1 5 10 15

Gly

<210> SEQ ID NO 75
<211> LENGTH: 13
<212> TYPE: PRT
<213> ORGANISM: Artificial
<220> FEATURE:
<223> OTHER INFORMATION: 6003-72 HC CDR3

<400> SEQUENCE: 75

Arg Gly Arg Gly Ile Gly Tyr Tyr Asn Gly Met Asp Val
1 5 10

<210> SEQ ID NO 76
<211> LENGTH: 12
<212> TYPE: PRT
<213> ORGANISM: Artificial
<220> FEATURE:
<223> OTHER INFORMATION: 6003-72 LC CDR1

<400> SEQUENCE: 76

Arg Ala Ser Gln Ser Val Ser Ser Ser Tyr Leu Ala
1 5 10

<210> SEQ ID NO 77
<211> LENGTH: 7
<212> TYPE: PRT
<213> ORGANISM: Artificial
<220> FEATURE:
<223> OTHER INFORMATION: 6003-72 LC CDR2

<400> SEQUENCE: 77

Gly Ala Ser Ser Arg Ala Thr
1 5

<210> SEQ ID NO 78
<211> LENGTH: 10
<212> TYPE: PRT
<213> ORGANISM: Artificial
<220> FEATURE:
<223> OTHER INFORMATION: 6003-72 LC CDR3

<400> SEQUENCE: 78

Gln Gln Tyr Gly Ser Ser Pro Met Tyr Thr
1 5 10

<210> SEQ ID NO 79
<211> LENGTH: 5
<212> TYPE: PRT
<213> ORGANISM: Artificial
<220> FEATURE:
<223> OTHER INFORMATION: 6003-900 HC CDR1

<400> SEQUENCE: 79

Ser Tyr Ser Met Asn
1 5

<210> SEQ ID NO 80
<211> LENGTH: 16
<212> TYPE: PRT
<213> ORGANISM: Artificial
<220> FEATURE:
<223> OTHER INFORMATION: 6003-900 HC CDR2

<400> SEQUENCE: 80

Ile Ser Ser Ser Ser Ser Tyr Ile Tyr Tyr Ala Asp Ser Val Lys Gly
1 5 10 15

<210> SEQ ID NO 81
<211> LENGTH: 11
<212> TYPE: PRT
<213> ORGANISM: Artificial
<220> FEATURE:
<223> OTHER INFORMATION: 6003-900 HC CDR3

<400> SEQUENCE: 81

Arg Gly Ser Gly Ser Tyr Asp Ala Phe Asp Ile
1 5 10

<210> SEQ ID NO 82
<211> LENGTH: 11
<212> TYPE: PRT
<213> ORGANISM: Artificial
<220> FEATURE:
<223> OTHER INFORMATION: 6003-900 LC CDR1

<400> SEQUENCE: 82

Arg Ala Ser Gln Ser Ile Gly Tyr Ser Leu His
1 5 10

<210> SEQ ID NO 83
<211> LENGTH: 7
<212> TYPE: PRT
<213> ORGANISM: Artificial
<220> FEATURE:
<223> OTHER INFORMATION: 6003-900 LC CDR2

<400> SEQUENCE: 83

Tyr Ala Ser Gln Ser Phe Ser
1 5

<210> SEQ ID NO 84
<211> LENGTH: 9
<212> TYPE: PRT
<213> ORGANISM: Artificial
<220> FEATURE:
<223> OTHER INFORMATION: 6003-900 LC CDR3

<400> SEQUENCE: 84

His Gln Ser Ser Ser Leu Pro Leu Thr
1 5

<210> SEQ ID NO 85
<211> LENGTH: 5
<212> TYPE: PRT
<213> ORGANISM: Artificial
<220> FEATURE:
<223> OTHER INFORMATION: 6003-936 HC CDR1

<400> SEQUENCE: 85

Ser Phe Trp Ile Gly
1 5

<210> SEQ ID NO 86
<211> LENGTH: 16
<212> TYPE: PRT
<213> ORGANISM: Artificial
<220> FEATURE:
<223> OTHER INFORMATION: 6003-936 HC CDR2

<400> SEQUENCE: 86

Ile Ile Tyr Pro Gly Asp Ser Asp Thr Arg Tyr Ser Pro Ser Phe Gln
1 5 10 15

<210> SEQ ID NO 87
<211> LENGTH: 13
<212> TYPE: PRT
<213> ORGANISM: Artificial
<220> FEATURE:
<223> OTHER INFORMATION: 6003-936 HC CDR3

<400> SEQUENCE: 87

His Ser Arg Gly Ser Phe Trp Tyr Gly Ala Phe Gln His
1 5 10

<210> SEQ ID NO 88
<211> LENGTH: 11
<212> TYPE: PRT
<213> ORGANISM: Artificial
<220> FEATURE:
<223> OTHER INFORMATION: 6003-936 LC CDR1

<400> SEQUENCE: 88

Arg Ala Ser Gln Ser Ile Gly Ser Ser Leu His
1 5 10

<210> SEQ ID NO 89
<211> LENGTH: 7
<212> TYPE: PRT
<213> ORGANISM: Artificial
<220> FEATURE:
<223> OTHER INFORMATION: 6003-936 LC CDR2

<400> SEQUENCE: 89

Tyr Ala Ser Gln Ser Phe Ser
1 5

<210> SEQ ID NO 90

<211> LENGTH: 9
<212> TYPE: PRT
<213> ORGANISM: Artificial
<220> FEATURE:
<223> OTHER INFORMATION: 6003-936 LC CDR3

<400> SEQUENCE: 90

His Gln Ser Ser Ser Leu Pro His Thr
1               5

<210> SEQ ID NO 91
<211> LENGTH: 5
<212> TYPE: PRT
<213> ORGANISM: Artificial
<220> FEATURE:
<223> OTHER INFORMATION: 6003-408 HC CDR1

<400> SEQUENCE: 91

Ser Tyr Ser Met Asn
1               5

<210> SEQ ID NO 92
<211> LENGTH: 17
<212> TYPE: PRT
<213> ORGANISM: Artificial
<220> FEATURE:
<223> OTHER INFORMATION: 6003-408 HC CDR2

<400> SEQUENCE: 92

Ser Ile Ser Ser Ser Ser Ser Tyr Ile Tyr Tyr Ala Asp Ser Val Lys
1               5                   10                  15

Gly

<210> SEQ ID NO 93
<211> LENGTH: 15
<212> TYPE: PRT
<213> ORGANISM: Artificial
<220> FEATURE:
<223> OTHER INFORMATION: 6003-408 HC CDR3

<400> SEQUENCE: 93

Arg Arg Ile Ala Ala Ala Gly Thr Gly Tyr Gly Ala Phe Asp Ile
1               5                   10                  15

<210> SEQ ID NO 94
<211> LENGTH: 11
<212> TYPE: PRT
<213> ORGANISM: Artificial
<220> FEATURE:
<223> OTHER INFORMATION: 6003-408 LC CDR1

<400> SEQUENCE: 94

Arg Ala Ser Gln Gly Ile Thr Ser Ala Leu Ala
1               5                   10

<210> SEQ ID NO 95
<211> LENGTH: 7
<212> TYPE: PRT
<213> ORGANISM: Artificial
<220> FEATURE:
<223> OTHER INFORMATION: 6003-408 LC CDR2

<400> SEQUENCE: 95

Asp Ala Ser Ser Leu Glu Ser
1               5

<210> SEQ ID NO 96
<211> LENGTH: 10
<212> TYPE: PRT
<213> ORGANISM: Artificial
<220> FEATURE:
<223> OTHER INFORMATION: 6003-408 LC CDR3

<400> SEQUENCE: 96

Gln Gln Phe Asn Gly Tyr Pro Met Phe Ser
1 5 10

<210> SEQ ID NO 97
<211> LENGTH: 5
<212> TYPE: PRT
<213> ORGANISM: Artificial
<220> FEATURE:
<223> OTHER INFORMATION: 6003-471 HC CDR1

<400> SEQUENCE: 97

Asn Tyr Ala Ile Ser
1 5

<210> SEQ ID NO 98
<211> LENGTH: 17
<212> TYPE: PRT
<213> ORGANISM: Artificial
<220> FEATURE:
<223> OTHER INFORMATION: 6003-471 HC CDR2

<400> SEQUENCE: 98

Arg Ile Ile Pro Ile Phe Gly Ile Ala Asn Tyr Ala Gln Lys Phe Gln
1 5 10 15

Gly

<210> SEQ ID NO 99
<211> LENGTH: 13
<212> TYPE: PRT
<213> ORGANISM: Artificial
<220> FEATURE:
<223> OTHER INFORMATION: 6003-471 HC CDR3

<400> SEQUENCE: 99

Asp Arg Arg Gly Phe Ser Gly Tyr Glu Val Phe Asp Tyr
1 5 10

<210> SEQ ID NO 100
<211> LENGTH: 11
<212> TYPE: PRT
<213> ORGANISM: Artificial
<220> FEATURE:
<223> OTHER INFORMATION: 6003-471 LC CDR1

<400> SEQUENCE: 100

Arg Ala Ser Gln Gly Ile Ser Ser Trp Leu Ala
1 5 10

<210> SEQ ID NO 101
<211> LENGTH: 7
<212> TYPE: PRT
<213> ORGANISM: Artificial
<220> FEATURE:
<223> OTHER INFORMATION: 6003-471 LC CDR2

<400> SEQUENCE: 101

Ala Thr Ser Ser Leu Gln Ser
1 5

<210> SEQ ID NO 102
<211> LENGTH: 10
<212> TYPE: PRT
<213> ORGANISM: Artificial
<220> FEATURE:
<223> OTHER INFORMATION: 6003-471 LC CDR3

<400> SEQUENCE: 102

Gln Gln Tyr Asn Ser Tyr Pro Ile Thr Phe
1 5 10

<210> SEQ ID NO 103
<211> LENGTH: 5
<212> TYPE: PRT
<213> ORGANISM: Artificial
<220> FEATURE:
<223> OTHER INFORMATION: 6003-972 HC CDR1

<400> SEQUENCE: 103

Asp Tyr Ala Met His
1 5

<210> SEQ ID NO 104
<211> LENGTH: 17
<212> TYPE: PRT
<213> ORGANISM: Artificial
<220> FEATURE:
<223> OTHER INFORMATION: 6003-972 HC CDR2

<400> SEQUENCE: 104

Val Ile Ser Tyr Asp Gly Ser Asn Lys Tyr Tyr Ala Asp Ser Val Lys
1 5 10 15

Gly

<210> SEQ ID NO 105
<211> LENGTH: 10
<212> TYPE: PRT
<213> ORGANISM: Artificial
<220> FEATURE:
<223> OTHER INFORMATION: 6003-972 HC CDR3

<400> SEQUENCE: 105

Asp Pro Ser Gly Gly Trp Tyr Phe Asp Leu
1 5 10

<210> SEQ ID NO 106
<211> LENGTH: 11
<212> TYPE: PRT
<213> ORGANISM: Artificial
<220> FEATURE:
<223> OTHER INFORMATION: 6003-972 LC CDR1

<400> SEQUENCE: 106

Arg Ala Ser Gln Ser Val Ser Ser Tyr Leu Ala
1 5 10

<210> SEQ ID NO 107
<211> LENGTH: 7
<212> TYPE: PRT
<213> ORGANISM: Artificial
<220> FEATURE:
<223> OTHER INFORMATION: 6003-972 LC CDR2

<400> SEQUENCE: 107

Asp Ala Ser Asn Arg Ala Thr
1 5

<210> SEQ ID NO 108
<211> LENGTH: 9
<212> TYPE: PRT
<213> ORGANISM: Artificial
<220> FEATURE:
<223> OTHER INFORMATION: 6003-972 LC CDR3

<400> SEQUENCE: 108

Gln Gln Arg Ser His Trp Pro Arg Thr
1 5

<210> SEQ ID NO 109
<211> LENGTH: 119
<212> TYPE: PRT
<213> ORGANISM: Artificial
<220> FEATURE:
<223> OTHER INFORMATION: 6003-28 HC

<400> SEQUENCE: 109

Glu Val Gln Leu Leu Glu Ser Gly Gly Gly Leu Val Gln Pro Gly Gly
1 5 10 15

Ser Leu Arg Leu Ser Cys Ala Ala Ser Gly Phe Thr Phe Ser Ser Tyr
20 25 30

Ala Met Ser Trp Val Arg Gln Ala Pro Gly Lys Gly Leu Glu Trp Val
35 40 45

Ser Thr Ile Ser Gly Arg Gly Gly Ser Thr Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Asn Leu Tyr Ser Asn Tyr Trp Tyr Phe Asp Leu Trp Gly Arg Gly
100 105 110

Thr Leu Val Thr Val Ser Ser
115

<210> SEQ ID NO 110
<211> LENGTH: 107
<212> TYPE: PRT
<213> ORGANISM: Artificial
<220> FEATURE:
<223> OTHER INFORMATION: 6003-28 LC

<400> SEQUENCE: 110

Glu Ile Val Leu Thr Gln Ser Pro Ala Thr Leu Ser Leu Ser Pro Gly
1 5 10 15

Glu Arg Ala Thr Leu Ser Cys Arg Ala Ser Gln Ser Val Ser Ser Phe
20 25 30

Leu Ala Trp Tyr Gln Gln Lys Pro Gly Gln Ala Pro Arg Leu Leu Ile
35 40 45

Tyr Asp Ala Ser Asn Arg Ala Thr Gly Ile Pro Ala Arg Phe Ser Gly
50 55 60

Ser Gly Ser Gly Thr Asp Phe Thr Leu Thr Ile Ser Ser Leu Glu Pro
65 70 75 80

Glu Asp Phe Ala Val Tyr Tyr Cys Gln Gln Arg Ser Asn Trp Pro Leu
85 90 95

Thr Phe Gly Gly Gly Thr Lys Val Glu Ile Lys
100 105

<210> SEQ ID NO 111
<211> LENGTH: 119
<212> TYPE: PRT
<213> ORGANISM: Artificial
<220> FEATURE:
<223> OTHER INFORMATION: 6003-56 HC

<400> SEQUENCE: 111

Glu Val Gln Val Leu Glu Ser Gly Gly Gly Leu Val Gln Pro Gly Gly
1 5 10 15

Ser Leu Arg Leu Ser Cys Val Ala Ser Gly Phe Thr Phe Ser Ser Tyr
20 25 30

Ala Met His Trp Val Arg Gln Ala Pro Gly Lys Gly Leu Glu Trp Val
35 40 45

Ser Ala Ile Ser Gly Arg Gly Gly Ser Thr Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Ile Ile Pro Ser Leu Tyr Trp Tyr Phe Asp Leu Trp Gly Arg Gly
100 105 110

Thr Leu Val Thr Val Ser Ser
115

<210> SEQ ID NO 112
<211> LENGTH: 107
<212> TYPE: PRT
<213> ORGANISM: Artificial
<220> FEATURE:
<223> OTHER INFORMATION: 6003-56 LC

<400> SEQUENCE: 112

Glu Ile Val Leu Thr Gln Ser Pro Ala Thr Leu Ser Leu Ser Pro Gly
1 5 10 15

Glu Arg Ala Thr Leu Ser Cys Arg Ala Ser Gln Ser Val Ser Ser Phe
20 25 30

Leu Ala Trp Tyr Gln Gln Lys Pro Gly Gln Ala Pro Arg Leu Leu Ile
35 40 45

Tyr Asp Ala Ser Asn Arg Ala Thr Gly Ile Pro Ala Arg Phe Ser Gly
50 55 60

Ser Gly Ser Gly Thr Asp Phe Thr Leu Thr Ile Ser Ser Leu Glu Pro
65 70 75 80

Glu Asp Phe Ala Val Tyr Tyr Cys Gln Gln Arg Ser Asn Trp Pro Leu
85 90 95

Thr Phe Gly Gly Gly Thr Lys Val Glu Ile Lys
100 105

<210> SEQ ID NO 113
<211> LENGTH: 119
<212> TYPE: PRT
<213> ORGANISM: Artificial
<220> FEATURE:
<223> OTHER INFORMATION: 6003-1286 HC

<400> SEQUENCE: 113

Glu Val Gln Leu Leu Glu Ser Gly Gly Gly Leu Val Gln Pro Gly Gly
1 5 10 15

Ser Leu Arg Leu Ser Cys Ala Ala Ser Gly Phe Thr Phe Ser Ser Tyr

```
            20                  25                  30

Ala Met Ser Trp Val Arg Gln Ala Pro Gly Lys Gly Leu Glu Trp Val
        35                  40                  45

Ser Thr Ile Ser Gly Arg Gly Gly Asn Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Ala Ala Val Tyr Tyr Cys
                85                  90                  95

Ala Asn Ile Tyr Ser His Tyr Trp Tyr Phe Asp Leu Trp Gly Arg Gly
            100                 105                 110

Thr Leu Val Thr Val Ser Ser
        115


<210> SEQ ID NO 114
<211> LENGTH: 107
<212> TYPE: PRT
<213> ORGANISM: Artificial
<220> FEATURE:
<223> OTHER INFORMATION: 6003-1286 LC

<400> SEQUENCE: 114

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Asn Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Leu
                85                  90                  95

Thr Phe Gly Gly Gly Thr Lys Val Glu Ile Lys
            100                 105


<210> SEQ ID NO 115
<211> LENGTH: 119
<212> TYPE: PRT
<213> ORGANISM: Artificial
<220> FEATURE:
<223> OTHER INFORMATION: 6003-30 HC

<400> SEQUENCE: 115

Glu Val Gln Val Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Thr Ile Ser Gly Arg Gly Gly Asn Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asp Ser Leu Arg Ala Glu Asp Thr Ala Val Tyr Tyr Cys
                85                  90                  95
```

```
Ala Ile Ile Pro Ser Leu Tyr Trp Tyr Phe Asp Leu Trp Gly Arg Gly
            100                 105                 110

Thr Leu Val Thr Val Ser Ser
        115


<210> SEQ ID NO 116
<211> LENGTH: 107
<212> TYPE: PRT
<213> ORGANISM: Artificial
<220> FEATURE:
<223> OTHER INFORMATION: 6003-30 LC

<400> SEQUENCE: 116

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Leu
                85                  90                  95

Thr Phe Gly Gly Gly Thr Lys Val Glu Ile Lys
            100                 105


<210> SEQ ID NO 117
<211> LENGTH: 116
<212> TYPE: PRT
<213> ORGANISM: Artificial
<220> FEATURE:
<223> OTHER INFORMATION: 6003-1277 HC

<400> SEQUENCE: 117

Gln Val Gln Leu Val Gln Ser Gly Ala Glu Val Lys Lys Pro Gly Ala
1               5                   10                  15

Ser Val Lys Val Ser Cys Lys Thr Ser Gly Tyr Thr Phe Thr His Tyr
            20                  25                  30

Gly Ile Ser Trp Val Arg Gln Ala Pro Gly Gln Gly Leu Glu Trp Met
        35                  40                  45

Gly Trp Ile Asn Thr Tyr Asn Gly Asn Thr Lys Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Ser Leu Gly Arg Asn Phe Asp Tyr Trp Gly Gln Gly Thr Leu Val
            100                 105                 110

Thr Val Ser Ser
        115


<210> SEQ ID NO 118
<211> LENGTH: 108
<212> TYPE: PRT
<213> ORGANISM: Artificial
<220> FEATURE:
<223> OTHER INFORMATION: 6003-1277 LC
```

<400> SEQUENCE: 118

Glu Ile Val Leu Thr Gln Ser Pro Ala Thr Leu Ser Leu Ser Pro Gly
1 5 10 15

Glu Arg Ala Thr Leu Ser Cys Arg Ala Ser Gln Ser Val Ser Ser Tyr
20 25 30

Leu Ala Trp Tyr Gln Gln Lys Pro Gly Gln Ala Pro Arg Leu Leu Ile
35 40 45

Tyr Asp Ala Ser Asn Arg Ala Thr Gly Ile Pro Ala Arg Phe Ser Gly
50 55 60

Ser Gly Ser Gly Thr Asp Phe Thr Leu Thr Ile Ser Ser Leu Glu Pro
65 70 75 80

Glu Asp Phe Ala Val Tyr Tyr Cys Gln Gln Arg Ser Asn Trp Pro Ala
85 90 95

Leu Thr Phe Gly Gly Gly Thr Lys Val Glu Ile Lys
100 105

<210> SEQ ID NO 119
<211> LENGTH: 117
<212> TYPE: PRT
<213> ORGANISM: Artificial
<220> FEATURE:
<223> OTHER INFORMATION: 6003-381 HC

<400> SEQUENCE: 119

Gln Val Gln Leu Val Glu Ser Gly Gly Gly Val Val Gln Pro Gly Arg
1 5 10 15

Ser Leu Arg Leu Ser Cys Ala Ala Ser Gly Phe Thr Phe Ser Asn Tyr
20 25 30

Val Met His Trp Val Arg Gln Ala Pro Gly Lys Gly Leu Glu Trp Val
35 40 45

Ala Ala Ile Ser Tyr Asn Gly Asn Asn Lys Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Ser Tyr Cys
85 90 95

Ala Lys Gly Leu Asn Asp Ala Phe Asp Ile Trp Gly Gln Gly Thr Met
100 105 110

Val Thr Val Ser Ser
115

<210> SEQ ID NO 120
<211> LENGTH: 108
<212> TYPE: PRT
<213> ORGANISM: Artificial
<220> FEATURE:
<223> OTHER INFORMATION: 6003-381 LC

<400> SEQUENCE: 120

Glu Ile Val Leu Thr Gln Ser Pro Ala Thr Leu Ser Leu Ser Pro Gly
1 5 10 15

Glu Arg Ala Thr Leu Ser Cys Arg Ala Ser Gln Ser Val Ser Gly Tyr
20 25 30

Leu Ala Trp Tyr Gln Gln Lys Pro Gly Gln Ala Pro Arg Leu Leu Ile
35 40 45

Tyr Asn Ala Ser Asn Arg Ala Thr Gly Ile Pro Ala Arg Phe Ser Gly
50 55 60

Ser Gly Ser Gly Thr Asp Phe Thr Leu Thr Ile Ser Ser Leu Glu Pro
65 70 75 80

Glu Asp Phe Ala Val Tyr Tyr Cys Gln Gln Arg Ser Asn Trp Pro Pro
85 90 95

Leu Thr Phe Gly Gly Gly Thr Lys Val Glu Ile Lys
100 105

<210> SEQ ID NO 121
<211> LENGTH: 119
<212> TYPE: PRT
<213> ORGANISM: Artificial
<220> FEATURE:
<223> OTHER INFORMATION: 6003-83 HC

<400> SEQUENCE: 121

Glu Val Gln Leu Leu Glu Ser Gly Gly Gly Leu Val Gln Pro Gly Gly
1 5 10 15

Ser Leu Arg Leu Ser Cys Ala Ala Ser Gly Phe Thr Phe Ser Ser Tyr
20 25 30

Ala Met Ser Trp Val Arg Gln Ala Pro Gly Lys Gly Leu Glu Trp Val
35 40 45

Ser Thr Ile Ser Gly Arg Gly Gly Ser Thr Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Ile Val Ala Thr Met Tyr Trp Tyr Phe Asp Leu Trp Gly Arg Gly
100 105 110

Thr Leu Val Thr Val Ser Ser
115

<210> SEQ ID NO 122
<211> LENGTH: 107
<212> TYPE: PRT
<213> ORGANISM: Artificial
<220> FEATURE:
<223> OTHER INFORMATION: 6003-83 LC

<400> SEQUENCE: 122

Glu Ile Val Leu Thr Gln Ser Pro Ala Thr Leu Ser Leu Ser Pro Gly
1 5 10 15

Glu Arg Ala Thr Leu Ser Cys Arg Ala Ser Gln Ser Val Ser Ser Tyr
20 25 30

Leu Ala Trp Tyr Gln Gln Lys Pro Gly Gln Ala Pro Arg Leu Leu Ile
35 40 45

Tyr Asp Ala Ser Asn Arg Ala Thr Gly Ile Pro Ala Arg Phe Ser Gly
50 55 60

Ser Gly Ser Gly Thr Asp Phe Thr Leu Thr Ile Ser Ser Leu Glu Pro
65 70 75 80

Glu Asp Phe Ala Val Tyr Tyr Cys Gln Gln Arg Ser Asn Trp Pro Ile
85 90 95

Thr Phe Gly Gln Gly Thr Arg Leu Glu Ile Lys
100 105

<210> SEQ ID NO 123
<211> LENGTH: 117
<212> TYPE: PRT
<213> ORGANISM: Artificial

```
<220> FEATURE:
<223> OTHER INFORMATION: 6003-799 HC

<400> SEQUENCE: 123

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Thr Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Leu Thr Gly Asp Ala Phe Asp Ile Trp Gly Gln Gly Thr Met
            100                 105                 110

Val Thr Val Ser Ser
        115


<210> SEQ ID NO 124
<211> LENGTH: 108
<212> TYPE: PRT
<213> ORGANISM: Artificial
<220> FEATURE:
<223> OTHER INFORMATION: 6003-799 LC

<400> SEQUENCE: 124

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Val Trp Tyr Gln Gln Lys Pro Gly Gln Ala Pro Arg Leu Leu Ile
        35                  40                  45

Tyr His Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Arg
                85                  90                  95

Ile Thr Phe Gly Gln Gly Thr Arg Leu Glu Ile Lys
            100                 105


<210> SEQ ID NO 125
<211> LENGTH: 124
<212> TYPE: PRT
<213> ORGANISM: Artificial
<220> FEATURE:
<223> OTHER INFORMATION: 6003-910 HC

<400> SEQUENCE: 125

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45
```

Ser Ala Ile Ser Gly Ser Gly Gly Ser Thr Tyr Tyr Val Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Lys Asp Ile Arg Gly Ile Gly Phe Gly Tyr Tyr Tyr Gly Met Asp
100 105 110

Val Trp Gly Gln Gly Thr Thr Val Thr Val Ser Ser
115 120

<210> SEQ ID NO 126
<211> LENGTH: 107
<212> TYPE: PRT
<213> ORGANISM: Artificial
<220> FEATURE:
<223> OTHER INFORMATION: 6003-910 LC

<400> SEQUENCE: 126

Glu Ile Val Leu Thr Gln Ser Pro Ala Thr Leu Ser Leu Ser Pro Gly
1 5 10 15

Glu Arg Ala Thr Leu Ser Cys Arg Ala Ser Gln Ser Val Ser Ser Tyr
20 25 30

Leu Val Trp Tyr Gln Gln Lys Pro Gly Gln Ala Pro Arg Leu Leu Ile
35 40 45

Tyr Asp Ala Ser Asn Arg Ala Thr Gly Ile Pro Ala Arg Phe Ser Gly
50 55 60

Ser Gly Ser Gly Thr Asp Phe Thr Leu Thr Ile Ser Ser Leu Glu Pro
65 70 75 80

Glu Asp Phe Ala Val Tyr Tyr Cys Gln Gln Arg Ser Asn Trp Pro Pro
85 90 95

Thr Phe Gly Gln Gly Thr Arg Leu Glu Ile Lys
100 105

<210> SEQ ID NO 127
<211> LENGTH: 117
<212> TYPE: PRT
<213> ORGANISM: Artificial
<220> FEATURE:
<223> OTHER INFORMATION: 6003-423 HC

<400> SEQUENCE: 127

Glu Val Gln Leu Leu Glu Ser Gly Gly Gly Leu Val Gln Pro Gly Gly
1 5 10 15

Ser Leu Arg Leu Ser Cys Glu Ala Ser Gly Phe Thr Phe Arg Ser Tyr
20 25 30

Val Met Ser Trp Val Arg Gln Ala Pro Gly Lys Gly Leu Glu Trp Val
35 40 45

Ser Thr Ile Ser Gly Gly Gly Gly Asn Thr Asn Tyr Thr Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Lys Asn Trp Gly Ser Gly Phe Asp Tyr Trp Gly Gln Gly Thr Leu
100 105 110

Val Thr Val Ser Ser
115

<210> SEQ ID NO 128
<211> LENGTH: 108
<212> TYPE: PRT
<213> ORGANISM: Artificial
<220> FEATURE:
<223> OTHER INFORMATION: 6003-423 LC

<400> SEQUENCE: 128

Glu Ile Val Leu Thr Gln Ser Pro Ala Thr Leu Ser Leu Ser Pro Gly
1 5 10 15

Glu Arg Ala Thr Leu Ser Cys Arg Ala Ser Gln Ser Val Ser Ser Tyr
20 25 30

Leu Ala Trp Tyr Gln Gln Lys Pro Gly Gln Ala Pro Arg Leu Leu Ile
35 40 45

Tyr Asp Ala Ser Asn Arg Ala Thr Gly Ile Pro Ala Arg Phe Ser Gly
50 55 60

Ser Gly Ser Gly Thr Asp Phe Thr Leu Thr Ile Ser Ser Leu Glu Pro
65 70 75 80

Glu Asp Phe Ala Val Tyr Tyr Cys Gln Gln Arg Ser Asn Trp Leu Ile
85 90 95

Phe Thr Phe Gly Pro Gly Thr Lys Val Asp Ile Lys
100 105

<210> SEQ ID NO 129
<211> LENGTH: 117
<212> TYPE: PRT
<213> ORGANISM: Artificial
<220> FEATURE:
<223> OTHER INFORMATION: 6003-822 HC

<400> SEQUENCE: 129

Glu Val Gln Leu Leu Glu Ser Gly Gly Gly Leu Val Gln Pro Gly Glu
1 5 10 15

Ser Leu Thr Leu Ser Cys Ala Ala Ser Gly Phe Thr Leu Ser Ser Tyr
20 25 30

Ala Met Ser Trp Val Arg Gln Ala Pro Gly Lys Gly Leu Glu Trp Val
35 40 45

Ser Ser Ile Ser Gly Arg Leu Gly Thr Thr Tyr Tyr Ala Ala Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Ile Tyr Ser Cys
85 90 95

Ala Lys Ala Pro Ser Asp Ala Phe Asp Ile Trp Gly Gln Gly Thr Met
100 105 110

Val Thr Val Ser Ser
115

<210> SEQ ID NO 130
<211> LENGTH: 108
<212> TYPE: PRT
<213> ORGANISM: Artificial
<220> FEATURE:
<223> OTHER INFORMATION: 6003-822 LC

<400> SEQUENCE: 130

Glu Ile Val Leu Thr Gln Ser Pro Ala Thr Leu Ser Leu Ser Pro Gly
1 5 10 15

```
Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Ile
                85                  90                  95

Phe Thr Phe Gly Pro Gly Thr Lys Val Asp Ile Lys
            100                 105
```

<210> SEQ ID NO 131
<211> LENGTH: 124
<212> TYPE: PRT
<213> ORGANISM: Artificial
<220> FEATURE:
<223> OTHER INFORMATION: 6003-886 HC

<400> SEQUENCE: 131

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Lys Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Asn Gly Asn Thr Asn Tyr Ala Gln Lys Leu
    50                  55                  60

Gln Asp Arg Val Thr Met Thr Thr Asp Thr Phe Thr Ser Thr Ala Tyr
65                  70                  75                  80

Met Glu Leu Arg Ser Leu Arg Ser Asp Asp Thr Ala Val Tyr Phe Cys
                85                  90                  95

Ala Arg Asp Gly Pro Leu Thr Gly Asp Phe Thr Phe Tyr Gly Met Asp
            100                 105                 110

Val Trp Gly Gln Gly Thr Thr Val Thr Val Ser Ser
        115                 120
```

<210> SEQ ID NO 132
<211> LENGTH: 108
<212> TYPE: PRT
<213> ORGANISM: Artificial
<220> FEATURE:
<223> OTHER INFORMATION: 6003-886 LC

<400> SEQUENCE: 132

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Pro
                85                  90                  95
```

Phe Thr Phe Gly Pro Gly Thr Lys Val Asp Ile Lys
100 105

<210> SEQ ID NO 133
<211> LENGTH: 121
<212> TYPE: PRT
<213> ORGANISM: Artificial
<220> FEATURE:
<223> OTHER INFORMATION: 6003-72 HC

<400> SEQUENCE: 133

Glu Val Gln Leu Leu Glu Ser Gly Gly Gly Leu Val Gln Pro Gly Gly
1 5 10 15

Ser Leu Arg Leu Ser Cys Ala Ala Ser Gly Phe Thr Phe Ser Ser Tyr
20 25 30

Ala Met Asn Trp Val Arg Gln Ala Pro Gly Lys Gly Leu Glu Trp Val
35 40 45

Ser Ala Ile Ser Gly Ser Gly Gly Ser Thr Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Met Ser Ser Leu Arg Ala Glu Asp Thr Ala Val Tyr Tyr Cys
85 90 95

Thr Arg Gly Arg Gly Ile Gly Tyr Tyr Asn Gly Met Asp Val Trp Gly
100 105 110

Gln Gly Thr Thr Val Thr Val Ser Ser
115 120

<210> SEQ ID NO 134
<211> LENGTH: 109
<212> TYPE: PRT
<213> ORGANISM: Artificial
<220> FEATURE:
<223> OTHER INFORMATION: 6003-72 LC

<400> SEQUENCE: 134

Glu Ile Val Leu Thr Gln Ser Pro Gly Thr Leu Ser Leu Ser Pro Gly
1 5 10 15

Glu Arg Ala Thr Leu Ser Cys Arg Ala Ser Gln Ser Val Ser Ser Ser
20 25 30

Tyr Leu Ala Trp Tyr Gln Gln Lys Pro Gly Gln Ala Pro Arg Leu Leu
35 40 45

Ile Tyr Gly Ala Ser Ser Arg Ala Thr Gly Ile Pro Asp Arg Phe Ser
50 55 60

Gly Ser Gly Ser Gly Thr Asp Phe Thr Leu Thr Ile Ser Arg Leu Glu
65 70 75 80

Pro Glu Asp Phe Ala Val Tyr Tyr Cys Gln Gln Tyr Gly Ser Ser Pro
85 90 95

Met Tyr Thr Phe Gly Gln Gly Thr Lys Leu Glu Ile Lys
100 105

<210> SEQ ID NO 135
<211> LENGTH: 120
<212> TYPE: PRT
<213> ORGANISM: Artificial
<220> FEATURE:
<223> OTHER INFORMATION: 6003-900 HC

<400> SEQUENCE: 135

```
Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Ser Ile Ser Ser Ser Ser Ser Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Arg Gly Ser Gly Ser Tyr Asp Ala Phe Asp Ile Trp Gly Gln
            100                 105                 110

Gly Thr Met Val Thr Val Ser Ser
        115                 120
```

<210> SEQ ID NO 136
<211> LENGTH: 107
<212> TYPE: PRT
<213> ORGANISM: Artificial
<220> FEATURE:
<223> OTHER INFORMATION: 6003-900 LC

<400> SEQUENCE: 136

```
Glu Ile Val Leu Thr Gln Ser Pro Asp Phe Gln Ser Val Thr Pro Lys
1               5                   10                  15

Glu Lys Val Thr Ile Thr Cys Arg Ala Ser Gln Ser Ile Gly Tyr Ser
            20                  25                  30

Leu His Trp Tyr Gln Gln Lys Pro Asp Gln Ser Pro Lys Leu Leu Ile
        35                  40                  45

Lys Tyr Ala Ser Gln Ser Phe Ser Gly Val Pro Ser Arg Phe Ser Gly
    50                  55                  60

Ser Gly Ser Gly Thr Asp Phe Thr Leu Thr Ile Asn Ser Leu Glu Ala
65                  70                  75                  80

Glu Asp Ala Ala Ala Tyr Tyr Cys His Gln Ser Ser Ser Leu Pro Leu
                85                  90                  95

Thr Phe Gly Gly Gly Thr Lys Val Glu Ile Lys
            100                 105
```

<210> SEQ ID NO 137
<211> LENGTH: 122
<212> TYPE: PRT
<213> ORGANISM: Artificial
<220> FEATURE:
<223> OTHER INFORMATION: 6003-936 HC

<400> SEQUENCE: 137

```
Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ile Phe Thr Ser Phe
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80
```

```
Leu Gln Trp Ser Ser Leu Lys Ala Ser Asp Thr Ala Met Tyr Tyr Cys
                85                  90                  95

Ala Arg His Ser Arg Gly Ser Phe Trp Tyr Gly Ala Phe Gln His Trp
            100                 105                 110

Gly Gln Gly Thr Leu Val Thr Val Ser Ser
        115                 120


<210> SEQ ID NO 138
<211> LENGTH: 107
<212> TYPE: PRT
<213> ORGANISM: Artificial
<220> FEATURE:
<223> OTHER INFORMATION: 6003-936 LC

<400> SEQUENCE: 138

Glu Ile Val Leu Thr Gln Ser Pro Asp Phe Gln Ser Val Thr Pro Lys
1               5                   10                  15

Glu Lys Val Thr Ile Thr Cys Arg Ala Ser Gln Ser Ile Gly Ser Ser
            20                  25                  30

Leu His Trp Tyr Gln Gln Lys Pro Asp Gln Ser Pro Lys Leu Leu Ile
        35                  40                  45

Lys Tyr Ala Ser Gln Ser Phe Ser Gly Val Pro Ser Arg Phe Ser Gly
    50                  55                  60

Ser Gly Ser Gly Thr Asp Phe Thr Leu Thr Ile Asn Ser Leu Glu Ala
65                  70                  75                  80

Glu Asp Ala Ala Ala Tyr Tyr Cys His Gln Ser Ser Ser Leu Pro His
                85                  90                  95

Thr Phe Gly Pro Gly Thr Lys Val Asp Ile Lys
            100                 105


<210> SEQ ID NO 139
<211> LENGTH: 124
<212> TYPE: PRT
<213> ORGANISM: Artificial
<220> FEATURE:
<223> OTHER INFORMATION: 6003-408 HC

<400> SEQUENCE: 139

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Ser Ile Ser Ser Ser Ser Ser Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Arg Arg Ile Ala Ala Ala Gly Thr Gly Tyr Gly Ala Phe Asp
            100                 105                 110

Ile Trp Gly Gln Gly Thr Met Val Thr Val Ser Ser
        115                 120


<210> SEQ ID NO 140
<211> LENGTH: 108
<212> TYPE: PRT
```

```
<213> ORGANISM: Artificial
<220> FEATURE:
<223> OTHER INFORMATION: 6003-408 LC

<400> SEQUENCE: 140

Ala Arg Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Thr Ser Ala
            20                  25                  30

Leu Ala Trp Tyr Gln Gln Lys Pro Gly Lys Val Pro Lys Leu Leu Ile
        35                  40                  45

Tyr Asp Ala Ser Ser Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Asn Gly Tyr Pro Met
                85                  90                  95

Phe Ser Phe Gly Gln Gly Thr Lys Leu Glu Ile Ile
            100                 105


<210> SEQ ID NO 141
<211> LENGTH: 122
<212> TYPE: PRT
<213> ORGANISM: Artificial
<220> FEATURE:
<223> OTHER INFORMATION: 6003-471 HC

<400> SEQUENCE: 141

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Asn Tyr
            20                  25                  30

Ala Ile Ser Trp Val Arg Gln Ala Pro Gly Gln Gly Leu Glu Trp Met
        35                  40                  45

Gly Arg Ile Ile Pro Ile Phe Gly Ile Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Arg Arg Gly Phe Ser Gly Tyr Glu Val Phe Asp Tyr Trp
            100                 105                 110

Gly Gln Gly Thr Leu Val Thr Val Ser Ser
        115                 120


<210> SEQ ID NO 142
<211> LENGTH: 107
<212> TYPE: PRT
<213> ORGANISM: Artificial
<220> FEATURE:
<223> OTHER INFORMATION: 6003-471 LC

<400> SEQUENCE: 142

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Glu Lys Ala Pro Lys Ser Leu Ile
        35                  40                  45
```

Tyr Ala Thr Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Ile
                85                  90                  95

Thr Phe Gly Gln Gly Thr Arg Leu Glu Ile Lys
            100                 105

<210> SEQ ID NO 143
<211> LENGTH: 119
<212> TYPE: PRT
<213> ORGANISM: Artificial
<220> FEATURE:
<223> OTHER INFORMATION: 6003-972 HC

<400> SEQUENCE: 143

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Asp Tyr
            20                  25                  30

Ala Met His Trp Val Arg Arg Ala Pro Gly Lys Gly Leu Glu Trp Val
        35                  40                  45

Val Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Pro Ser Gly Gly Trp Tyr Phe Asp Leu Trp Gly Arg Gly
            100                 105                 110

Thr Leu Val Thr Val Ser Ser
        115

<210> SEQ ID NO 144
<211> LENGTH: 107
<212> TYPE: PRT
<213> ORGANISM: Artificial
<220> FEATURE:
<223> OTHER INFORMATION: 6003-972 LC

<400> SEQUENCE: 144

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Leu Tyr Tyr Cys Gln Gln Arg Ser His Trp Pro Arg
                85                  90                  95

Thr Phe Gly Gln Gly Thr Lys Val Glu Ile Lys
            100                 105

<210> SEQ ID NO 145
<211> LENGTH: 831
<212> TYPE: PRT
<213> ORGANISM: Artificial
<220> FEATURE:
<223> OTHER INFORMATION: Human Sortilin Isofrom 1

<400> SEQUENCE: 145

```
Met Glu Arg Pro Trp Gly Ala Ala Asp Gly Leu Ser Arg Trp Pro His
1               5                   10                  15

Gly Leu Gly Leu Leu Leu Leu Leu Gln Leu Leu Pro Pro Ser Thr Leu
            20                  25                  30

Ser Gln Asp Arg Leu Asp Ala Pro Pro Pro Pro Ala Ala Pro Leu Pro
        35                  40                  45

Arg Trp Ser Gly Pro Ile Gly Val Ser Trp Gly Leu Arg Ala Ala Ala
    50                  55                  60

Ala Gly Gly Ala Phe Pro Arg Gly Gly Arg Trp Arg Arg Ser Ala Pro
65                  70                  75                  80

Gly Glu Asp Glu Glu Cys Gly Arg Val Arg Asp Phe Val Ala Lys Leu
                85                  90                  95

Ala Asn Asn Thr His Gln His Val Phe Asp Asp Leu Arg Gly Ser Val
            100                 105                 110

Ser Leu Ser Trp Val Gly Asp Ser Thr Gly Val Ile Leu Val Leu Thr
        115                 120                 125

Thr Phe His Val Pro Leu Val Ile Met Thr Phe Gly Gln Ser Lys Leu
    130                 135                 140

Tyr Arg Ser Glu Asp Tyr Gly Lys Asn Phe Lys Asp Ile Thr Asp Leu
145                 150                 155                 160

Ile Asn Asn Thr Phe Ile Arg Thr Glu Phe Gly Met Ala Ile Gly Pro
                165                 170                 175

Glu Asn Ser Gly Lys Val Val Leu Thr Ala Glu Val Ser Gly Gly Ser
            180                 185                 190

Arg Gly Gly Arg Ile Phe Arg Ser Ser Asp Phe Ala Lys Asn Phe Val
        195                 200                 205

Gln Thr Asp Leu Pro Phe His Pro Leu Thr Gln Met Met Tyr Ser Pro
    210                 215                 220

Gln Asn Ser Asp Tyr Leu Leu Ala Leu Ser Thr Glu Asn Gly Leu Trp
225                 230                 235                 240

Val Ser Lys Asn Phe Gly Gly Lys Trp Glu Glu Ile His Lys Ala Val
                245                 250                 255

Cys Leu Ala Lys Trp Gly Ser Asp Asn Thr Ile Phe Phe Thr Thr Tyr
            260                 265                 270

Ala Asn Gly Ser Cys Lys Ala Asp Leu Gly Ala Leu Glu Leu Trp Arg
        275                 280                 285

Thr Ser Asp Leu Gly Lys Ser Phe Lys Thr Ile Gly Val Lys Ile Tyr
    290                 295                 300

Ser Phe Gly Leu Gly Gly Arg Phe Leu Phe Ala Ser Val Met Ala Asp
305                 310                 315                 320

Lys Asp Thr Thr Arg Arg Ile His Val Ser Thr Asp Gln Gly Asp Thr
                325                 330                 335

Trp Ser Met Ala Gln Leu Pro Ser Val Gly Gln Glu Gln Phe Tyr Ser
            340                 345                 350

Ile Leu Ala Ala Asn Asp Asp Met Val Phe Met His Val Asp Glu Pro
        355                 360                 365

Gly Asp Thr Gly Phe Gly Thr Ile Phe Thr Ser Asp Asp Arg Gly Ile
```

```
    370                 375                 380

Val Tyr Ser Lys Ser Leu Asp Arg His Leu Tyr Thr Thr Thr Gly Gly
385                 390                 395                 400

Glu Thr Asp Phe Thr Asn Val Thr Ser Leu Arg Gly Val Tyr Ile Thr
                405                 410                 415

Ser Val Leu Ser Glu Asp Asn Ser Ile Gln Thr Met Ile Thr Phe Asp
            420                 425                 430

Gln Gly Gly Arg Trp Thr His Leu Arg Lys Pro Glu Asn Ser Glu Cys
        435                 440                 445

Asp Ala Thr Ala Lys Asn Lys Asn Glu Cys Ser Leu His Ile His Ala
    450                 455                 460

Ser Tyr Ser Ile Ser Gln Lys Leu Asn Val Pro Met Ala Pro Leu Ser
465                 470                 475                 480

Glu Pro Asn Ala Val Gly Ile Val Ile Ala His Gly Ser Val Gly Asp
                485                 490                 495

Ala Ile Ser Val Met Val Pro Asp Val Tyr Ile Ser Asp Asp Gly Gly
            500                 505                 510

Tyr Ser Trp Thr Lys Met Leu Glu Gly Pro His Tyr Tyr Thr Ile Leu
        515                 520                 525

Asp Ser Gly Gly Ile Ile Val Ala Ile Glu His Ser Ser Arg Pro Ile
    530                 535                 540

Asn Val Ile Lys Phe Ser Thr Asp Glu Gly Gln Cys Trp Gln Thr Tyr
545                 550                 555                 560

Thr Phe Thr Arg Asp Pro Ile Tyr Phe Thr Gly Leu Ala Ser Glu Pro
                565                 570                 575

Gly Ala Arg Ser Met Asn Ile Ser Ile Trp Gly Phe Thr Glu Ser Phe
            580                 585                 590

Leu Thr Ser Gln Trp Val Ser Tyr Thr Ile Asp Phe Lys Asp Ile Leu
        595                 600                 605

Glu Arg Asn Cys Glu Glu Lys Asp Tyr Thr Ile Trp Leu Ala His Ser
    610                 615                 620

Thr Asp Pro Glu Asp Tyr Glu Asp Gly Cys Ile Leu Gly Tyr Lys Glu
625                 630                 635                 640

Gln Phe Leu Arg Leu Arg Lys Ser Ser Val Cys Gln Asn Gly Arg Asp
                645                 650                 655

Tyr Val Val Thr Lys Gln Pro Ser Ile Cys Leu Cys Ser Leu Glu Asp
            660                 665                 670

Phe Leu Cys Asp Phe Gly Tyr Tyr Arg Pro Glu Asn Asp Ser Lys Cys
        675                 680                 685

Val Glu Gln Pro Glu Leu Lys Gly His Asp Leu Glu Phe Cys Leu Tyr
    690                 695                 700

Gly Arg Glu Glu His Leu Thr Thr Asn Gly Tyr Arg Lys Ile Pro Gly
705                 710                 715                 720

Asp Lys Cys Gln Gly Gly Val Asn Pro Val Arg Glu Val Lys Asp Leu
                725                 730                 735

Lys Lys Lys Cys Thr Ser Asn Phe Leu Ser Pro Glu Lys Gln Asn Ser
            740                 745                 750

Lys Ser Asn Ser Val Pro Ile Ile Leu Ala Ile Val Gly Leu Met Leu
        755                 760                 765

Val Thr Val Val Ala Gly Val Leu Ile Val Lys Lys Tyr Val Cys Gly
    770                 775                 780

Gly Arg Phe Leu Val His Arg Tyr Ser Val Leu Gln Gln His Ala Glu
785                 790                 795                 800
```

Ala Asn Gly Val Asp Gly Val Asp Ala Leu Asp Thr Ala Ser His Thr
805 810 815

Asn Lys Ser Gly Tyr His Asp Asp Ser Asp Glu Asp Leu Leu Glu
820 825 830

<210> SEQ ID NO 146
<211> LENGTH: 145
<212> TYPE: PRT
<213> ORGANISM: Artificial
<220> FEATURE:
<223> OTHER INFORMATION: E- Region

<400> SEQUENCE: 146

Cys Glu Glu Lys Asp Tyr Thr Ile Trp Leu Ala His Ser Thr Asp Pro
1 5 10 15

Glu Asp Tyr Glu Asp Gly Cys Ile Leu Gly Tyr Lys Glu Gln Phe Leu
20 25 30

Arg Leu Arg Lys Ser Ser Val Cys Gln Asn Gly Arg Asp Tyr Val Val
35 40 45

Thr Lys Gln Pro Ser Ile Cys Leu Cys Ser Leu Glu Asp Phe Leu Cys
50 55 60

Asp Phe Gly Tyr Tyr Arg Pro Glu Asn Asp Ser Lys Cys Val Glu Gln
65 70 75 80

Pro Glu Leu Lys Gly His Asp Leu Glu Phe Cys Leu Tyr Gly Arg Glu
85 90 95

Glu His Leu Thr Thr Asn Gly Tyr Arg Lys Ile Pro Gly Asp Lys Cys
100 105 110

Gln Gly Gly Val Asn Pro Val Arg Glu Val Lys Asp Leu Lys Lys Lys
115 120 125

Cys Thr Ser Asn Phe Leu Ser Pro Glu Lys Gln Asn Ser Lys Ser Asn
130 135 140

Ser
145

<210> SEQ ID NO 147
<211> LENGTH: 700
<212> TYPE: PRT
<213> ORGANISM: Artificial
<220> FEATURE:
<223> OTHER INFORMATION: Sortilin “hSORTECDBAP”

<400> SEQUENCE: 147

Ser Ala Pro Gly Glu Asp Glu Glu Cys Gly Arg Val Arg Asp Phe Val
1 5 10 15

Ala Lys Leu Ala Asn Asn Thr His Gln His Val Phe Asp Asp Leu Arg
20 25 30

Gly Ser Val Ser Leu Ser Trp Val Gly Asp Ser Thr Gly Val Ile Leu
35 40 45

Val Leu Thr Thr Phe His Val Pro Leu Val Ile Met Thr Phe Gly Gln
50 55 60

Ser Lys Leu Tyr Arg Ser Glu Asp Tyr Gly Lys Asn Phe Lys Asp Ile
65 70 75 80

Thr Asp Leu Ile Asn Asn Thr Phe Ile Arg Thr Glu Phe Gly Met Ala
85 90 95

Ile Gly Pro Glu Asn Ser Gly Lys Val Val Leu Thr Ala Glu Val Ser
100 105 110

Gly Gly Ser Arg Gly Gly Arg Ile Phe Arg Ser Ser Asp Phe Ala Lys

-continued

```
        115                 120                 125

Asn Phe Val Gln Thr Asp Leu Pro Phe His Pro Leu Thr Gln Met Met
    130                 135                 140

Tyr Ser Pro Gln Asn Ser Asp Tyr Leu Leu Ala Leu Ser Thr Glu Asn
145                 150                 155                 160

Gly Leu Trp Val Ser Lys Asn Phe Gly Gly Lys Trp Glu Glu Ile His
                165                 170                 175

Lys Ala Val Cys Leu Ala Lys Trp Gly Ser Asp Asn Thr Ile Phe Phe
            180                 185                 190

Thr Thr Tyr Ala Asn Gly Ser Cys Lys Ala Asp Leu Gly Ala Leu Glu
        195                 200                 205

Leu Trp Arg Thr Ser Asp Leu Gly Lys Ser Phe Lys Thr Ile Gly Val
    210                 215                 220

Lys Ile Tyr Ser Phe Gly Leu Gly Gly Arg Phe Leu Phe Ala Ser Val
225                 230                 235                 240

Met Ala Asp Lys Asp Thr Thr Arg Arg Ile His Val Ser Thr Asp Gln
                245                 250                 255

Gly Asp Thr Trp Ser Met Ala Gln Leu Pro Ser Val Gly Gln Glu Gln
            260                 265                 270

Phe Tyr Ser Ile Leu Ala Ala Asn Asp Asp Met Val Phe Met His Val
        275                 280                 285

Asp Glu Pro Gly Asp Thr Gly Phe Gly Thr Ile Phe Thr Ser Asp Asp
    290                 295                 300

Arg Gly Ile Val Tyr Ser Lys Ser Leu Asp Arg His Leu Tyr Thr Thr
305                 310                 315                 320

Thr Gly Gly Glu Thr Asp Phe Thr Asn Val Thr Ser Leu Arg Gly Val
                325                 330                 335

Tyr Ile Thr Ser Val Leu Ser Glu Asp Asn Ser Ile Gln Thr Met Ile
            340                 345                 350

Thr Phe Asp Gln Gly Gly Arg Trp Thr His Leu Arg Lys Pro Glu Asn
        355                 360                 365

Ser Glu Cys Asp Ala Thr Ala Lys Asn Lys Asn Glu Cys Ser Leu His
    370                 375                 380

Ile His Ala Ser Tyr Ser Ile Ser Gln Lys Leu Asn Val Pro Met Ala
385                 390                 395                 400

Pro Leu Ser Glu Pro Asn Ala Val Gly Ile Val Ile Ala His Gly Ser
                405                 410                 415

Val Gly Asp Ala Ile Ser Val Met Val Pro Asp Val Tyr Ile Ser Asp
            420                 425                 430

Asp Gly Gly Tyr Ser Trp Thr Lys Met Leu Glu Gly Pro His Tyr Tyr
        435                 440                 445

Thr Ile Leu Asp Ser Gly Gly Ile Ile Val Ala Ile Glu His Ser Ser
    450                 455                 460

Arg Pro Ile Asn Val Ile Lys Phe Ser Thr Asp Glu Gly Gln Cys Trp
465                 470                 475                 480

Gln Thr Tyr Thr Phe Thr Arg Asp Pro Ile Tyr Phe Thr Gly Leu Ala
                485                 490                 495

Ser Glu Pro Gly Ala Arg Ser Met Asn Ile Ser Ile Trp Gly Phe Thr
            500                 505                 510

Glu Ser Phe Leu Thr Ser Gln Trp Val Ser Tyr Thr Ile Asp Phe Lys
        515                 520                 525

Asp Ile Leu Glu Arg Asn Cys Glu Glu Lys Asp Tyr Thr Ile Trp Leu
    530                 535                 540
```

```
Ala His Ser Thr Asp Pro Glu Asp Tyr Glu Asp Gly Cys Ile Leu Gly
545                 550                 555                 560

Tyr Lys Glu Gln Phe Leu Arg Leu Arg Lys Ser Ser Val Cys Gln Asn
                565                 570                 575

Gly Arg Asp Tyr Val Val Thr Lys Gln Pro Ser Ile Cys Leu Cys Ser
            580                 585                 590

Leu Glu Asp Phe Leu Cys Asp Phe Gly Tyr Tyr Arg Pro Glu Asn Asp
        595                 600                 605

Ser Lys Cys Val Glu Gln Pro Glu Leu Lys Gly His Asp Leu Glu Phe
    610                 615                 620

Cys Leu Tyr Gly Arg Glu Glu His Leu Thr Thr Asn Gly Tyr Arg Lys
625                 630                 635                 640

Ile Pro Gly Asp Lys Cys Gln Gly Gly Val Asn Pro Val Arg Glu Val
                645                 650                 655

Lys Asp Leu Lys Lys Lys Cys Thr Ser Asn Phe Leu Ser Pro Glu Lys
            660                 665                 670

Gln Asn Ser Lys Ser Asn Gly Ser Ala Gly Gly Ser Gly Gly Leu Asn
        675                 680                 685

Asp Ile Phe Glu Ala Gln Lys Ile Glu Trp His Glu
    690                 695                 700


<210> SEQ ID NO 148
<211> LENGTH: 700
<212> TYPE: PRT
<213> ORGANISM: Artificial
<220> FEATURE:
<223> OTHER INFORMATION: Sortilin SORTECDBAP_hBACK

<400> SEQUENCE: 148

Ser Ala Pro Gly Glu Asp Glu Glu Cys Gly Arg Val Arg Asp Phe Val
1               5                   10                  15

Ala Lys Leu Ala Asn Asn Thr His Gln His Ile Phe Asn Asp Leu Ser
            20                  25                  30

Gly Ser Val Ser Leu Ser Trp Val Gly Asp Ser Thr Gly Val Ile Leu
        35                  40                  45

Val Leu Thr Thr Phe Gln Val Pro Ile Phe Met Ile Thr Ile Gly Gln
    50                  55                  60

Ser Lys Leu Tyr Arg Ser Glu Asp Tyr Gly Lys Asn Phe Lys Asp Ile
65                  70                  75                  80

Thr Asp Leu Ile Asn Asn Thr Phe Ile Arg Ser Asp Phe Gly Ile Ala
                85                  90                  95

Ile Gly Pro Glu Asn Ser Gly Lys Val Val Leu Thr Ala Asp Val Ser
            100                 105                 110

Gly Ser His Gly Ser Arg Ile Phe Arg Ser Ser Asp Phe Ala Lys Asn
        115                 120                 125

Phe Val Gln Gln Glu Leu Pro Phe Val Pro Leu Met Gln Ile Met Tyr
    130                 135                 140

Ser Pro Gln Asn Ser Asp Tyr Leu Leu Ala Leu Ser Asn Lys Asn Glu
145                 150                 155                 160

Leu Trp Val Ser Lys Asn Phe Gly Gly Lys Trp Glu Lys Leu Tyr Asp
                165                 170                 175

Thr Val Cys Leu Ala Lys Trp Gly Ser Asp Asn Thr Ile Phe Phe Thr
            180                 185                 190

Ala Asn His Asn Gly Ser Cys Ser Asn Asp Arg Gly Met Leu Glu Leu
        195                 200                 205
```

```
Trp Arg Thr Ser Asp Leu Gly Lys Ser Phe Lys Thr Ile Gly Ser Lys
    210                 215                 220

Ile Tyr Ser Phe Gly Leu Gly Gly Arg Phe Leu Phe Ala Ser Val Met
225                 230                 235                 240

Thr Gly Lys Gly Thr Leu Arg Ala Ile His Val Ser Thr Asp Gln Gly
                245                 250                 255

Asp Thr Trp Ser Met Ala Gln Leu Pro Pro Val Gly His Glu Gln Phe
            260                 265                 270

Tyr Ser Ile Leu Ala Ala Asn Asp Asp Met Val Phe Met His Val Asp
        275                 280                 285

Glu Pro Gly Asp Ser Gly Phe Gly Thr Ile Phe Thr Ser Asp Asp Arg
    290                 295                 300

Gly Ile Val Tyr Ser Lys Ser Leu Glu Arg His Leu Tyr Thr Thr Thr
305                 310                 315                 320

Gly Gly Glu Thr Asp Phe Thr Asn Val Thr Ser Leu Arg Gly Val Tyr
                325                 330                 335

Ile Thr Ser Ile Leu Ala Glu Asp Lys Ser Val Gln Ser Met Ile Thr
            340                 345                 350

Phe Asp Gln Gly Gly Arg Trp Thr His Leu Arg Lys Pro Glu Asn Ser
        355                 360                 365

Lys Cys Asp Ala Thr Ala Arg Asp Pro Glu Lys Cys Ser Leu His Ile
    370                 375                 380

His Ala Ala Tyr Ser Ile Ala Thr Gly Leu Asn Val Pro Met Leu Pro
385                 390                 395                 400

Leu Ser Glu Pro Asn Ala Val Gly Ile Val Ile Ala His Gly Ser Val
                405                 410                 415

Gly Asp Ala Ile Ser Val Met Arg Pro Asp Val Tyr Ile Ser Asp Asp
            420                 425                 430

Gly Gly Tyr Ser Trp Thr Lys Ala Leu Glu Gly Pro His His Tyr Thr
        435                 440                 445

Ile Leu Asp Ser Gly Gly Ile Ile Val Ala Val Glu Gln Asn Ala His
    450                 455                 460

Gln Gly Val Asn Gln Ile Lys Phe Ser Thr Asp Glu Gly Gln Cys Trp
465                 470                 475                 480

Gln Thr Tyr Asn Phe Thr Lys Asp Pro Ile Phe Phe Thr Gly Leu Ala
                485                 490                 495

Ser Glu Pro Gly Ala Arg Ser Met Asn Ile Ser Ile Trp Gly Tyr Arg
            500                 505                 510

Ser Ser Leu Phe His Gln Tyr Trp Ile Ser Tyr Thr Ile Asp Phe Lys
        515                 520                 525

Asp Ile Leu Glu Arg Asn Cys Glu Glu Lys Asp Tyr Thr Ile Trp Leu
    530                 535                 540

Ala His Ser Thr Asp Pro Glu Asp Tyr Glu Asp Gly Cys Ile Leu Gly
545                 550                 555                 560

Tyr Lys Glu Gln Phe Leu Arg Leu Arg Lys Ser Ser Val Cys Gln Asn
                565                 570                 575

Gly Arg Asp Tyr Val Val Thr Lys Gln Pro Ser Ile Cys Leu Cys Ser
            580                 585                 590

Leu Glu Asp Phe Leu Cys Asp Phe Gly Tyr Tyr Arg Pro Glu Asn Asp
        595                 600                 605

Ser Lys Cys Val Glu Gln Pro Glu Leu Lys Gly His Asp Leu Glu Phe
    610                 615                 620
```

Cys Leu Tyr Gly Arg Glu Glu His Leu Thr Thr Asn Gly Tyr Arg Lys
625 630 635 640

Ile Pro Gly Asp Lys Cys Gln Gly Gly Val Asn Pro Val Arg Glu Val
645 650 655

Lys Asp Leu Lys Lys Lys Cys Thr Ser Asn Phe Leu Ser Pro Glu Lys
660 665 670

Gln Asn Ser Lys Ser Asn Gly Ser Ala Gly Gly Ser Gly Gly Leu Asn
675 680 685

Asp Ile Phe Glu Ala Gln Lys Ile Glu Trp His Glu
690 695 700

<210> SEQ ID NO 149
<211> LENGTH: 700
<212> TYPE: PRT
<213> ORGANISM: Artificial
<220> FEATURE:
<223> OTHER INFORMATION: Sortilin SORTECDBAP_tetra

<400> SEQUENCE: 149

Arg Ser Thr Glu Gln Gly Glu Ser Cys Ser Gly Leu Leu Gly Ala Asp
1 5 10 15

Ala Lys Leu Ala Gly Asn Thr His Gln His Ile Phe Asn Asp Leu Ser
20 25 30

Gly Ser Val Ser Leu Ala Trp Val Gly Asp Gly Thr Gly Val Ile Leu
35 40 45

Ala Leu Thr Thr Phe Gln Val Pro Ile Phe Met Ile Thr Ile Gly Gln
50 55 60

Ser Lys Leu Tyr Arg Ser Glu Asp Tyr Gly Lys Ser Phe Glu Asp Val
65 70 75 80

Thr Asn Leu Ile Asn Asn Thr Phe Ile Arg Ser Asp Phe Gly Ile Ala
85 90 95

Ile Gly Pro Glu Asn Ser Gly Lys Val Ile Leu Thr Ala Asp Val Ser
100 105 110

Gly Ser His Gly Ser Arg Ile Phe Val Ser Ser Asp Phe Gly Lys Ser
115 120 125

Phe Thr His Gln Glu Leu Pro Phe Val Pro Leu Met Gln Ile Thr Tyr
130 135 140

Asn Pro Glu Asn Ser Asn Val Leu Leu Ala Leu Ser Asn Lys Asn Glu
145 150 155 160

Leu Trp Leu Ser Glu Asp Phe Gly Thr Asn Trp Lys Lys Leu Tyr Asp
165 170 175

Thr Val Cys Leu Ala Lys Trp Gly Arg Lys Gly Thr Ile Phe Phe Thr
180 185 190

Ala Asn His Asn Gly Ser Cys Ser Asn Asp Arg Gly Met Leu Glu Leu
195 200 205

Glu Arg Thr Thr Asp Tyr Gly Lys Ser Phe Lys Thr Val Ala Ser Lys
210 215 220

Ile Tyr Ser Phe Gly Leu Gly Gly Lys Phe Leu Phe Ala Ser Val Met
225 230 235 240

Thr Gly Lys Gly Thr Leu Arg Ala Ile His Val Ser Val Asp Asp Gly
245 250 255

Asp Thr Trp Asn Met Ala Gln Leu Pro Pro Val Gly His Glu Gln Phe
260 265 270

Tyr Ser Ile Leu Ala Ala Asn Asp Glu Met Val Phe Met His Val Asp
275 280 285

-continued

```
Glu Pro Gly Asp Ser Gly Phe Gly Thr Ile Tyr Val Ser Asp Asp Arg
    290                 295                 300

Gly Thr Val Tyr Ser Lys Ser Leu Glu Arg His Leu Tyr Thr Thr Thr
305                 310                 315                 320

Gly Gly Glu Thr Asp Phe Ile Asn Val Thr Ser Leu Arg Gly Val Phe
                325                 330                 335

Thr Thr Ser Ile Leu Ala Glu Asp Lys Ser Val Gln Ser Val Ile Ser
            340                 345                 350

Phe Asp Gln Gly Gly Glu Trp Val Pro Leu Arg Lys Pro Ala Asp Ser
        355                 360                 365

Lys Cys Asp Ala Thr Ala Arg Asp Pro Glu Lys Cys Ser Leu His Ile
    370                 375                 380

His Ala Ala Tyr Ser Ile Ala Thr Gly Leu Asn Val Pro Met Leu Pro
385                 390                 395                 400

Leu Ser Glu Pro Asn Ala Val Gly Leu Val Leu Ala His Gly Ser Val
                405                 410                 415

Gly Asp Ala Ile Ser Val Met Arg Pro Asp Val Tyr Val Ser Asp Asp
            420                 425                 430

Gly Gly Tyr Thr Trp Ile Lys Ala Leu Glu Gly Pro His His Tyr Ala
        435                 440                 445

Ile Leu Asp Ser Gly Gly Leu Leu Val Ala Val Glu Gln Asn Ala His
    450                 455                 460

Gln Gly Val Asn Gln Ile Lys Phe Ser Thr Asp Glu Gly Gln Cys Trp
465                 470                 475                 480

Gly Val Tyr Asn Phe Thr Lys Asp Pro Ile Phe Phe Thr Gly Leu Ala
                485                 490                 495

Ser Glu Pro Gly Ala Arg Ser Met Asn Val Ser Leu Trp Gly Tyr Arg
            500                 505                 510

Ser Ser Leu Phe His Gln Tyr Trp Ile Ser Phe Thr Ile Asp Phe Arg
        515                 520                 525

Asp Leu Ile Thr Arg Asn Cys Thr Asp Lys Asp Tyr Val Gln Trp Leu
    530                 535                 540

Ala His Ser Asp Asp Ile Ser Asp Pro Asn Asp Gly Cys Met Leu Gly
545                 550                 555                 560

Tyr Lys Glu Lys Phe Leu Arg Leu Lys Lys Asp Ser Val Cys Leu Asn
                565                 570                 575

Gly Arg Asp Tyr Glu Val Asn Thr Gln Pro Thr Pro Cys Leu Cys Thr
            580                 585                 590

Leu Asp Asp Phe Leu Cys Asp Phe Gly Tyr Tyr Arg Lys Glu Asn Ser
        595                 600                 605

Ser Glu Cys Val Glu Gln Pro Asp Leu Lys Gly Lys Val Leu Glu Phe
    610                 615                 620

Cys Leu His Gly Thr Glu Glu Glu Leu Leu Thr Asn Gly Tyr Arg Lys
625                 630                 635                 640

Ile Pro Gly Asp Lys Cys Glu Gly Gly Gln Ile Pro Glu Arg Lys Glu
                645                 650                 655

Ile Asn Leu Arg Arg Arg Cys Val Ser Asp Leu Leu Gly Pro Glu Phe
            660                 665                 670

Leu Val Lys Lys Ser Ser Gly Ser Ala Gly Gly Ser Gly Gly Leu Asn
        675                 680                 685

Asp Ile Phe Glu Ala Gln Lys Ile Glu Trp His Glu
    690                 695                 700
```

<210> SEQ ID NO 150
<211> LENGTH: 701
<212> TYPE: PRT
<213> ORGANISM: Artificial
<220> FEATURE:
<223> OTHER INFORMATION: Sortilin SORTECDBAP_hB01-05

<400> SEQUENCE: 150

Ser Ala Pro Gly Glu Asp Glu Glu Cys Gly Arg Val Arg Asp Phe Val
1 5 10 15

Ala Lys Leu Ala Asn Asn Thr His Gln His Val Phe Asp Asp Leu Arg
20 25 30

Gly Ser Val Ser Leu Ser Trp Val Gly Asp Ser Thr Gly Val Ile Leu
35 40 45

Val Leu Thr Thr Phe His Val Pro Leu Val Ile Met Thr Phe Gly Gln
50 55 60

Ser Lys Leu Tyr Arg Ser Glu Asp Tyr Gly Lys Asn Phe Lys Asp Ile
65 70 75 80

Thr Asp Leu Ile Asn Asn Thr Phe Ile Arg Thr Glu Phe Gly Met Ala
85 90 95

Ile Gly Pro Glu Asn Ser Gly Lys Val Val Leu Thr Ala Glu Val Ser
100 105 110

Gly Gly Ser Arg Gly Gly Arg Ile Phe Arg Ser Ser Asp Phe Ala Lys
115 120 125

Asn Phe Val Gln Thr Asp Leu Pro Phe His Pro Leu Thr Gln Met Met
130 135 140

Tyr Ser Pro Gln Asn Ser Asp Tyr Leu Leu Ala Leu Ser Thr Glu Asn
145 150 155 160

Gly Leu Trp Val Ser Lys Asn Phe Gly Gly Lys Trp Glu Glu Ile His
165 170 175

Lys Ala Val Cys Leu Ala Lys Trp Gly Ser Asp Asn Thr Ile Phe Phe
180 185 190

Thr Thr Tyr Ala Asn Gly Ser Cys Lys Ala Asp Leu Gly Ala Leu Glu
195 200 205

Leu Trp Arg Thr Ser Asp Leu Gly Lys Ser Phe Lys Thr Ile Gly Val
210 215 220

Lys Ile Tyr Ser Phe Gly Leu Gly Gly Arg Phe Leu Phe Ala Ser Val
225 230 235 240

Met Ala Asp Lys Asp Thr Thr Arg Arg Ile His Val Ser Thr Asp Gln
245 250 255

Gly Asp Thr Trp Ser Met Ala Gln Leu Pro Pro Val Gly His Glu Gln
260 265 270

Phe Tyr Ser Ile Leu Ala Ala Asn Asp Glu Met Val Phe Met His Val
275 280 285

Asp Glu Pro Gly Asp Ser Gly Phe Gly Thr Ile Tyr Val Ser Asp Asp
290 295 300

Arg Gly Thr Val Tyr Ser Lys Ser Leu Glu Arg His Leu Tyr Thr Thr
305 310 315 320

Thr Gly Gly Glu Thr Asp Phe Ile Asn Val Thr Ser Leu Arg Gly Val
325 330 335

Phe Thr Thr Ser Ile Leu Ala Glu Asp Lys Ser Val Gln Ser Val Ile
340 345 350

Ser Phe Asp Gln Gly Gly Glu Trp Val Pro Leu Arg Lys Pro Ala Asp
355 360 365

Ser Lys Cys Asp Ala Thr Ala Arg Asp Pro Glu Lys Cys Ser Leu His

```
    370                 375                 380

Ile His Ala Ala Tyr Ser Ile Ala Thr Gly Leu Asn Val Pro Met Leu
385                 390                 395                 400

Pro Leu Ser Glu Pro Asn Ala Val Gly Leu Val Leu Ala His Gly Ser
                405                 410                 415

Val Gly Asp Ala Ile Ser Val Met Arg Pro Asp Val Tyr Val Ser Asp
            420                 425                 430

Asp Gly Gly Tyr Thr Trp Ile Lys Ala Leu Glu Gly Pro His His Tyr
        435                 440                 445

Ala Ile Leu Asp Ser Gly Gly Leu Leu Val Ala Val Glu Gln Asn Ala
    450                 455                 460

His Gln Gly Val Asn Gln Ile Lys Phe Ser Thr Asp Glu Gly Gln Cys
465                 470                 475                 480

Trp Gly Val Tyr Asn Phe Thr Lys Asp Pro Ile Phe Phe Thr Gly Leu
                485                 490                 495

Ala Ser Glu Pro Gly Ala Arg Ser Met Asn Val Ser Leu Trp Gly Tyr
            500                 505                 510

Arg Ser Ser Leu Phe His Gln Tyr Trp Ile Ser Phe Thr Ile Asp Phe
        515                 520                 525

Arg Asp Leu Ile Thr Arg Asn Cys Thr Asp Lys Asp Tyr Val Gln Trp
    530                 535                 540

Leu Ala His Ser Asp Asp Ile Ser Asp Pro Asn Asp Gly Cys Met Leu
545                 550                 555                 560

Gly Tyr Lys Glu Lys Phe Leu Arg Leu Lys Lys Asp Ser Val Cys Leu
                565                 570                 575

Asn Gly Arg Asp Tyr Glu Val Asn Thr Gln Pro Thr Pro Cys Leu Cys
            580                 585                 590

Thr Leu Asp Asp Phe Leu Cys Asp Phe Gly Tyr Tyr Arg Lys Glu Asn
        595                 600                 605

Ser Ser Glu Cys Val Glu Gln Pro Asp Leu Lys Gly Lys Val Leu Glu
    610                 615                 620

Phe Cys Leu His Gly Thr Glu Glu Glu Leu Leu Thr Asn Gly Tyr Arg
625                 630                 635                 640

Lys Ile Pro Gly Asp Lys Cys Glu Gly Gly Gln Ile Pro Glu Arg Lys
                645                 650                 655

Glu Ile Asn Leu Arg Arg Arg Cys Val Ser Asp Leu Leu Gly Pro Glu
            660                 665                 670

Phe Leu Val Lys Lys Ser Ser Gly Ser Ala Gly Gly Ser Gly Gly Leu
        675                 680                 685

Asn Asp Ile Phe Glu Ala Gln Lys Ile Glu Trp His Glu
    690                 695                 700


<210> SEQ ID NO 151
<211> LENGTH: 700
<212> TYPE: PRT
<213> ORGANISM: Artificial
<220> FEATURE:
<223> OTHER INFORMATION: Sortilin  SORTECDBAP_hRIM

<400> SEQUENCE: 151

Ser Ala Pro Gly Glu Asp Glu Glu Cys Gly Arg Val Arg Asp Phe Val
1               5                   10                  15

Ala Lys Leu Ala Asn Asn Thr His Gln His Val Phe Asp Asp Leu Arg
            20                  25                  30

Gly Ser Val Ser Leu Ala Trp Val Gly Asp Gly Thr Gly Val Ile Leu
```

```
        35                  40                  45

Ala Leu Thr Thr Phe Gln Val Pro Ile Phe Met Ile Thr Ile Gly Gln
    50                  55                  60

Ser Lys Leu Tyr Arg Ser Glu Asp Tyr Gly Lys Asn Phe Lys Asp Ile
65                  70                  75                  80

Thr Asp Leu Ile Asn Asn Thr Phe Ile Arg Ser Asp Phe Gly Ile Ala
                85                  90                  95

Ile Gly Pro Glu Asn Ser Gly Lys Val Ile Leu Thr Ala Asp Val Ser
            100                 105                 110

Gly Ser His Gly Ser Arg Ile Phe Arg Ser Ser Asp Phe Ala Lys Asn
        115                 120                 125

Phe Val Gln Thr Asp Leu Pro Phe Val Pro Leu Met Gln Ile Thr Tyr
    130                 135                 140

Asn Pro Glu Asn Ser Asn Val Leu Leu Ala Leu Ser Asn Lys Asn Glu
145                 150                 155                 160

Leu Trp Val Ser Lys Asn Phe Gly Gly Lys Trp Glu Glu Ile His Asp
                165                 170                 175

Thr Val Cys Leu Ala Lys Trp Gly Arg Lys Gly Thr Ile Phe Phe Thr
            180                 185                 190

Ala Asn His Asn Gly Ser Cys Ser Asn Asp Arg Gly Met Leu Glu Leu
        195                 200                 205

Trp Arg Thr Ser Asp Leu Gly Lys Ser Phe Lys Thr Ile Gly Val Lys
    210                 215                 220

Ile Tyr Ser Phe Gly Leu Gly Gly Lys Phe Leu Phe Ala Ser Val Met
225                 230                 235                 240

Thr Gly Lys Gly Thr Leu Arg Arg Ile His Val Ser Thr Asp Gln Gly
                245                 250                 255

Asp Thr Trp Ser Met Ala Gln Leu Pro Ser Val Gly His Glu Gln Phe
            260                 265                 270

Tyr Ser Ile Leu Ala Ala Asn Asp Glu Met Val Phe Met His Val Asp
        275                 280                 285

Glu Pro Gly Asp Ser Gly Phe Gly Thr Ile Phe Thr Ser Asp Asp Arg
    290                 295                 300

Gly Ile Val Tyr Ser Lys Ser Leu Asp Arg His Leu Tyr Thr Thr Thr
305                 310                 315                 320

Gly Gly Glu Thr Asp Phe Ile Asn Val Thr Ser Leu Arg Gly Val Phe
                325                 330                 335

Thr Thr Ser Ile Leu Ala Glu Asp Lys Ser Ile Gln Thr Met Ile Thr
            340                 345                 350

Phe Asp Gln Gly Gly Arg Trp Thr His Leu Arg Lys Pro Glu Asn Ser
        355                 360                 365

Glu Cys Asp Ala Thr Ala Lys Asn Lys Asn Glu Cys Ser Leu His Ile
    370                 375                 380

His Ala Ala Tyr Ser Ile Ala Thr Gly Leu Asn Val Pro Met Leu Pro
385                 390                 395                 400

Leu Ser Glu Pro Asn Ala Val Gly Leu Val Leu Ala His Gly Ser Val
                405                 410                 415

Gly Asp Ala Ile Ser Val Met Arg Pro Asp Val Tyr Ile Ser Asp Asp
            420                 425                 430

Gly Gly Tyr Ser Trp Thr Lys Met Leu Glu Gly Pro His His Tyr Ala
        435                 440                 445

Ile Leu Asp Ser Gly Gly Leu Leu Val Ala Val Glu Gln Asn Ala His
    450                 455                 460
```

```
Gln Gly Val Asn Val Ile Lys Phe Ser Thr Asp Glu Gly Gln Cys Trp
465                 470                 475                 480

Gln Thr Tyr Thr Phe Thr Arg Asp Pro Ile Phe Phe Thr Gly Leu Ala
                485                 490                 495

Ser Glu Pro Gly Ala Arg Ser Met Asn Val Ser Leu Trp Gly Tyr Arg
            500                 505                 510

Ser Ser Leu Phe His Gln Gln Trp Val Ser Tyr Thr Ile Asp Phe Lys
        515                 520                 525

Asp Ile Leu Glu Arg Asn Cys Glu Glu Lys Asp Tyr Thr Ile Trp Leu
    530                 535                 540

Ala His Ser Thr Asp Pro Glu Asp Tyr Glu Asp Gly Cys Ile Leu Gly
545                 550                 555                 560

Tyr Lys Glu Gln Phe Leu Arg Leu Arg Lys Ser Ser Val Cys Gln Asn
                565                 570                 575

Gly Arg Asp Tyr Val Val Thr Lys Gln Pro Ser Ile Cys Leu Cys Ser
            580                 585                 590

Leu Glu Asp Phe Leu Cys Asp Phe Gly Tyr Tyr Arg Pro Glu Asn Asp
        595                 600                 605

Ser Lys Cys Val Glu Gln Pro Glu Leu Lys Gly His Asp Leu Glu Phe
    610                 615                 620

Cys Leu Tyr Gly Arg Glu Glu His Leu Thr Thr Asn Gly Tyr Arg Lys
625                 630                 635                 640

Ile Pro Gly Asp Lys Cys Gln Gly Gly Val Asn Pro Val Arg Glu Val
                645                 650                 655

Lys Asp Leu Lys Lys Lys Cys Thr Ser Asn Phe Leu Ser Pro Glu Lys
            660                 665                 670

Gln Asn Ser Lys Ser Asn Gly Ser Ala Gly Gly Ser Gly Gly Leu Asn
        675                 680                 685

Asp Ile Phe Glu Ala Gln Lys Ile Glu Trp His Glu
    690                 695                 700
```

<210> SEQ ID NO 152
<211> LENGTH: 699
<212> TYPE: PRT
<213> ORGANISM: Artificial
<220> FEATURE:
<223> OTHER INFORMATION: Sortilin SORTECDBAP_hB06-10

<400> SEQUENCE: 152

```
Arg Ser Thr Glu Gln Gly Glu Ser Cys Ser Gly Leu Leu Gly Ala Asp
1               5                   10                  15

Ala Lys Leu Ala Gly Asn Thr His Gln His Ile Phe Asn Asp Leu Ser
            20                  25                  30

Gly Ser Val Ser Leu Ala Trp Val Gly Asp Gly Thr Gly Val Ile Leu
        35                  40                  45

Ala Leu Thr Thr Phe Gln Val Pro Ile Phe Met Ile Thr Ile Gly Gln
    50                  55                  60

Ser Lys Leu Tyr Arg Ser Glu Asp Tyr Gly Lys Ser Phe Glu Asp Val
65                  70                  75                  80

Thr Asn Leu Ile Asn Asn Thr Phe Ile Arg Ser Asp Phe Gly Ile Ala
                85                  90                  95

Ile Gly Pro Glu Asn Ser Gly Lys Val Ile Leu Thr Ala Asp Val Ser
            100                 105                 110

Gly Ser His Gly Ser Arg Ile Phe Val Ser Ser Asp Phe Gly Lys Ser
        115                 120                 125
```

```
Phe Thr His Gln Glu Leu Pro Phe Val Pro Leu Met Gln Ile Thr Tyr
    130                 135                 140

Asn Pro Glu Asn Ser Asn Val Leu Leu Ala Leu Ser Asn Lys Asn Glu
145                 150                 155                 160

Leu Trp Leu Ser Glu Asp Phe Gly Thr Asn Trp Lys Lys Leu Tyr Asp
                165                 170                 175

Thr Val Cys Leu Ala Lys Trp Gly Arg Lys Gly Thr Ile Phe Phe Thr
            180                 185                 190

Ala Asn His Asn Gly Ser Cys Ser Asn Asp Arg Gly Met Leu Glu Leu
        195                 200                 205

Glu Arg Thr Thr Asp Tyr Gly Lys Ser Phe Lys Thr Val Ala Ser Lys
    210                 215                 220

Ile Tyr Ser Phe Gly Leu Gly Gly Lys Phe Leu Phe Ala Ser Val Met
225                 230                 235                 240

Thr Gly Lys Gly Thr Leu Arg Ala Ile His Val Ser Val Asp Asp Gly
                245                 250                 255

Asp Thr Trp Asn Met Ala Gln Leu Pro Ser Val Gly Gln Glu Gln Phe
            260                 265                 270

Tyr Ser Ile Leu Ala Ala Asn Asp Asp Met Val Phe Met His Val Asp
        275                 280                 285

Glu Pro Gly Asp Thr Gly Phe Gly Thr Ile Phe Thr Ser Asp Asp Arg
    290                 295                 300

Gly Ile Val Tyr Ser Lys Ser Leu Asp Arg His Leu Tyr Thr Thr Thr
305                 310                 315                 320

Gly Gly Glu Thr Asp Phe Thr Asn Val Thr Ser Leu Arg Gly Val Tyr
                325                 330                 335

Ile Thr Ser Val Leu Ser Glu Asp Asn Ser Ile Gln Thr Met Ile Thr
            340                 345                 350

Phe Asp Gln Gly Gly Arg Trp Thr His Leu Arg Lys Pro Glu Asn Ser
        355                 360                 365

Glu Cys Asp Ala Thr Ala Lys Asn Lys Asn Glu Cys Ser Leu His Ile
    370                 375                 380

His Ala Ser Tyr Ser Ile Ser Gln Lys Leu Asn Val Pro Met Ala Pro
385                 390                 395                 400

Leu Ser Glu Pro Asn Ala Val Gly Ile Val Ile Ala His Gly Ser Val
                405                 410                 415

Gly Asp Ala Ile Ser Val Met Val Pro Asp Val Tyr Ile Ser Asp Asp
            420                 425                 430

Gly Gly Tyr Ser Trp Thr Lys Met Leu Glu Gly Pro His Tyr Tyr Thr
        435                 440                 445

Ile Leu Asp Ser Gly Gly Ile Ile Val Ala Ile Glu His Ser Ser Arg
    450                 455                 460

Pro Ile Asn Val Ile Lys Phe Ser Thr Asp Glu Gly Gln Cys Trp Gln
465                 470                 475                 480

Thr Tyr Thr Phe Thr Arg Asp Pro Ile Tyr Phe Thr Gly Leu Ala Ser
                485                 490                 495

Glu Pro Gly Ala Arg Ser Met Asn Ile Ser Ile Trp Gly Phe Thr Glu
            500                 505                 510

Ser Phe Leu Thr Ser Gln Trp Val Ser Tyr Thr Ile Asp Phe Lys Asp
        515                 520                 525

Ile Leu Glu Arg Asn Cys Glu Glu Lys Asp Tyr Thr Ile Trp Leu Ala
    530                 535                 540
```

His Ser Thr Asp Pro Glu Asp Tyr Glu Asp Gly Cys Ile Leu Gly Tyr
545 550 555 560

Lys Glu Gln Phe Leu Arg Leu Arg Lys Ser Ser Val Cys Gln Asn Gly
565 570 575

Arg Asp Tyr Val Val Thr Lys Gln Pro Ser Ile Cys Leu Cys Ser Leu
580 585 590

Glu Asp Phe Leu Cys Asp Phe Gly Tyr Tyr Arg Pro Glu Asn Asp Ser
595 600 605

Lys Cys Val Glu Gln Pro Glu Leu Lys Gly His Asp Leu Glu Phe Cys
610 615 620

Leu Tyr Gly Arg Glu Glu His Leu Thr Thr Asn Gly Tyr Arg Lys Ile
625 630 635 640

Pro Gly Asp Lys Cys Gln Gly Gly Val Asn Pro Val Arg Glu Val Lys
645 650 655

Asp Leu Lys Lys Lys Cys Thr Ser Asn Phe Leu Ser Pro Glu Lys Gln
660 665 670

Asn Ser Lys Ser Asn Gly Ser Ala Gly Gly Ser Gly Gly Leu Asn Asp
675 680 685

Ile Phe Glu Ala Gln Lys Ile Glu Trp His Glu
690 695

<210> SEQ ID NO 153
<211> LENGTH: 700
<212> TYPE: PRT
<213> ORGANISM: Artificial
<220> FEATURE:
<223> OTHER INFORMATION: Sortilin SORTECDBAP_hB12390

<400> SEQUENCE: 153

Ser Ala Pro Gly Glu Asp Glu Glu Cys Gly Arg Val Arg Asp Phe Val
1 5 10 15

Ala Lys Leu Ala Asn Asn Thr His Gln His Val Phe Asp Asp Leu Arg
20 25 30

Gly Ser Val Ser Leu Ser Trp Val Gly Asp Ser Thr Gly Val Ile Leu
35 40 45

Val Leu Thr Thr Phe His Val Pro Leu Val Ile Met Thr Phe Gly Gln
50 55 60

Ser Lys Leu Tyr Arg Ser Glu Asp Tyr Gly Lys Asn Phe Lys Asp Ile
65 70 75 80

Thr Asp Leu Ile Asn Asn Thr Phe Ile Arg Thr Glu Phe Gly Met Ala
85 90 95

Ile Gly Pro Glu Asn Ser Gly Lys Val Val Leu Thr Ala Glu Val Ser
100 105 110

Gly Gly Ser Arg Gly Gly Arg Ile Phe Arg Ser Ser Asp Phe Ala Lys
115 120 125

Asn Phe Val Gln Thr Asp Leu Pro Phe His Pro Leu Thr Gln Met Met
130 135 140

Tyr Ser Pro Gln Asn Ser Asp Tyr Leu Leu Ala Leu Ser Thr Glu Asn
145 150 155 160

Gly Leu Trp Val Ser Lys Asn Phe Gly Gly Lys Trp Glu Glu Ile His
165 170 175

Lys Thr Val Cys Leu Ala Lys Trp Gly Arg Lys Gly Thr Ile Phe Phe
180 185 190

Thr Ala Asn His Asn Gly Ser Cys Ser Asn Asp Arg Gly Met Leu Glu
195 200 205

-continued

```
Leu Glu Arg Thr Thr Asp Tyr Gly Lys Ser Phe Lys Thr Val Ala Ser
    210                 215                 220

Lys Ile Tyr Ser Phe Gly Leu Gly Gly Lys Phe Leu Phe Ala Ser Val
225                 230                 235                 240

Met Thr Gly Lys Gly Thr Leu Arg Ala Ile His Val Ser Val Asp Asp
                245                 250                 255

Gly Asp Thr Trp Asn Met Ala Gln Leu Pro Pro Val Gly His Glu Gln
            260                 265                 270

Phe Tyr Ser Ile Leu Ala Ala Asn Asp Glu Met Val Phe Met His Val
        275                 280                 285

Asp Glu Pro Gly Asp Ser Gly Phe Gly Thr Ile Tyr Val Ser Asp Asp
    290                 295                 300

Arg Gly Thr Val Tyr Ser Lys Ser Leu Glu Arg His Leu Tyr Thr Thr
305                 310                 315                 320

Thr Gly Gly Glu Thr Asp Phe Ile Asn Val Thr Ser Leu Arg Gly Val
                325                 330                 335

Phe Thr Thr Ser Ile Leu Ala Glu Asp Lys Ser Val Gln Ser Val Ile
            340                 345                 350

Ser Phe Asp Gln Gly Gly Glu Trp Val Pro Leu Arg Lys Pro Ala Asp
        355                 360                 365

Ser Lys Cys Asp Ala Thr Ala Arg Asp Pro Glu Lys Cys Ser Leu His
    370                 375                 380

Ile His Ala Ala Tyr Ser Ile Ala Thr Gly Leu Asn Val Pro Met Leu
385                 390                 395                 400

Pro Leu Ser Glu Pro Asn Ala Val Gly Leu Val Leu Ala His Gly Ser
                405                 410                 415

Val Gly Asp Ala Ile Ser Val Met Arg Pro Asp Val Tyr Val Ser Asp
            420                 425                 430

Asp Gly Gly Tyr Thr Trp Ile Lys Ala Leu Glu Gly Pro His Tyr Tyr
        435                 440                 445

Thr Ile Leu Asp Ser Gly Gly Ile Ile Val Ala Ile Glu His Ser Ser
    450                 455                 460

Arg Pro Ile Asn Val Ile Lys Phe Ser Thr Asp Glu Gly Gln Cys Trp
465                 470                 475                 480

Gln Thr Tyr Thr Phe Thr Arg Asp Pro Ile Tyr Phe Thr Gly Leu Ala
                485                 490                 495

Ser Glu Pro Gly Ala Arg Ser Met Asn Ile Ser Ile Trp Gly Phe Thr
            500                 505                 510

Glu Ser Phe Leu Thr Ser Gln Trp Val Ser Tyr Thr Ile Asp Phe Lys
        515                 520                 525

Asp Ile Leu Glu Arg Asn Cys Glu Glu Lys Asp Tyr Thr Ile Trp Leu
    530                 535                 540

Ala His Ser Thr Asp Pro Glu Asp Tyr Glu Asp Gly Cys Ile Leu Gly
545                 550                 555                 560

Tyr Lys Glu Gln Phe Leu Arg Leu Arg Lys Ser Ser Val Cys Gln Asn
                565                 570                 575

Gly Arg Asp Tyr Val Val Thr Lys Gln Pro Ser Ile Cys Leu Cys Ser
            580                 585                 590

Leu Glu Asp Phe Leu Cys Asp Phe Gly Tyr Tyr Arg Pro Glu Asn Asp
        595                 600                 605

Ser Lys Cys Val Glu Gln Pro Glu Leu Lys Gly His Asp Leu Glu Phe
    610                 615                 620

Cys Leu Tyr Gly Arg Glu Glu His Leu Thr Thr Asn Gly Tyr Arg Lys
```

625 630 635 640

Ile Pro Gly Asp Lys Cys Gln Gly Gly Val Asn Pro Val Arg Glu Val
645 650 655

Lys Asp Leu Lys Lys Lys Cys Thr Ser Asn Phe Leu Ser Pro Glu Lys
660 665 670

Gln Asn Ser Lys Ser Asn Gly Ser Ala Gly Gly Ser Gly Gly Leu Asn
675 680 685

Asp Ile Phe Glu Ala Gln Lys Ile Glu Trp His Glu
690 695 700

<210> SEQ ID NO 154
<211> LENGTH: 700
<212> TYPE: PRT
<213> ORGANISM: Artificial
<220> FEATURE:
<223> OTHER INFORMATION: Sortilin SORTECDBAP_hB45678

<400> SEQUENCE: 154

Arg Ser Thr Glu Gln Gly Glu Ser Cys Ser Gly Leu Leu Gly Ala Asp
1 5 10 15

Ala Lys Leu Ala Gly Asn Thr His Gln His Ile Phe Asn Asp Leu Ser
20 25 30

Gly Ser Val Ser Leu Ala Trp Val Gly Asp Gly Thr Gly Val Ile Leu
35 40 45

Ala Leu Thr Thr Phe Gln Val Pro Ile Phe Met Ile Thr Ile Gly Gln
50 55 60

Ser Lys Leu Tyr Arg Ser Glu Asp Tyr Gly Lys Ser Phe Glu Asp Val
65 70 75 80

Thr Asn Leu Ile Asn Asn Thr Phe Ile Arg Ser Asp Phe Gly Ile Ala
85 90 95

Ile Gly Pro Glu Asn Ser Gly Lys Val Ile Leu Thr Ala Asp Val Ser
100 105 110

Gly Ser His Gly Ser Arg Ile Phe Val Ser Ser Asp Phe Gly Lys Ser
115 120 125

Phe Thr His Gln Glu Leu Pro Phe Val Pro Leu Met Gln Ile Thr Tyr
130 135 140

Asn Pro Glu Asn Ser Asn Val Leu Leu Ala Leu Ser Asn Lys Asn Glu
145 150 155 160

Leu Trp Leu Ser Glu Asp Phe Gly Thr Asn Trp Lys Lys Leu Tyr Asp
165 170 175

Ala Val Cys Leu Ala Lys Trp Gly Ser Asp Asn Thr Ile Phe Phe Thr
180 185 190

Thr Tyr Ala Asn Gly Ser Cys Lys Ala Asp Leu Gly Ala Leu Glu Leu
195 200 205

Trp Arg Thr Ser Asp Leu Gly Lys Ser Phe Lys Thr Ile Gly Val Lys
210 215 220

Ile Tyr Ser Phe Gly Leu Gly Gly Arg Phe Leu Phe Ala Ser Val Met
225 230 235 240

Ala Asp Lys Asp Thr Thr Arg Arg Ile His Val Ser Thr Asp Gln Gly
245 250 255

Asp Thr Trp Ser Met Ala Gln Leu Pro Ser Val Gly Gln Glu Gln Phe
260 265 270

Tyr Ser Ile Leu Ala Ala Asn Asp Asp Met Val Phe Met His Val Asp
275 280 285

Glu Pro Gly Asp Thr Gly Phe Gly Thr Ile Phe Thr Ser Asp Asp Arg 290 295 300

Gly Ile Val Tyr Ser Lys Ser Leu Asp Arg His Leu Tyr Thr Thr Thr
305 310 315 320

Gly Gly Glu Thr Asp Phe Thr Asn Val Thr Ser Leu Arg Gly Val Tyr
325 330 335

Ile Thr Ser Val Leu Ser Glu Asp Asn Ser Ile Gln Thr Met Ile Thr
340 345 350

Phe Asp Gln Gly Gly Arg Trp Thr His Leu Arg Lys Pro Glu Asn Ser
355 360 365

Glu Cys Asp Ala Thr Ala Lys Asn Lys Asn Glu Cys Ser Leu His Ile
370 375 380

His Ala Ser Tyr Ser Ile Ser Gln Lys Leu Asn Val Pro Met Ala Pro
385 390 395 400

Leu Ser Glu Pro Asn Ala Val Gly Ile Val Ile Ala His Gly Ser Val
405 410 415

Gly Asp Ala Ile Ser Val Met Val Pro Asp Val Tyr Ile Ser Asp Asp
420 425 430

Gly Gly Tyr Ser Trp Thr Lys Met Leu Glu Gly Pro His His Tyr Ala
435 440 445

Ile Leu Asp Ser Gly Gly Leu Leu Val Ala Val Glu Gln Asn Ala His
450 455 460

Gln Gly Val Asn Gln Ile Lys Phe Ser Thr Asp Glu Gly Gln Cys Trp
465 470 475 480

Gly Val Tyr Asn Phe Thr Lys Asp Pro Ile Phe Phe Thr Gly Leu Ala
485 490 495

Ser Glu Pro Gly Ala Arg Ser Met Asn Val Ser Leu Trp Gly Tyr Arg
500 505 510

Ser Ser Leu Phe His Gln Tyr Trp Ile Ser Phe Thr Ile Asp Phe Arg
515 520 525

Asp Leu Ile Thr Arg Asn Cys Glu Glu Lys Asp Tyr Thr Ile Trp Leu
530 535 540

Ala His Ser Thr Asp Pro Glu Asp Tyr Glu Asp Gly Cys Ile Leu Gly
545 550 555 560

Tyr Lys Glu Gln Phe Leu Arg Leu Arg Lys Ser Ser Val Cys Gln Asn
565 570 575

Gly Arg Asp Tyr Val Val Thr Lys Gln Pro Ser Ile Cys Leu Cys Ser
580 585 590

Leu Glu Asp Phe Leu Cys Asp Phe Gly Tyr Tyr Arg Pro Glu Asn Asp
595 600 605

Ser Lys Cys Val Glu Gln Pro Glu Leu Lys Gly His Asp Leu Glu Phe
610 615 620

Cys Leu Tyr Gly Arg Glu Glu His Leu Thr Thr Asn Gly Tyr Arg Lys
625 630 635 640

Ile Pro Gly Asp Lys Cys Gln Gly Gly Val Asn Pro Val Arg Glu Val
645 650 655

Lys Asp Leu Lys Lys Lys Cys Thr Ser Asn Phe Leu Ser Pro Glu Lys
660 665 670

Gln Asn Ser Lys Ser Asn Gly Ser Ala Gly Gly Ser Gly Gly Leu Asn
675 680 685

Asp Ile Phe Glu Ala Gln Lys Ile Glu Trp His Glu
690 695 700

<210> SEQ ID NO 155

<211> LENGTH: 763
<212> TYPE: PRT
<213> ORGANISM: Artificial
<220> FEATURE:
<223> OTHER INFORMATION: Sortilin SORTECD_HIS

<400> SEQUENCE: 155

Met Glu Arg Pro Trp Gly Ala Ala Asp Gly Leu Ser Arg Trp Pro His
1 5 10 15

Gly Leu Gly Leu Leu Leu Leu Leu Gln Leu Leu Pro Pro Ser Thr Leu
20 25 30

Ser Gln Asp Arg Leu Asp Ala Pro Pro Pro Pro Ala Ala Pro Leu Pro
35 40 45

Arg Trp Ser Gly Pro Ile Gly Val Ser Trp Gly Leu Arg Ala Ala Ala
50 55 60

Ala Gly Gly Ala Phe Pro Arg Gly Gly Arg Trp Arg Arg Ser Ala Pro
65 70 75 80

Gly Glu Asp Glu Glu Cys Gly Arg Val Arg Asp Phe Val Ala Lys Leu
85 90 95

Ala Asn Asn Thr His Gln His Val Phe Asp Asp Leu Arg Gly Ser Val
100 105 110

Ser Leu Ser Trp Val Gly Asp Ser Thr Gly Val Ile Leu Val Leu Thr
115 120 125

Thr Phe His Val Pro Leu Val Ile Met Thr Phe Gly Gln Ser Lys Leu
130 135 140

Tyr Arg Ser Glu Asp Tyr Gly Lys Asn Phe Lys Asp Ile Thr Asp Leu
145 150 155 160

Ile Asn Asn Thr Phe Ile Arg Thr Glu Phe Gly Met Ala Ile Gly Pro
165 170 175

Glu Asn Ser Gly Lys Val Val Leu Thr Ala Glu Val Ser Gly Gly Ser
180 185 190

Arg Gly Gly Arg Ile Phe Arg Ser Ser Asp Phe Ala Lys Asn Phe Val
195 200 205

Gln Thr Asp Leu Pro Phe His Pro Leu Thr Gln Met Met Tyr Ser Pro
210 215 220

Gln Asn Ser Asp Tyr Leu Leu Ala Leu Ser Thr Glu Asn Gly Leu Trp
225 230 235 240

Val Ser Lys Asn Phe Gly Gly Lys Trp Glu Glu Ile His Lys Ala Val
245 250 255

Cys Leu Ala Lys Trp Gly Ser Asp Asn Thr Ile Phe Phe Thr Thr Tyr
260 265 270

Ala Asn Gly Ser Cys Lys Ala Asp Leu Gly Ala Leu Glu Leu Trp Arg
275 280 285

Thr Ser Asp Leu Gly Lys Ser Phe Lys Thr Ile Gly Val Lys Ile Tyr
290 295 300

Ser Phe Gly Leu Gly Gly Arg Phe Leu Phe Ala Ser Val Met Ala Asp
305 310 315 320

Lys Asp Thr Thr Arg Arg Ile His Val Ser Thr Asp Gln Gly Asp Thr
325 330 335

Trp Ser Met Ala Gln Leu Pro Ser Val Gly Gln Glu Gln Phe Tyr Ser
340 345 350

Ile Leu Ala Ala Asn Asp Asp Met Val Phe Met His Val Asp Glu Pro
355 360 365

Gly Asp Thr Gly Phe Gly Thr Ile Phe Thr Ser Asp Asp Arg Gly Ile
370 375 380

```
Val Tyr Ser Lys Ser Leu Asp Arg His Leu Tyr Thr Thr Thr Gly Gly
385                 390                 395                 400

Glu Thr Asp Phe Thr Asn Val Thr Ser Leu Arg Gly Val Tyr Ile Thr
                405                 410                 415

Ser Val Leu Ser Glu Asp Asn Ser Ile Gln Thr Met Ile Thr Phe Asp
            420                 425                 430

Gln Gly Gly Arg Trp Thr His Leu Arg Lys Pro Glu Asn Ser Glu Cys
        435                 440                 445

Asp Ala Thr Ala Lys Asn Lys Asn Glu Cys Ser Leu His Ile His Ala
    450                 455                 460

Ser Tyr Ser Ile Ser Gln Lys Leu Asn Val Pro Met Ala Pro Leu Ser
465                 470                 475                 480

Glu Pro Asn Ala Val Gly Ile Val Ile Ala His Gly Ser Val Gly Asp
                485                 490                 495

Ala Ile Ser Val Met Val Pro Asp Val Tyr Ile Ser Asp Asp Gly Gly
            500                 505                 510

Tyr Ser Trp Thr Lys Met Leu Glu Gly Pro His Tyr Tyr Thr Ile Leu
        515                 520                 525

Asp Ser Gly Gly Ile Ile Val Ala Ile Glu His Ser Ser Arg Pro Ile
    530                 535                 540

Asn Val Ile Lys Phe Ser Thr Asp Glu Gly Gln Cys Trp Gln Thr Tyr
545                 550                 555                 560

Thr Phe Thr Arg Asp Pro Ile Tyr Phe Thr Gly Leu Ala Ser Glu Pro
                565                 570                 575

Gly Ala Arg Ser Met Asn Ile Ser Ile Trp Gly Phe Thr Glu Ser Phe
            580                 585                 590

Leu Thr Ser Gln Trp Val Ser Tyr Thr Ile Asp Phe Lys Asp Ile Leu
        595                 600                 605

Glu Arg Asn Cys Glu Glu Lys Asp Tyr Thr Ile Trp Leu Ala His Ser
    610                 615                 620

Thr Asp Pro Glu Asp Tyr Glu Asp Gly Cys Ile Leu Gly Tyr Lys Glu
625                 630                 635                 640

Gln Phe Leu Arg Leu Arg Lys Ser Ser Val Cys Gln Asn Gly Arg Asp
                645                 650                 655

Tyr Val Val Thr Lys Gln Pro Ser Ile Cys Leu Cys Ser Leu Glu Asp
            660                 665                 670

Phe Leu Cys Asp Phe Gly Tyr Tyr Arg Pro Glu Asn Asp Ser Lys Cys
        675                 680                 685

Val Glu Gln Pro Glu Leu Lys Gly His Asp Leu Glu Phe Cys Leu Tyr
    690                 695                 700

Gly Arg Glu Glu His Leu Thr Thr Asn Gly Tyr Arg Lys Ile Pro Gly
705                 710                 715                 720

Asp Lys Cys Gln Gly Gly Val Asn Pro Val Arg Glu Val Lys Asp Leu
                725                 730                 735

Lys Lys Lys Cys Thr Ser Asn Phe Leu Ser Pro Glu Lys Gln Asn Ser
            740                 745                 750

Lys Ser Asn His His His His His His His His
        755                 760
```

<210> SEQ ID NO 156
<211> LENGTH: 696
<212> TYPE: PRT
<213> ORGANISM: Artificial
<220> FEATURE:

<223> OTHER INFORMATION: HDX-MS Sequence

<400> SEQUENCE: 156

Ser Ala Pro Gly Glu Asp Glu Glu Cys Gly Arg Val Arg Asp Phe Val
1 5 10 15

Ala Lys Leu Ala Asn Asn Thr His Gln His Val Phe Asp Asp Leu Arg
20 25 30

Gly Ser Val Ser Leu Ser Trp Val Gly Asp Ser Thr Gly Val Ile Leu
35 40 45

Val Leu Thr Thr Phe His Val Pro Leu Val Ile Met Thr Phe Gly Gln
50 55 60

Ser Lys Leu Tyr Arg Ser Glu Asp Tyr Gly Lys Asn Phe Lys Asp Ile
65 70 75 80

Thr Asp Leu Ile Asn Asn Thr Phe Ile Arg Thr Glu Phe Gly Met Ala
85 90 95

Ile Gly Pro Glu Asn Ser Gly Lys Val Val Leu Thr Ala Glu Val Ser
100 105 110

Gly Gly Ser Arg Gly Gly Arg Ile Phe Arg Ser Ser Asp Phe Ala Lys
115 120 125

Asn Phe Val Gln Thr Asp Leu Pro Phe His Pro Leu Thr Gln Met Met
130 135 140

Tyr Ser Pro Gln Asn Ser Asp Tyr Leu Leu Ala Leu Ser Thr Glu Asn
145 150 155 160

Gly Leu Trp Val Ser Lys Asn Phe Gly Gly Lys Trp Glu Glu Ile His
165 170 175

Lys Ala Val Cys Leu Ala Lys Trp Gly Ser Asp Asn Thr Ile Phe Phe
180 185 190

Thr Thr Tyr Ala Asn Gly Ser Cys Lys Ala Asp Leu Gly Ala Leu Glu
195 200 205

Leu Trp Arg Thr Ser Asp Leu Gly Lys Ser Phe Lys Thr Ile Gly Val
210 215 220

Lys Ile Tyr Ser Phe Gly Leu Gly Gly Arg Phe Leu Phe Ala Ser Val
225 230 235 240

Met Ala Asp Lys Asp Thr Thr Arg Arg Ile His Val Ser Thr Asp Gln
245 250 255

Gly Asp Thr Trp Ser Met Ala Gln Leu Pro Ser Val Gly Gln Glu Gln
260 265 270

Phe Tyr Ser Ile Leu Ala Ala Asn Asp Asp Met Val Phe Met His Val
275 280 285

Asp Glu Pro Gly Asp Thr Gly Phe Gly Thr Ile Phe Thr Ser Asp Asp
290 295 300

Arg Gly Ile Val Tyr Ser Lys Ser Leu Asp Arg His Leu Tyr Thr Thr
305 310 315 320

Thr Gly Gly Glu Thr Asp Phe Thr Asn Val Thr Ser Leu Arg Gly Val
325 330 335

Tyr Ile Thr Ser Val Leu Ser Glu Asp Asn Ser Ile Gln Thr Met Ile
340 345 350

Thr Phe Asp Gln Gly Gly Arg Trp Thr His Leu Arg Lys Pro Glu Asn
355 360 365

Ser Glu Cys Asp Ala Thr Ala Lys Asn Lys Asn Glu Cys Ser Leu His
370 375 380

Ile His Ala Ser Tyr Ser Ile Ser Gln Lys Leu Asn Val Pro Met Ala
385 390 395 400

```
Pro Leu Ser Glu Pro Asn Ala Val Gly Ile Val Ile Ala His Gly Ser
                405                 410                 415

Val Gly Asp Ala Ile Ser Val Met Val Pro Asp Val Tyr Ile Ser Asp
            420                 425                 430

Asp Gly Gly Tyr Ser Trp Thr Lys Met Leu Glu Gly Pro His Tyr Tyr
        435                 440                 445

Thr Ile Leu Asp Ser Gly Gly Ile Ile Val Ala Ile Glu His Ser Ser
    450                 455                 460

Arg Pro Ile Asn Val Ile Lys Phe Ser Thr Asp Glu Gly Gln Cys Trp
465                 470                 475                 480

Gln Thr Tyr Thr Phe Thr Arg Asp Pro Ile Tyr Phe Thr Gly Leu Ala
                485                 490                 495

Ser Glu Pro Gly Ala Arg Ser Met Asn Ile Ser Ile Trp Gly Phe Thr
            500                 505                 510

Glu Ser Phe Leu Thr Ser Gln Trp Val Ser Tyr Thr Ile Asp Phe Lys
        515                 520                 525

Asp Ile Leu Glu Arg Asn Cys Glu Glu Lys Asp Tyr Thr Ile Trp Leu
    530                 535                 540

Ala His Ser Thr Asp Pro Glu Asp Tyr Glu Asp Gly Cys Ile Leu Gly
545                 550                 555                 560

Tyr Lys Glu Gln Phe Leu Arg Leu Arg Lys Ser Ser Val Cys Gln Asn
                565                 570                 575

Gly Arg Asp Tyr Val Val Thr Lys Gln Pro Ser Ile Cys Leu Cys Ser
            580                 585                 590

Leu Glu Asp Phe Leu Cys Asp Phe Gly Tyr Tyr Arg Pro Glu Asn Asp
        595                 600                 605

Ser Lys Cys Val Glu Gln Pro Glu Leu Lys Gly His Asp Leu Glu Phe
    610                 615                 620

Cys Leu Tyr Gly Arg Glu Glu His Leu Thr Thr Asn Gly Tyr Arg Lys
625                 630                 635                 640

Ile Pro Gly Asp Lys Cys Gln Gly Gly Val Asn Pro Val Arg Glu Val
                645                 650                 655

Lys Asp Leu Lys Lys Lys Cys Thr Ser Asn Phe Leu Ser Pro Glu Lys
            660                 665                 670

Gln Asn Ser Lys Ser Asn Ser Gly Ser Ala Met Ile Glu Gly Arg Gly
        675                 680                 685

Val Gly His His His His His His
    690                 695
```

<210> SEQ ID NO 157
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 157

```
Tyr Thr Ile Trp Leu Ala His Ser Thr Asp Pro Glu Asp
1               5                   10
```

<210> SEQ ID NO 158
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 158

```
Tyr Glu Asp Gly Cys Ile Leu Gly
1               5


<210> SEQ ID NO 159
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 159

Gly Tyr Lys Glu Gln Phe
1               5


<210> SEQ ID NO 160
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 160

Tyr Val Val Thr Lys Gln Pro Ser Ile Cys Leu
1               5                   10


<210> SEQ ID NO 161
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 161

Cys Ser Leu Glu Asp
1               5


<210> SEQ ID NO 162
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 162

Tyr Arg Lys Ile Pro Gly Asp Lys Cys Gln Gly Gly Val Asn
1               5                   10
```